(12) United States Patent
Sprogøe et al.

(10) Patent No.: US 12,016,903 B2
(45) Date of Patent: *Jun. 25, 2024

(54) LONG-ACTING GROWTH HORMONE TREATMENT

(71) Applicant: Ascendis Pharma Endocrinology Division A/S, Hellerup (DK)

(72) Inventors: Kennett Sprogøe, Holte (DK); Henrik Egesborg, Hellerup (DK); Steen Jensen, Dragoer (DK); Thomas Kurpiers, Heidelberg (DE)

(73) Assignee: ASCENDIS PHARMA ENDOCRINOLOGY DIVISION A/S, Hellerup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/528,350

(22) PCT Filed: Nov. 20, 2015

(86) PCT No.: PCT/EP2015/077229
§ 371 (c)(1),
(2) Date: May 19, 2017

(87) PCT Pub. No.: WO2016/079302
PCT Pub. Date: May 26, 2016

(65) Prior Publication Data
US 2017/0312342 A1    Nov. 2, 2017

(30) Foreign Application Priority Data

Nov. 21, 2014    (EP) ..................................... 14194248

(51) Int. Cl.
| | | |
|---|---|---|
| A61K 38/27 | (2006.01) | |
| A61K 9/00 | (2006.01) | |
| A61K 9/19 | (2006.01) | |
| A61K 47/60 | (2017.01) | |
| A61M 5/19 | (2006.01) | |

(52) U.S. Cl.
CPC ............ *A61K 38/27* (2013.01); *A61K 9/0019* (2013.01); *A61K 9/19* (2013.01); *A61K 47/60* (2017.08); *A61M 5/19* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 5,057,417 A | 10/1991 | Hammonds et al. |
| 5,073,627 A | 12/1991 | Curtis et al. |
| 5,171,220 A | 12/1992 | Morimoto |
| 5,179,080 A | 1/1993 | Rothkopf et al. |
| 5,472,706 A | 12/1995 | Friedman et al. |
| 5,478,925 A | 12/1995 | Wallach et al. |
| 5,645,010 A | 7/1997 | Lundstrom |
| 5,971,953 A | 10/1999 | Bachynsky |
| 6,284,282 B1 | 9/2001 | Maa et al. |
| 7,144,978 B2 | 12/2006 | Huang et al. |
| 7,879,588 B2 | 2/2011 | Vetter et al. |
| 7,968,085 B2 | 6/2011 | Hersel et al. |
| 9,272,048 B2 | 3/2016 | Rau et al. |
| 9,511,122 B2 | 12/2016 | Rasmussen et al. |
| 9,919,033 B2 | 3/2018 | Rasmussen et al. |
| 10,098,930 B2 | 10/2018 | Rau et al. |
| 10,682,395 B2 | 6/2020 | Rau et al. |
| 10,799,563 B2 * | 10/2020 | Kurpiers ................. A61P 13/12 |
| 10,960,053 B2 | 3/2021 | Rau et al. |
| 2003/0171285 A1 | 9/2003 | Finn et al. |
| 2006/0135427 A1 | 6/2006 | Hays et al. |
| 2006/0183198 A1 | 8/2006 | Buechler et al. |
| 2006/0257479 A1 | 11/2006 | Jensen et al. |
| 2006/0275252 A1 | 12/2006 | Harris et al. |
| 2008/0063727 A1 | 3/2008 | Kim et al. |
| 2008/0113914 A1 | 5/2008 | Hays et al. |
| 2008/0241102 A1 | 10/2008 | Hersel et al. |
| 2010/0197573 A1 | 8/2010 | Dorwald et al. |
| 2010/0291021 A1 | 11/2010 | Vetter et al. |

(Continued)

FOREIGN PATENT DOCUMENTS

| | | |
|---|---|---|
| EP | 0 211 257 | 2/1987 |
| EP | 0 022 242 | 11/1992 |

(Continued)

OTHER PUBLICATIONS

Palchuck et al. AMIA 2006 Symposium Proceedings p. 1055.*
Gohil Pipeline Plus vol. 40(11): 772-773, 2015.*
Genotropin insert, Pharmacia & Upjohn Co. LAB-0222-9.0, 2006.*
Nutropin Depot™ Clean Package Insert (1999).*
Barbour et al. (Pediatric Pharmacol. 54(2): 206-214, 2013).*
Said et al. (Pharmacol. & Pharmacy, 4: 556-565, 2013).*
Swanson (Seattle Mama Doc, 2011; https://seattlemamadoc.seattlechildrens.org/how-to-dose-acetaminophen-or-ibuprofen/).*
https://adisinsight.springer.com/print/drugs/800031668.*
MacGillivray et al. (Pediatrics 102: 527-530, 1998).*
Ranke et al. J Clin Endocrinol Metab 84: 1174-1183, 1999.*
Cleland et al. (J. Pharm. Sci. 101: 2744-2754, 2012).*

(Continued)

Primary Examiner — Christine J Saoud
(74) Attorney, Agent, or Firm — Alston & Bird LLP

(57) ABSTRACT

The present invention relates a pharmaceutical formulation comprising a long-acting growth hormone for use in a method of treating growth hormone deficiency, wherein the long-acting growth hormone formulation is administered to a patient in a bracketed dosage regimen, to a multitude of unit dosage forms comprising a long-acting growth hormone formulation, wherein the unit dosage forms comprise increasing amounts of growth hormone equivalents and wherein the amount of growth hormone equivalents increases by at least 10% between one unit dosage form and the next higher dosage form; their use in a method of treating growth hormone deficiency and method of treating growth hormone deficiency in a bracketed dosing regimen.

20 Claims, No Drawings

Specification includes a Sequence Listing.

(56) References Cited

U.S. PATENT DOCUMENTS

| | | | |
|---|---|---|---|
| 2011/0009315 | A1 | 1/2011 | Hersel et al. |
| 2011/0053848 | A1 | 3/2011 | Cleemann et al. |
| 2011/0112021 | A1 | 5/2011 | Rau et al. |
| 2011/0172390 | A1 | 7/2011 | Vetter et al. |
| 2011/0223230 | A1 | 9/2011 | Hersel et al. |
| 2012/0035101 | A1 | 2/2012 | Fares et al. |
| 2012/0058084 | A1 | 3/2012 | Rau et al. |
| 2012/0156259 | A1 | 6/2012 | Rau et al. |
| 2012/0156260 | A1 | 6/2012 | Rau et al. |
| 2012/0322721 | A1 | 12/2012 | Rasmussen et al. |
| 2020/0261544 | A1 | 8/2020 | Rau et al. |
| 2020/0390864 | A1 | 12/2020 | Rau et al. |
| 2021/0220442 | A1 | 7/2021 | Rau et al. |
| 2022/0088147 | A1 | 3/2022 | Sprogøe et al. |

FOREIGN PATENT DOCUMENTS

| | | | |
|---|---|---|---|
| EP | 0 809 996 | | 12/1997 |
| EP | 0 975 369 | | 12/2003 |
| EP | 1 196 443 | | 5/2004 |
| EP | 1 579 873 | | 9/2005 |
| EP | 1 625 855 | | 2/2006 |
| EP | 1 562 634 | | 8/2006 |
| EP | 1 715 887 | | 6/2007 |
| EP | 2 113 256 | | 11/2009 |
| EP | 2 119 726 | | 11/2009 |
| JP | H-1067800 | | 3/1998 |
| JP | 2007-515463 | | 6/2007 |
| JP | 2007-530485 | A | 11/2007 |
| RU | 2229288 | C2 | 5/2004 |
| WO | WO 1994/10308 | | 5/1994 |
| WO | WO 1999/30727 | | 6/1999 |
| WO | WO 2001/047562 | | 7/2001 |
| WO | WO 2001/78683 | | 10/2001 |
| WO | WO 2002/083180 | | 10/2002 |
| WO | WO 2002/089789 | | 11/2002 |
| WO | WO 2003/044056 | | 11/2003 |
| WO | WO 2004/043493 | | 5/2004 |
| WO | WO 2005/027978 | | 3/2005 |
| WO | WO 2005/034909 | | 4/2005 |
| WO | WO 2005/061005 | | 7/2005 |
| WO | WO 2006/084888 | | 8/2005 |
| WO | WO 2005/079838 | | 9/2005 |
| WO | WO 2005/099768 | | 10/2005 |
| WO | WO 2006/0003014 | | 1/2006 |
| WO | WO 2006/071840 | | 7/2006 |
| WO | WO 2006/076471 | | 7/2006 |
| WO | WO 2006/102659 | | 9/2006 |
| WO | WO 2006/136586 | | 12/2006 |
| WO | WO 2007/025988 | | 3/2007 |
| WO | WO 2007/075534 | A2 | 7/2007 |
| WO | WO 2007/114881 | | 10/2007 |
| WO | WO 2008/112155 | | 9/2008 |
| WO | WO 2008/155134 | | 12/2008 |
| WO | WO 2009/095479 | | 8/2009 |
| WO | WO 2009/133137 | | 11/2009 |
| WO | WO 2011/03234 | A2 | 6/2011 |
| WO | WO 2011/073234 | | 6/2011 |
| WO | WO 2011/073234 | A2 | 6/2011 |
| WO | WO 2011/123813 | | 10/2011 |
| WO | WO 2011/144756 | | 11/2011 |
| WO | WO 2014/060512 | | 4/2014 |
| WO | WO 2016/079114 | A1 | 5/2016 |
| WO | WO 2016/079302 | A1 | 5/2016 |
| WO | WO 2016/109823 | A1 | 7/2016 |
| WO | WO 2020/178273 | A1 | 9/2020 |
| WO | WO 2004/019993 | | 1/2023 |
| WO | WO 2008/084237 | | 1/2023 |

OTHER PUBLICATIONS

International Search Report issued in corresponding international Application No. PCT/EP2015/077229 dated Feb. 6, 2016, 3 pages.

Davis, et al., "The effect of bovine somatotroin in a sustained release preparation (Somidobove) on milk production of cows at pasture in New Zealand," New Zealand Journal of Agricultural Research, vol. 42, 315-323, (1999).

Hoybye, et al., "A Phase 2, Multiple-Dose, Open-Label, Parallel-Group, Active Controlled, Safety, Tolerability, Pharmacokinetic and Pharmacodynamic Study of ACP-001 in Adult Patients with Growth Hormone Deficiency (AGHD) : What's New in Diagnosis & Treatment of GH Dysfunction? (Clinical)", The Endocrine Society's 94th Annual Meeting and Expo, Jun. 23-26, 2012—Houston, TX—, (Jun. 23, 2012), pp. OR29-4, XP055246166 [Y] 3,4,38,39, abstract only.

Kemp, et al., "Pharmacokinetic and Pharmacodynamic Characteristics of a Long-Acting Growth Hormone (GH) Preparation (Nutropin Depot) in GH-Deficient Children," The Journal of Clinical Endocrinology & Metabolism, 89(7): 3234-3240, (Jul. 2004).

Neutropin Depot, 2.B Clean Packge Insert, FDA.gov, XP055185385, (Dec. 1999).

SKYTROFAtm, Highlights of Prescribing Information, Reference ID: 4846899, revised (Aug. 2021).

A. Semlaty et al., Properties and Formulation of Oral Drug Delivery Systems of Protein and Peptides, 69(6) IND1'N J. Pharmaceutical Sci. 741-747 (2007).

Alam et al., "Synthesis and purification of a deleted human growth hormone, hGHA135-146: sensitivity to plasmin cleavage and in vitro and in vivo bioactivities", J. of Biotechnology, 78, 49-59, 2000, Elsevier.

Antezak et al., "A New Acivicin Prodrug Designed for Tumor-Targeted Delivery", Bioorganic & Medicinal Chemistry, 9, 2843-2848, 2001, Elsevier.

Belikov, "Farmazevtit'cheskaya Khimia (Pharmaceutical chemistry)", Part I, Moscov "Vysshaya shkola", pp. 43-45 (1993). English translation.

Bowie et al., Deciphering the Message in Rotein Sequences: Tolerance to Amino Acid Substitutions: Science, 247, 1306-1310, 1990, Highwire Press.

Buyukgebiz et al., "Localized Lipoatrophy due to Recombinant Growth Hormone Therapy in a Child with 6.7 Kilobase Gene Deletion Isolated Growth Hormone Deficiency", J. of Pediatric Endocrinology & Metabolism, 12, 95-97, 1999, Freund Publishing House Ltd., London.

Cheng et al., "Synthesis of Linear, fl-Cyclodextrin-Based Polymers and Their Camptothecin Conjugates", Bioconjugate Chem., 14, 1007-1017, 2003, American Chemical Society.

Clark et al., "Long-acting Growth Hormones Produced by Conjugation with Polyethylene Glycol", J. Biol. Chem., 271:36, 21969-21977, Sep. 1996, American Society for Biochemistry and Molecular Biology, Inc.

Dag, et al., "Preparation of 3-Arm Star Polymers (A3) via Diels-Alder Click Reaction," Journal of Polymer Science: Part A: Polymer Chemistry, 46, 302-313, (2007).

Garman et al., "The preparation and properties of novel reversible polymer-protein conjugates", FEBS Letters, 223:2, 361-365, Nov. 1987, Elsevier.

Genentech Inc., Nutropin AQ0, obtained from http://www.accessdata.fda.gov/drugsatfda docs/labe1/2005/020522s021,0221bl.pdf, p. 1-27 (2004).

Graham, et al., "AAS, Growth Hormone, And Insulin Abuse: Psychological and Neuroendocrine Effects," 4(3) Therapeutics and Clinical Risk Management 587-597 (2008).

Greenwald et al., "A New Aliphatic Amino Prodrug System for the Delivery of Small Molecules and Proteins Utilizing Novel PEG Derivatives," 47 J. Med. Chemistry 726-734 (2004).

Greenwald et al., "Drug Delivery Systems Based on Trimethyl Lock Lactonization: Poly(ethylene glycol) Prodrugs of Amino-Containing Compounds," 43 J. Med. Chemistry 475-487 (2000).

Greenwald et al., "Drug Delivery Systems Employing 1,4- or 1,6-Elimination: Poly (ethylene glycol) Prodrugs of Amine-Containing Compounds", J. Med. Chem., 42, 3657-3667, 1999, American Chemical Society.

Grigorian et al., "Extraordinarily stable disulfide-linked homodimer of human growth hormone", Protein Sci., 14, 902-913, Mar. 1, 2005, Cold Spring Harbor Laboratory Press.

(56) References Cited

OTHER PUBLICATIONS

Haffner et al., "Metabolic Clearance of Recombinant Human Growth Hormone in Health and Chronic Renal Failure", J. Clin. Invest,, 93, 1163-1171, Mar. 1994, American Society for Clinical Investigation, Inc.
Kalia et al., "Hydrolytic Stability of Hydrazones and aames," 47 Angewandte Creme Int'l Edition 7523-7526 (2008).
Kidder et al., "Effects of Growth Hormone and Low Dose Estrogen on Bone Growth and Turnover in Long Bones of Hypophysectomized Rats," 61 Calcified Tissue Int'l 327-335 (1997).
Kumar et al., "Effect of Trehalose on Protein Structure," 18 Protein Sc'. 24-36 (2009).
Lee et al., "Drug Delivery Systems Employing 1,6-Elimination: Releasable Poly(ethylene glycol) Conjugates of Proteins", Bioconjugate Chan, 12, 163-169, 2001, American Chemical Society.
Lee et al., "Targeted Enzyme-responsive Drug Carriers: Studies on the Delivery of a Combination of Drugs", Angew. Chem., 116, 1707-1710, 2004, Wiley-VCR.
Luo et al., "A Hyaluronic Acid-Taxol Antitumor Bioconjugate Targeted to Cancer Cells", Biomacromolecules, I, 208-218, 2000, American Chemical Society.
Machlin, L,J., "Effect of Porcine Growth Hormone on Growth and Carcass Composition of the Pig", J. of Animal Science, 35, 794-800, 1972, ASAS.
Mehta, et al., "The Use of Somatropin (Recombinant Growth Hormone) in Children of Short Stature," Pediatr Drugs, 4(1): 37-47, (2002).
Monfardini et al., "A Branched Monotnethoxypoly (Ethylene Glycol) for Protein Modification," 6 Bioconjugate Chemistry p. 62-69 (1995).
Nishiguchi, "What is PEG-IFN?" Strategy of New Interferon Therapy, Mebio (2002) pp. 20-23 (w/English Translation).
Pasut et al., "A New PEG-fl-Alanine Active Derivative for Releasable Protein Conjugation", Bioconjugate Chem., 19, 2427-2431, 2008, American Chemical Society.
Peleg-Shulman et al., "Reversible PEGylation: A Novel Technology to Release Native Interferon a2 over a Prolonged Time Period", J. Med. (hem., 47, 4897-4904, 2004, American Chemical Society.
Pfizer, Highlights of Prescribing Information, obtained from http://www.accessdataida.gov/scripts/cder/drugsatfda/index.cfm, p. 1-24 (2008).
Ron et al., "Expression of Biologically Active Recombinant Keratinocyte Growth Factor", J. of Biological Chemistry, 268:4, 2984-2988, 1993, NTH, Bethesda, Maryland.
Sengupta et al., "An audit of primary surgical treatment for women with ovarian cancer referred to a cancer centre", British J. of Cancer, 80:3/4, 444-447, 1999, Cancer Research Campaign.
Shabat et al., "Chemical Adaptor Systems", Chem. Eur. J., 10, 2626-2634, 2004, Wiley-VCH.
Shechter et al., "New Technologies to Prolong Life-time of Peptide and Protein Drugs In vivo", International Journal of Peptide Research and Therapeutics, 13:1-2, 105-117, Jun. 2007, Springer Science+Business Media, Inc.
Shechter et al., "Reversible PEGylation of peptide YY3-36 prolongs its inhibition of food intake in mice", FEBS Letters, 579, 2439-2444, 2005, Elsevier B.V.
Testa. Chapter 8 of Hydrolysis in Drug and Prodrug Metabolism, 419-523, Aug. 1, 2003, John Wiley & Sons. Clinical Focus: 45th Annual Meeting of the ESPE, Hormone Red 2006, 65 (suppl 4) 29-34. Clinical Focus: 45th Annual Meeting of the ESPE, Hormone Red 2006, 65 (suppl 4) 115-154.
Thorner, et al., "Growth Hormone GH Receptor Blaockade with a PEG-Modified GH (B2036-PEG) lowers Serum Insulin-Like Growth Factro-I but Does Not Acutely Stimulate Serum GH," The Journal of Cinical Endocrinology & Metabolism, Jun. 1999; 84-6, 2098-2103.
Tsubery et al., "Prolonging the Action of Protein and Peptide Drugs by a Novel Approach of Reversible Polyethylene Glycol Modification", J. of Biological Chemistry, 279:37, 38118-38124, Sep. 2004, American Society for Biochemistry and Molecular Biology, Inc.
Veronese, "Enzymes for human therapy: surface structure modifications", Chimicaoggi, 53-56, Jan.-Feb. 1989.
Veronese, Peptide and protein PEGylation: a review of problems and solutions,: Biomaterials, 22, 405-417, (2001).
Wang, "Lyophilixation and Development of Solid Protein Pharmaceuticals," 203 Int'l J. Pharmaceutics 1-60 (2002).
Wolf et al., "Growth Hormone and Insulin Reverse Net Whole Body and Skeletal Muscle Protein Catabolism in Cancer Patients," 216(3) Annals Surgery 280-288 (1992).
Zalipsky et al., "Thiolytically Cleavable Dithiobenzyl Urethane-Linked Polymer-Protein Conjugates as Macromolecular Prodrugs: Reversible PEGylation of Proteins", Bioconjugate Chan., 18, 1869-1878, 2007, American Chemical Society.
Garyu, Lianko G., U.S. Appl. No. 16/866,764, Non-Final Office Action dated Mar. 2, 2023, 25 pages, USPTO, USA.
Cordero Garcia, Marcela M., U.S. Appl. No. 17/006,589, Non-Final Office Action dated Jan. 24, 2023, 19 pages, USPTO, USA.
Cordero Garcia, Marcela M., U.S. Appl. No. 17/215,991, Non-Final Office Action dated May 8, 2023, 55 pages, USPTO, USA.
Cordero Garcia, Marcela M., U.S. Appl. No. 17/215,991, Requirement for Restriction/Election dated Jan. 27, 2023, 6 pages, USPTO.
Ha, Julie, U.S. Appl. No. 17/310,993, Requirement for Restriction/Election dated Apr. 27, 2023, 10 pages, USPTO, USA.
Gomez, Gallardo, S., WIPO, WO Application No. PCT/EP2020/055513, PCT International Search Report dated May 13, 2020, 5 pages, European Patent Office, Netherlands.
Wittmann-Regis, Agnes, WIPO, WO Application No. PCT/EP2009/055194, PCT International Preliminary Report on Patentability dated Nov. 2, 2010, 12 pages, The International Bureau of WIPO, Switzerland.
Orlando, Michele, WIPO, WO Application No. PCT/EP2009/055194, PCT International Search Report dated Nov. 9, 2009, 7 pages, European Patent Office, Netherlands.
Orlando, Michele, WIPO, WO Application No. PCT/EP2015/076813, PCT International Search Report dated Apr. 18, 2016, 7 pages, European Patent Office, Netherlands.
Lindner, Nora, WO Application No. PCT/EP2015/076913, PCT International Preliminary Report on Patentability dated May 23, 2017, 11 pages, The International Bureau of WIPO, Switzerland.
Lindner, Nora, WO Application No. PCT/EP2015/077229, PCT International Preliminary Report on Patentability dated May 23, 2017, 9 pages, The International Bureau of WIPO, Switzerland.
Marttin, Emmeline, WIPO, WO Application No. PCT/EP2015/077229, PCT International Search Report dated Feb. 11, 2016, 5 pages, European Patent Office, Netherlands.
Nikolaeva, T.V., English Translation of International Russian Office Action issued in corresponding International Application No. 2017121203 dated Oct. 15, 2019, Russian Patent Office, 7 pages, Russia.
Mukasa, Noriko, English Translation of Official Action dated Mar. 4, 2014 in counterpart Japanese Patent Application No. 2011-506705, Japanese Patent Office, 4 pages, Japan.
Marttin, Emmeline, WIPO, PCT/EP2015/077229 International Search Report dated Feb. 11, 2016, 5 pages, European Patent Office, Netherlands.
Garyu, Lianko G., U.S. Appl. No. 13/515,621, Advisory Action dated Dec. 29, 2014, 4 pages, USPTO, USA.
Garyu, Lianko G., U.S. Appl. No. 13/515,621, Final Office Action dated Sep. 23, 2015, 21 pages, USPTO, USA.
Garyu, Lianko G., U.S. Appl. No. 13/515,621, Final Office Action dated Oct. 7, 2014, 33 pages, USPTO, USA.
Garyu, Lianko G., U.S. Appl. No. 13/515,621, Non-Final Office Action dated Jan. 20, 2016, 20 pages, USPTO, USA.
Garyu, Lianko G., U.S. Appl. No. 13/515,621, Non-Final Office Action dated Apr. 14, 2015, 19 pages, USPTO, USA.
Kader, Khalid, U.S. Appl. No. 13/515,621, Non-Final Office Action dated Apr. 25, 2013, 14 pages, USPTO, USA.
Kader, Khalid, U.S. Appl. No. 13/515,621, Requirement for Restriction/Election dated Jan. 2, 2013, 9 paged, USPTO, USA.

(56) References Cited

OTHER PUBLICATIONS

Garyu, Lianko G., U.S. Appl. No. 15/340,595, Notice of Allowance dated Nov. 1, 2017, 9 pages, USPTO, USA.
Garyu, Lianko G., U.S. Appl. No. 15/901,350, Final Office Action dated Oct. 31, 2019, 6 pages, USPTO, USA.
Garyu, Lianko G., U.S. Appl. No. 15/901,350, Non-Final Office Action dated Apr. 16, 2019, 11 pages, USPTO, USA.
Garyu, Lianko G., U.S. Appl. No. 15/901,350, Notice of Allowance dated Feb. 7, 2020, 7 pages, USPTO, USA.
Garyu, Lianko G., U.S. Appl. No. 16/515,621, Notice of Allowance dated Aug. 2, 2016, 12 pages, USPTO, USA.
Garyu, Lianko G., U.S. Appl. No. 16/866,764, Final Office Action dated Oct. 12, 2022, 30 pages, USPTO, USA.
Cordero Garcia, Marcela M., U.S. Appl. No. 17/006,589, Requirement for Restriction/Election dated Nov. 9, 2022, 5 pages, USPTO, USA.
Kronester-Frei, A., WIPO, WO Application No. PCT/2010/069710, PCT Written Opinion of the International Searching Authority dated Feb. 28, 2012, 7 pages, European Patent Office, Germany.
Kronester-Frei, A., WIPO, WO Application No. PCT/EP2010/069710, PCT International Preliminary Report on Patentability dated Jul. 3, 2012, 8 pages, European Patent Office, Germany.
Kronester-Frei, A., WIPO, WO Application No. PCT/EP2010/069710, PCT International Search Report dated Feb. 28, 2012, 6 pages, European Patent Office, Germany.
Marttin, Emmeline, Ep 21201573 European Search Report dated Mar. 24, 2022, 13 pages, European Patent Office, Germany.
Cordero Garcia, Marcela M., U.S. Appl. No. 17/006,589, Notice of Allowance dated Jul. 17, 2023, 9 pages, USPTO, USA.
Garyu, Lianko G., U.S. Appl. No. 16/866,764, Final Office Action mailed Aug. 2, 2023, 25 pages, USPTO, USA.
Dyson, "Khimiya sintetitcheskikh lekarstvennykh veshhestv (May's Chemistry of synthethic drugs)," Lang., Moscow: "Mir", 1964, p. 12-19, English translation.
Populyarnaya medicinskaya enciklopediya, gl. Red. V. I. Pokrovskij, 4-e izd., UI. "KNIGOCHEJ", 1997, str. 317 (lekarstvennye sredstva) (= Popular medical encyclopedia, chief editor V. I. Pokrovskij, fourth edition, "KNIGOCHEJ", 1997, p. 317 (drugs) English translation.
Cordero Garcia, Marcela M., U.S. Appl. No. 17/215,991, Notice of Allowance and Interview Summary dated Nov. 9, 2023, 10 pages, USPTO, USA.
Reiter et al., "A multicenter study of the efficacy and safety of sustained release GH in the treatment of naïve pediatric patients with GH deficency," J Clin Endocrinol Metab. 2001; 86(10):4700-6.
Cleveland Clinic, "Growth Hormone Deficiency (GHD)," https://my.clevelandclinic.org/health/diseases/23343-gorwth-hormone-deficiency-ghd, pp. 1-17, accessed Sep. 21, 2023, (2023).
Pipelinereview, Handok-Genexine Long-Acting hGH Therapeutic "GX-H9" Receives Approval for Phase I Trial in Europe, pp. 1-2, Aug. 20, 2013, (2013).
Ha, Julie, U.S. Appl. No. 17/310,993, Non-Final Office Action dated Sep. 26, 2023, 14 pages, USPTO, USA.

\* cited by examiner

SEQUENCE LISTING

<160> NUMBER OF SEQ ID NOS: 1

<210> SEQ ID NO 1
<211> LENGTH: 191
<212> TYPE: PRT
<213> ORGANISM: Homo sapiens

<400> SEQUENCE: 1

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
        130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
                180                 185                 190
```

LONG-ACTING GROWTH HORMONE TREATMENT

The present application claims priority from PCT Patent Application No. PCT/EP2015/077229 filed on Nov. 20, 2015, which claims priority from European Patent Application No. EP 14194248.2 filed on Nov. 21, 2014, the disclosures of which are incorporated herein by reference in their entirety.

The present invention relates a pharmaceutical formulation comprising a long-acting growth hormone for use in a method of treating growth hormone deficiency, wherein the long-acting growth hormone formulation is administered to a patient in a bracketed dosage regimen, to a multitude of unit dosage forms comprising a long-acting growth hormone formulation, wherein the unit dosage forms comprise increasing amounts of growth hormone equivalents and wherein the amount of growth hormone equivalents increases by at least 10% between one unit dosage form and the next higher dosage form; their use in a method of treating growth hormone deficiency and method of treating growth hormone deficiency in a bracketed dosing regimen.

Human growth hormone (hGH) is widely used for the treatment of short stature resulting from GH deficiency (GHD) or insufficiency as well as other growth disorders. Growth hormone (GH) is currently only available in most territories as formulations requiring daily injections.

Prescription practices for daily growth hormone formulations indicate that dosing should be individualized based on the weight and growth response of each patient. Typical doses range, for example, from 0.17 mg/kg/week to 0.30 mg/kg/week for growth hormone deficient children. As conventional growth hormone therapy involves fixed dosing according to weight, the total dosage of growth hormone varies according to the weight of the child. This means that the dose given to the child is gradually adjusted upwards as the patient gets older and larger. Administration is via one of five broad categories of devices, i.e. via syringe with needle, injection pen, autoinjector pen, needle-free injector, or electronic injector.

Noncompliance with growth hormone therapy is widespread. Noncompliance with current hGH treatment is frequent since the drug needs to be injected daily over many years, and daily injections are perceived invasive by the patients. Noncompliance has a proven negative impact on the outcomes of treatment. Ease of use of the injection device, the features of injection devices as well as the frequency of injection may play an important role in compliance.

The injection devices vary in how the dose can be set before the injection is administered and ease of handling, for example insertion of the needle, manipulation of the button to deliver the growth hormone, removal of the needle from the pen after use, and whether the product requires refrigeration. Kappelgaard et al. (poster at the $7^{th}$ International Congress of the GRS and IGF society 2014, 15-18 Oct. in Singapore) reported that the proportion of patients who had disposed of hGH due to potential spoilage was significantly higher for users of products requiring refrigeration than for users of products that did not require refrigeration.

In addition to ease of use, the amount of waste related to drug administration is also a consideration when choosing growth hormone preparations due to the high cost of growth hormone therapy. When comparing daily growth hormone preparations, Bazalo et al. (Managed Care, September 2007: 45-51) concluded that pen devices are superior to vial and syringe, as pen delivery systems result in less waste than vial and syringe. In addition, the authors stated that the dosing increment determines how closely the pen can deliver the calculated dosage based on patient weight and concluded that dosing accuracy increases with finer dosing increments, and results in less product waste and consequently saves costs.

As pen devices for daily growth hormone administration contain multiple doses, patients who are unable to inject a full dose using the hGH remaining in a pen, are required to inject the remainder of the pen content and the full dose made up from a subsequent injection from a new device in order to reduce waste. This requirement both introduces the risk of miscalculating the correct dose and introduces additional discomfort for the patients in form an additional injection.

Wastage arising from current delivery system characteristics may have a material effect on the frequency with which patients need to refill their hGH prescriptions and, given the per milligram cost of hGH, may affect the cost of treatment from the health care payer perspective.

In addition to impacting cost, waste from daily growth hormone and long-acting growth hormone products constitute issues related to disposal. According to the U.S. Drug Enforcement Administration, growth hormone is commonly abused by athletes, bodybuilders and aging adults, and possession and distribution for illicit uses is punishable by law. To avoid diversion of growth hormone, any unused medicinal product or waste material should be disposed of in accordance with local requirements.

To improve compliance and treatment outcomes, several companies have developed technologies for creating long acting growth hormone products. Similar to daily growth hormone, long-acting growth hormones are dosed at a fixed dose of growth hormone per kg bodyweight.

Nutropin Depot® was the first long-acting growth hormone to be approved and was based on encapsulation of growth hormone in biodegradable microparticles. Nutropin Depot® was available on the US market, but was withdrawn in 2004.

Nutropin Depot® was intended for once-monthly or twice-monthly injections at a fixed dose of 1.5 mg/kg/month or 0.75 mg/kg/twice monthly. Nutropin Depot® was supplied in a vial and syringe and were available in a standard concentration of 19 mg/ml after reconstitution and 3 vials were available at a labeled content of 13.5 mg, 18 mg and 22.5 mg. Based on the monthly dose of 1.5 mg/kg/month, children weighing more than 15 kg required more than one injection.

Somatropin Biopartners (LB3002), was recently approved by the European Medicines Agency. Somatropin Biopartners (LB3002) is a long-acting growth hormone based on encapsulation of growth hormone in biodegradable microparticles. Somatropin Biopartners (LB3002) is indicated for weekly administration of a fixed dose of 0.5 mg/kg/week and is currently supplied in vial and syringes. Following preparation of the drug by mixing the lyophilized drug with appropriate diluents, the vial and syringe delivery system for Somatropin Biopartners (LB3002) allow patients to adjust the dose according to weight based on 50 µL increments in dosing volume, equivalent to 1 mg adjustments in dose.

Clinical trials have demonstrated that weight based dosing of pediatric patients with growth hormone deficiency at a fixed dose of 0.5 mg/kg/week results in height velocities comparable to daily growth hormone dose at 0.21 mg/kg/week, given as seven daily injections.

In addition to the two long acting growth hormone preparations that have received regulatory approval in Western countries, there are a number of long-acting growth hormone preparations in development. These all use a fixed dose regimen. Common practice for patients in need of GH therapy is prescribing a daily or long-acting growth hormone and determining the correct dose-size by multiplying the prescribed dose with the patient's weight. As the patient grows and his/her weight changes or if the prescribed dose is adjusted up or down, dose adjustment is achieved by selecting the appropriate dose-size based on the patient's weight and prescribed dose.

For example, VRS-317, now called somavaratan, has completed a phase 2b clinical trial, in which pediatric GHD patients were dosed with the same cumulative dose, but using different dosing frequencies. Specifically patients were dosed with a fixed dose of 1.25 mg/kg/week; 2.5 mg/kg/every two weeks or 5.0 mg/kg/month. An extension trial using a higher dose of 3.5 mg/kg/every two weeks was started to improve efficacy. This higher dose will be used in a Phase 3 study of somavaratan.

Lagova™ (MOD-4023, hGH-CTP) is dosed in a phase 2 dose range study in pediatric GHD patients using a fixed dose regimen at weekly intervals. Specifically patients were dosed with a fixed dose of 0.25 mg/kg/week; 0.48 mg/kg/week or 0.66 mg/kg/week.

TV-1106 (albutropin) is being studies in a phase 2 dose range study in pediatric GHD patients employing a weekly fixed dose regimen. Specifically patients were dosed with a fixed dose of 0.554 mg/kg/week; 0.924 mg/kg/week or 1.20 mg/kg/week.

NNC0195-0092 has been studied in a dose range study in growth hormone deficient adult at fixed doses. Specifically patients were dosed with a fixed dose of 0.02 mg/kg/week; 0.04 mg/kg/week; 0.08 mg/kg/week or 0.12 mg/kg/week. In a pediatric single dose study patients were dosed with a fixed dose of 0.02 mg/kg/week; 0.04 mg/kg/week; 0.08 mg/kg/week or 0.16 mg/kg/week.

As exemplified by the experience gained from clinical and experimental use of long-acting growth hormone, dosing is done by administering a fixed dose per kg of body weight, which is similar to current typical practice for administering daily growth hormone to children with growth hormone deficiency.

However, certain disadvantages are associated with fixed dose administration of a long-acting growth hormone. The dose required by the patients receiving a fixed dose based on their weight does not necessarily amount to the full amount of drug in the injection system, both Nutropin Depot® and Somatropin Biopartners (LB3002) require that any unused portion of the medication must be discarded. For example, waste associated with dosing across the weight range listed in the EMA summary of product characteristics for Somatropin Biopartners (LB3002) may be as high as 400% of the prescribed dose.

As the annual pediatric patient cost of growth hormone treatment may exceed $20,000, ensuring optimal efficacy and minimizing waste is an objective of this invention.

In summary, there is a need for a long-acting growth hormone that is efficacious, presented in a patient-friendly way and can be administered in a manner that produces as little waste as possible.

It is therefore an object of the present invention to at least partially overcome the shortcomings described above.

This object is achieved with a multitude of unit dosage forms comprising a long-acting growth hormone formulation, wherein the unit dosage forms comprise increasing amounts of growth hormone equivalents and wherein the amount of growth hormone equivalents increases by at least 10% between one unit dosage form and the next higher dosage form.

It was surprisingly found that the application of various fixed doses of a formulation comprising a long-acting growth hormone to patients in need of growth hormone treatment caused similar responses in these patients measured as annualized height velocity. This surprising finding led to a new dosage regimen and the provision of new unit dosage forms for long-acting growth hormone formulations.

It was surprisingly found that a multitude of unit dosage forms comprising long-acting growth hormone formulation with increasing amounts of growth hormone equivalents which increase by at least 10% allows the grouping of patients, preferably pediatric patients, in need of growth hormone treatment, into weight brackets, i.e. weight ranges, and administering to all patients of a certain weight bracket the full amount of long-acting growth hormone formulation comprised in a corresponding unit dosage form reduces or even eliminates waste without compromising efficacy.

Accordingly, in another aspect the present invention relates to a pharmaceutical formulation comprising a long-acting growth hormone for use in a method of treating growth hormone deficiency, wherein the long-acting growth hormone formulation is administered to a patient in a bracketed dosage regimen.

In another embodiment the present invention relates to a method of treating growth hormone deficiency, wherein the method comprises the step of administering to a patient in need thereof a long-acting growth hormone formulation in a bracketed dosing regimen.

Efficacy is evaluated by comparing height velocity over a certain time period in naïve growth hormone children treated with either the bracketed dosing regimen of this invention or conventional fixed weight based dosing of appropriate daily growth hormone doses.

Such dosage regimen has several advantages. In contrast to daily growth hormone preparations for which finer dosing increments are desired to minimize waste, it was found that waste can be minimized by increasing the dosing increments and dosing patients using a bracketed dosing regimen. This provides a very economical way to minimize costs which may help to reduce overall healthcare cost.

By providing patients that can benefit from growth hormone therapy a long-acting growth hormone with bracketed doses also greatly simplifies the treatment regimen, as precise calculation of the dose and adjustment of a pen device or preparation of vial and syringe to administer the precise dose is not necessary. Furthermore, bracketed dosing enables empty-all delivery devices which minimize waste and also eliminate the potential for misuse of any residual long-acting growth hormone comprised in a discarded container.

In summary, the bracketed dosage regimen of the present invention causes similar responses in patients measured as annualized height velocity as the standard fixed dosage regimen while at the same time reduces waste of the long-acting growth hormone formulation and simplifies the treatment regimen.

Within the present invention the terms are used with the meaning as follows:

As used herein, the term "human growth hormone (hGH)" refers all hGH polypeptides, preferably from mammalian species, more preferably from human and mammalian species, more preferably from human and murine species, as well as their variants, analogs, orthologs, homologs, and derivatives and fragments thereof, that are characterized by promoting growth in the growing phase and in maintaining normal body composition, anabolism, and lipid metabolism. Preferably, the term "hGH" refers to the hGH polypeptide of SEQ ID NO:1 as well as its variants, homologs and derivatives exhibiting essentially the same biological activity, i.e. promoting growth in the growing phase and in maintaining normal body composition, anabolism, and lipid metabolism. More preferably, the term "hGH" refers to the polypeptide of SEQ ID NO:1.

SEQ ID NO:1 has the following sequence:

FPTIPLSRLFDNAMLRAHRLHQLAFDTYQEFEEAYIPKEQKYSFLQNPQTS

LCFSESIPTPSNREETQQKSNLELLRISLLLIQSWLEPVQFLRSVFANSLV

YGASDSNVYDLLKDLEEGIQTLMGRLEDGSPRTGQIFKQTYSKFDTNSHND

DALLKNYGLLYCFRKDMDKVETFLRIVQCRSVEGSCGF

As used herein, the term "hGH polypeptide variant" refers to a polypeptide from the same species that differs from a reference hGH polypeptide. Preferably, such reference hGH polypeptide sequence is the sequence of SEQ ID NO: 1. Generally, differences are limited so that the amino acid sequence of the reference and the variant are closely similar overall and, in many regions, identical. Preferably, hGH polypeptide variants are at least 70%, 80%, 90%, 95%, 96%, 97%, 98% or 99% identical to a reference hGH polypeptide, preferably the hGH polypeptide of SEQ ID NO:1. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:1.

Such hGH polypeptide variants may be naturally occurring variants, such as naturally occurring allelic variants encoded by one of several alternate forms of a hGH occupying a given locus on a chromosome or an organism, or isoforms encoded by naturally occurring splice variants originating from a single primary transcript. Alternatively, a hGH polypeptide variant may be a variant that is not known to occur naturally and that can be made mutagenesis techniques known in the art.

It is known in the art that one or more amino acids may be deleted from the N-terminus or C-terminus of a bioactive peptide or protein without substantial loss of biological function.

It is also recognized by one of ordinary skill in the art that some amino acid sequences of hGH polypeptides can be varied without significant effect of the structure or function of the protein. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term hGH polypeptide also encompasses all hGH polypeptides encoded by hGH analogs, orthologs, and/or species homologs. As used herein, the term "hGH analog" refers to hGH of different and unrelated organisms which perform the same functions in each organism but which did not originate from an ancestral structure that the organisms' ancestors had in common. Instead, analogous hGHs arose separately and then later evolved to perform the same or similar functions. In other words, analogous hGH polypeptides are polypeptides with quite different amino acid sequences but that perform the same biological activity, namely promoting growth in the growing phase and maintaining normal body composition, anabolism, and lipid metabolism.

As used herein the term "hGH ortholog" refers to hGH within two different species which sequences are related to each other via a common homologous hGH in an ancestral species, but which have evolved to become different from each other.

As used herein, the term "hGH homolog" refers to hGH of different organisms which perform the same functions in each organism and which originate from an ancestral structure that the organisms' ancestors had in common. In other words, homologous hGH polypeptides are polypeptides with quite similar amino acid sequences that perform the same biological activity, namely promoting growth in the growing phase and maintaining normal body composition, anabolism, and lipid metabolism. Preferably, hGH polypeptide homologs may be defined as polypeptides exhibiting at least 40%, 50%, 60%, 70%, 80%, 90%, 95%, 96%, 97%, 98% or 99% identity to a reference hGH polypeptide, preferably the hGH polypeptide of SEQ ID NO:1.

Thus, a hGH polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the hGH polypeptide is fused with another compound, such as a compound to increase the half-life of the polypeptide (for example, polyethylene glycol); and/or (iv) one in which additional amino acids are fused to the hGH polypeptide, such as an IgG Fc fusion region peptide or leader or secretory sequence or a sequence which is employed for purification of the above form of the polypeptide or a pre-protein sequence.

The hGH polypeptide may be a monomer or multimer. Multimers may be dimers, trimers, tetramers or multimers comprising at least five monomeric polypeptide units. Multimers may also be homodimers or heterodimers. Multimers of the invention may be the result of hydrophobic, hydrophilic, ionic and/or covalent association and/or may be indirectly linked, by for example, liposome formation. Preferably, the hGH polypeptide is a monomer.

As used herein, the term "hGH polypeptide fragment" refers to any peptide or polypeptide comprising a contiguous span of a part of the amino acid sequence of a hGH polypeptide, preferably the polypeptide of SEQ ID NO:1.

More specifically, a hGH polypeptide fragment comprises at least 6, preferably at least 8 or 10, more preferably at least 12, 15, 20, 25, 30, 35, 40, 50, 60, 75, 100, 125, 150, 175, 191 consecutive amino acids of a hGH polypeptide, more preferably of the polypeptide of SEQ ID NO:1. A hGH polypeptide fragment may additionally be described as subgenuses of hGH polypeptides comprising at least 6 amino acids, wherein "at least 6" is defined as any integer between 6 and the integer representing the C-terminal amino acid of a hGH polypeptide, preferably of the polypeptide of SEQ ID No:1. Further included are species of hGH polypeptide fragments at least 6 amino acids in length, as described above, that are further specified in terms of their N-terminal and C-terminal positions. Also encompassed by the term "hGH polypeptide fragment" as individual species are all hGH polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a hGH polypeptide, preferably the hGH polypeptide of SEQ ID:NO 1, is included in the present invention.

It is noted that the above species of polypeptide fragments may alternatively be described by the formula "a to b"; where "a" equals the N-terminal most amino acid position and "b" equals the C-terminal most amino acid position in the polynucleotide; and further where "a" equals an integer between 1 and the number of amino acids of a hGH polypeptide sequence minus 6, and where "b" equals an integer between 7 and the number of amino acids of the hGH polypeptide sequence; and where "a" is an integer smaller then "b" by at least 6, preferably of the hGH polypeptide sequence of SEQ ID NO:1.

As used herein the term "long-acting growth hormone" or "long-acting growth hormone compound" refers to a compound which comprises hGH either in crystallized form or wherein the hGH is embedded, fused or conjugated to at least one other chemical compound or moiety, such as for example a polymer or fatty acid-derived moiety, and has an increased retention time in a patient's body compared to unmodified hGH. Accordingly, a "long-acting growth hormone formulation" is a pharmaceutical formulation comprising a long-acting growth hormone.

The terms "long-acting growth hormone formulation" and "pharmaceutical formulation comprising a long-acting growth hormone" are used synonymously.

As used herein the term "prodrug" refers to a biologically active moiety reversibly and covalently connected to a specialized protective group through a reversible prodrug linker moiety comprising a reversible linkage with the biologically active moiety to alter or to eliminate undesirable properties in the parent molecule. This also includes the enhancement of desirable properties in the drug and the suppression of undesirable properties. The specialized non-toxic protective group is referred to as "carrier". A prodrug releases the reversibly and covalently bound biologically active moiety in the form of its corresponding drug. In other words, a prodrug comprises the three elements biologically active moiety, reversible prodrug linker and carrier, wherein the biologically active moiety is reversibly and covalently conjugated to the reversible prodrug linker and wherein the reversible prodrug linker is covalently conjugated to the carrier. Preferably, the linkage between the reversible prodrug linker and the carrier is a stable linkage. Preferably, the carrier is a polymer or fatty acid.

As used herein the terms "growth hormone equivalent" and "hGH equivalent" refer to the total mass of hGH or hGH moieties comprised in a long-acting growth hormone compound. In other words, if the long-acting growth hormone compound is for example a prodrug in which the hGH moiety is reversibly conjugated to a polymer the term "growth hormone equivalent" refers to the total mass of hGH moieties, but not to the total mass of hGH prodrug. If the long-acting growth hormone compound is for example a fusion protein in which the hGH moiety is fused with an natural or unnatural amino acid sequence the term "growth hormone equivalent" refers to the total mass of hGH moieties, but not to the total mass of the fusion protein.

The terms "formulation", "composition", "pharmaceutical formulation" and "pharmaceutical composition" refer to one or more active ingredients, such as a long-acting growth hormone, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the long-acting growth hormone formulations used in the bracketed dosage regimen of the present invention encompass any formulation made by admixing the long-acting growth hormone compound and one or more pharmaceutically acceptable excipient(s).

As used herein the term "liquid formulation" means a liquid formulation comprising long-acting hGH and at least one solvent. A preferred solvent is water.

As used herein the term "dry formulation" means that the long-acting acting growth hormone is provided in dry form. Suitable methods for drying are spray-drying and lyophilization which is also referred to as freeze-drying. Such dry formulation has a residual water content of a maximum of 10%, preferably less than 5% and more preferably less than 2% which residual water content is determined according to Karl Fischer. The preferred method of drying is lyophilization. "Lyophilized formulation" means that the dry formulation was first frozen and subsequently subjected to water reduction by means of reduced pressure. This terminology does not exclude additional drying steps which may occur in the manufacturing process prior to filling the formulation into the final container.

As used herein the term "reconstituted formulation" means the result of adding a solvent which is also referred to as "reconstitution solution" to a dry formulation. Preferably, the amount of solvent is such that the dry formulation is completely dissolved in the resulting reconstituted formulation.

As used herein the term "stable" means that within the indicated storage time only low amounts of hGH-related impurities, such as ASP130 succinimide and isoaspartate formation, ASN149 and ASN152 deamidation, and MET14 oxidation, were formed. Impurities may be quantified as tryptic peptides based on their respective peak area relative to the peak area of the corresponding unmodified tryptic peptide and "low amounts" correspond to an occurrence of such impurity to an extent of not greater than 20%, preferably not greater than 10%, even more preferably not greater than 5%, even more preferably not greater than 4%, even more preferably not greater than 3% (per impurity). It is understood that the locations of the specific amino acids prone to modification mentioned above correspond to hGH of SEQ ID:NO 1 and may vary in the case of, for example, fusion proteins or truncated proteins. To be considered stable, the composition contains less than 5% of the drug in its free form where applicable, such as, for example, in the case of a hGH prodrug.

As used herein, the term "fixed dosage regimen" refers to a dosage regimen in which the amount of drug to be administered to a patient in need thereof is determined by multiplying the weight of the patient with a predetermined factor. This is the commonly used dosage regimen for the treatment of growth hormone deficiency.

As used herein, the terms "bracketed dosage" and "bracketed dosage regimen" refer to a dosage regimen in which a range of patients' weights is allocated a particular dose of drug, in particular of long-acting growth hormone formulation and hGH equivalents. In other words, the dose a patient receives measured in mg hGH equivalents per week remains constant over a certain weight range, and wherein the dosage increases occur in a step-wise manner. If a patient's weight exceeds the weight of a particular weight range, which weight range is also referred to as weight "bracket" herein, the dose to be administered to said patient is increased to the next dosage step. In a bracketed dosage regimen a patient's weight is used for the allocation to a particular weight bracket, but the actual amount of hGH equivalents administered is the same for all patients within that weight bracket.

As used herein, the term "patient" refers to a mammal in need of treatment, preferably to a human. In one embodiment the patient is a child, also referred to as paediatric patient. In another embodiment the patient is an adult, also referred to as adult patient. In a third embodiment the patient is either a child or an adult.

As used herein the term "unit dosage" refers to the amount of drug, in particular of long-acting growth hormone formulation, which constitutes one dose, i.e. the amount of drug, in particular long-acting growth hormone formulation, which corresponds to one administration.

As used herein the term "unit dosage form" refers to a presentation of a unit dosage, i.e. refers to any application device comprising a unit dose of drug, in particular of long-acting growth hormone formulation. A preferred application device is selected from the group consisting of a syringe with needle, injection pen, autoinjector pen, needle-free injector, electronic injector and dual chamber cartridge.

As used herein the term "waste" refers to the difference between the advertised or nominal content of the presentation and the delivered dose.

As used herein the term "efficacy" refers to the height velocity achieved in naïve growth hormone children over a certain time period with a certain dosage regimen, in particular bracketed dosing, compared to the height velocity achieved with the treatment of naïve growth hormone children with a conventional fixed weight based dosing of appropriate daily growth hormone over the same time period. If the height velocity achieved over a certain time period in these two treatments varies by less than 20%, preferably by less than 15% and most preferably by less than 10%, the two dosage regimens are referred to as having the same efficacy. A preferred time period for measuring height velocity is one year, which can be determined by either measuring the increase in a patient's height over a full year period or by measuring for a fraction of one year (e.g. for 3, 4, 6, 8 or 9 months) and extrapolating the value to one full year, also referred to as "annualized height velocity".

As used herein, a "pharmaceutically effective dose" refers to that amount of growth hormone or growth hormone equivalent sufficient to treat growth hormone deficiency.

As used herein the term "about" in combination with a numerical value is used to indicate a range ranging from and including the numerical value plus and minus no more than 10%, more preferably no more than 8%, even more preferably no more than 5% and most preferably no more than 2%. For example, the phrase "about 20%" is used to mean a range ranging from and including 20%+/−10%, preferably 20%+/−8%, even more preferably 20%+/−5% and most preferably 20%+/−2%.

As used herein, the term "excipient" refers to a diluent, adjuvant, or vehicle with which the therapeutic is administered.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity. Hydrogels exhibit a thermodynamic compatibility with water which allows them to swell in aqueous media.

As used herein, the term "functional group" means a group of atoms which can react with other functional groups. Functional groups include but are not limited to the following groups: carboxylic acid (—(C=O)OH), primary or secondary amine (—NH$_2$, —NH—), maleimide, thiol (—SH), sulfonic acid (—(O=S=O)OH), carbonate, carbamate (—O(C=O)N<), hydroxy (—OH), aldehyde (—(C=O)H), ketone (—(C=O)—), hydrazine (>N—N<), isocyanate, isothiocyanate, phosphoric acid (—O(P=O)OHOH), phosphonic acid (—O(P=O)OHH), haloacetyl, alkyl halide, acryloyl, aryl fluoride, hydroxylamine, disulfide, vinyl sulfone, vinyl ketone, diazoalkane, oxirane, and aziridine.

As used herein, the term "moiety" means a part of a molecule, which lacks at least one atom compared to the corresponding reagent. If, for example, a reagent of the formula "H—X—H" reacts with another reagent and becomes part of the reaction product, the corresponding moiety of the reaction product has the structure "H—X—" or "—X—", whereas each "—" indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety "—C(O)N(R)—" can be attached to two moieties or interrupting a moiety either as "—C(O)N(R)—" or as "—N(R)C(O)—". Similarly, a moiety

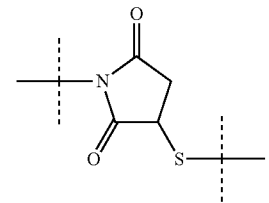

can be attached to two moieties or can interrupt a moiety either as

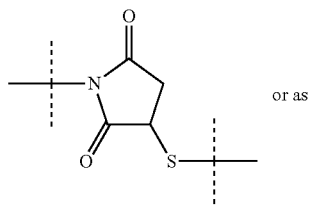

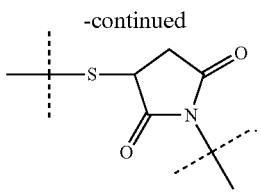

In case the long-acting growth hormone comprises one or more acidic or basic groups, the invention also comprises their corresponding pharmaceutically or toxicologically acceptable salts, in particular their pharmaceutically utilizable salts. Thus, the long-acting growth hormone which comprises acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Long-acting growth hormone which comprises one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the long-acting growth hormone simultaneously comprises acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of long-acting growth hormone, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMA (Europe) and/or the FDA (US) and/or any other national regulatory agency for use in animals, preferably in humans.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical group(s) and/or moiety/moieties, such as, for example, one or more functional group(s). Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as crosslinked hydrogels, no meaningful molecular weight ranges can be provided.

Preferably, a polymer comprises 2-methacryloyl-oxyethyl phosphoyl cholins, poly(acrylic acids), poly(acrylates), poly (acrylamides), poly(alkyloxy) polymers, poly(amides), poly (amidoamines), poly(amino acids), poly(anhydrides), poly (aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly (lactic-co-glycolic acids), poly(methacrylamides), poly (methacrylates), poly(methyloxazolines), poly (organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids or derivatives, functionalized hyaluronic acids, mannans, pectins, rhamnogalacturonans, starches, hydroxyalkyl starches, hydroxyethyl starches or other carbohydrate-based polymers, xylans, or copolymers thereof.

As used herein, the term "polymeric" means a reagent or a moiety comprising one or more polymer(s).

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers. As used herein, the term "number average molecular weight" means the ordinary arithmetic means of the molecular weights of the individual polymers.

As used herein, the term "PEG-based comprising at least X % PEG" in relation to a moiety or reagent means that said moiety or reagent comprises at least X % (w/w) ethylene glycol units (—CH$_2$CH$_2$O—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

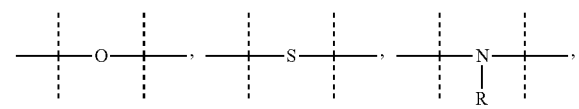

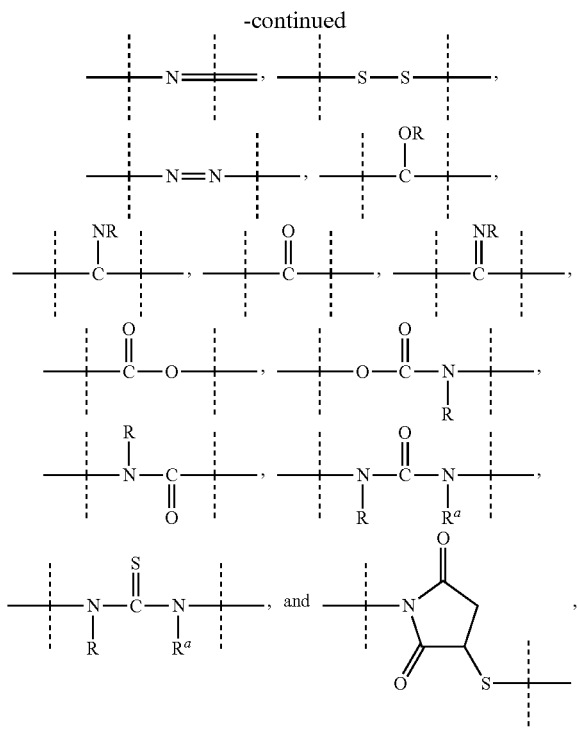

wherein
dashed lines indicate attachment to the remainder of the moiety or reagent, and
R and $R^a$ are independently of each other selected from the group consisting of H, methyl, ethyl, propyl, butyl, pentyl and hexyl.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

R$^{x1}$, R$^{x1a}$, R$^{x1b}$ are independently of each other selected from the group consisting of —H, -T$^0$, C$_{1-50}$ alkyl, C$_{2-50}$ alkenyl, and C$_{2-50}$ alkynyl; wherein -T$^0$, C$_{1-50}$ alkyl, C$_{2-50}$ alkenyl, and C$_{2-50}$ alkynyl are optionally substituted with one or more R$^{x2}$, which are the same or different and wherein C$_{1-50}$ alkyl, C$_{2-50}$ alkenyl, and C$_{2-50}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—; —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different;

each R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each R$^{x3}$, R$^{x3a}$, R$^{x4}$, R$^{x4a}$, R$^{x4b}$ is independently selected from the group consisting of —H and C$_{1-6}$ alkyl; wherein C$_{1-6}$ alkyl is optionally substituted with one or more halogen, which are the same or different.

More preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$ N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1}$R$^{x1a}$), -T$^0$, C$_{1-10}$ alkyl, C$_{2-10}$ alkenyl, and C$_{2-10}$ alkynyl; wherein -T$^0$, C$_{1-10}$ alkyl, C$_{2-10}$ alkenyl, and C$_{2-10}$ alkynyl are optionally substituted with one or more R$^{x2}$, which are the same or different and wherein C$_{1-10}$ alkyl, C$_{2-10}$ alkenyl, and C$_{2-10}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each R$^{x1}$, R$^{x1a}$, R$^{x1b}$, R$^{x3}$, R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different;

each R$^{x2}$ is independently selected from the group consisting of halogen, —CN, oxo (=O), —COOR$^{x4}$, —OR$^{x4}$, —C(O)R$^{x4}$, —C(O)N(R$^{x4}$R$^{x4a}$), —S(O)$_2$N(R$^{x4}$R$^{x4a}$), —S(O)N(R$^{x4}$R$^{x4a}$), —S(O)$_2$R$^{x4}$, —S(O)R$^{x4}$, —N(R$^{x4}$)S(O)$_2$N(R$^{x4a}$R$^{x4b}$), —SR$^{x4}$, —N(R$^{x4}$R$^{x4a}$), —NO$_2$, —OC(O)R$^{x4}$, —N(R$^{x4}$)C(O)R$^{x4a}$, —N(R$^{x4}$)S(O)$_2$R$^{x4a}$, —N(R$^{x4}$)S(O)R$^{x4a}$, —N(R$^{x4}$)C(O)OR$^{x4a}$, —N(R$^{x4}$)C(O)N(R$^{x4a}$R$^{x4b}$), —OC(O)N(R$^{x4}$R$^{x4a}$), and C$_{1-6}$ alkyl; wherein C$_{1-6}$ alkyl is optionally substituted with one or more halogen, which are the same or different;

each R$^{x4}$, R$^{x4a}$, R$^{x4b}$ is independently selected from the group consisting of —H, halogen, C$_{1-6}$ alkyl, C$_{2-6}$ alkenyl, and C$_{2-6}$ alkynyl;

Even more preferably, the one or more further optional substituents are independently of each other selected from the group consisting of halogen, —CN, —COOR$^{x1}$, —OR$^{x1}$, —C(O)R$^{x1}$, —C(O)N(R$^{x1}$R$^{x1a}$), —S(O)$_2$N(R$^{x1}$R$^{x1a}$), —S(O)N(R$^{x1}$R$^{x1a}$), —S(O)$_2$R$^{x1}$, —S(O)R$^{x1}$, —N(R$^{x1}$)S(O)$_2$N(R$^{x1a}$R$^{x1b}$), —SR$^{x1}$, —N(R$^{x1}$R$^{x1a}$), —NO$_2$, —OC(O)R$^{x1}$, —N(R$^{x1}$)C(O)R$^{x1a}$, —N(R$^{x1}$)S(O)$_2$R$^{x1a}$, —N(R$^{x1}$)S(O)R$^{x1a}$, —N(R$^{x1}$)C(O)OR$^{x1a}$, —N(R$^{x1}$)C(O)N(R$^{x1a}$R$^{x1b}$), —OC(O)N(R$^{x1a}$R$^{x1a}$), -T$^0$, C$_{1-6}$ alkyl, C$_{2-6}$ alkenyl, and C$_{2-6}$ alkynyl; wherein -T$^0$, C$_{1-6}$ alkyl, C$_{2-6}$ alkenyl, and C$_{2-6}$ alkynyl are optionally substituted with one or more R$^{x2}$, which are the same or different and wherein C$_{1-6}$ alkyl, C$_{2-6}$ alkenyl, and C$_{2-6}$ alkynyl are optionally interrupted by one or more groups selected from the group consisting of -T$^0$-, —C(O)O—, —O—, —C(O)—, —C(O)N(R$^{x3}$)—, —S(O)$_2$N(R$^{x3}$)—, —S(O)N(R$^{x3}$)—, —S(O)$_2$—, —S(O)—, —N(R$^{x3}$)S(O)$_2$N(R$^{x3a}$)—, —S—, —N(R$^{x3}$)—, —OC(OR$^{x3}$)(R$^{x3a}$)—, —N(R$^{x3}$)C(O)N(R$^{x3a}$)—, and —OC(O)N(R$^{x3}$)—;

each R$^{x1}$, R$^{x1a}$, R$^{x1b}$, R$^{x2}$, R$^{x3}$, R$^{x3a}$ is independently selected from the group consisting of —H, halogen, C$_{1-6}$ alkyl, C$_{2-6}$ alkenyl, and C$_{2-6}$ alkynyl;

each T$^0$ is independently selected from the group consisting of phenyl, naphthyl, indenyl, indanyl, tetralinyl, C$_{3-10}$ cycloalkyl, 3- to 10-membered heterocyclyl, and 8- to 11-membered heterobicyclyl; wherein each T$^0$ is independently optionally substituted with one or more R$^{x2}$, which are the same or different.

Preferably, a maximum of 6 —H atoms of an optionally substituted molecule or moiety are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "spacer" as used herein refers preferably to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —N(R$^{z1}$)—, —OC(OR$^{z1}$)(R$^{z1a}$)—, —N(R$^{z1}$)C(O)N(R$^{z1a}$)—, —OC(O)N(R$^{z1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more R$^{z2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —S—, —N(R$^{z3}$)—, —OC(OR$^{z3}$)(R$^{z3a}$)—, —N(R$^{z3}$)C(O)N(R$^{z3a}$)—, and —OC(O)N(R$^{z3}$)—;

R$^{z1}$ and R$^{z1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more R$^{z2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{z4}$)—, —S(O)$_2$N(R$^{z4}$)—, —S(O)N(R$^{z4}$)—, —S(O)$_2$—, —S(O)—, —N(R$^{z4}$)S(O)$_2$N(R$^{z4a}$)—, —S—, —N(R$^{z4}$)—, —OC(OR$^{z4}$)(R$^{z4a}$)—, —N(R$^{z4}$)C(O)N(R$^{z4a}$)—, and —OC(O)N(R$^{z4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more R$^{z2}$, which are the same or different;

each R$^{z2}$ is independently selected from the group consisting of halogen, —CN, oxo (=O), —COOR$^{z5}$, —OR$^{z5}$, —C(O)R$^{z5}$, —C(O)N(R$^{z5}$R$^{z5a}$), —S(O)$_2$N(R$^{z5}$R$^{z5a}$), —S(O)N(R$^{z5}$R$^{z5a}$), —S(O)$_2$R$^{z5}$, —S(O)R$^{z5}$, —N(R$^{z5}$)S(O)$_2$N(R$^{z5a}$R$^{z5b}$), —SR$^{z5}$, —N(R$^{z5}$R$^{z5a}$), —NO$_2$, —OC(O)R$^{z5}$, —N(R$^{z5}$)C(O)R$^{z5a}$, —N(R$^{z5}$)S(O)$_2$R$^{z5a}$, —N(R$^{z5}$)S(O)R$^{z5a}$, —N(R$^{z5}$)C(O)OR$^{z5a}$, —N(R$^{z5}$)C(O)N(R$^{z5a}$R$^{z5b}$), —OC(O)N(R$^{z5}$R$^{z5a}$), and C$_{1-6}$ alkyl; wherein C$_{1-6}$ alkyl is optionally substituted with one or more halogen, which are the same or different;

each R$^{z3}$, R$^{z3a}$, R$^{z4}$, R$^{z4a}$, R$^{z5}$, R$^{z5a}$ and R$^{z5b}$ is independently selected from the group consisting of —H, and C$_{1-6}$ alkyl; wherein C$_{1-6}$ alkyl is optionally substituted with one or more halogen, which are the same or different.

More preferably, the term "spacer" refers to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —N(R$^{z1}$)—, —OC(OR$^{z1}$)(R$^{z1a}$)—, —N(R$^{z1}$)C(O)N(R$^{z1a}$)—, —OC(O)N(R$^{z1}$)—, C$_{1-50}$ alkyl, C$_{2-50}$ alkenyl, and C$_{2-50}$ alkynyl; wherein -T-, C$_{1-50}$ alkyl, C$_{2-50}$ alkenyl, and C$_{2-50}$ alkynyl are optionally substituted with one or more R$^{z2}$, which are the same or different and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —S—, —N(R$^{z3}$)—, —OC(OR$^{z3}$)(R$^{z3a}$)—, —N(R$^{z3}$)C(O)N(R$^{z3a}$)—, and —OC(O)N(R$^{z3}$)—;

R$^{z1}$ and R$^{z1a}$ are independently of each other selected from the group consisting of —H, -T, C$_{1-50}$ alkyl, C$_{2-50}$ alkenyl, and C$_{2-50}$ alkynyl; wherein -T, C$_{1-50}$ alkyl, C$_{2-50}$ alkenyl, and C$_{2-50}$ alkynyl are optionally substituted with one or more R$^{z2}$, which are the same or different, and wherein C$_{1-50}$ alkyl, C$_{2-50}$ alkenyl, and C$_{2-50}$ alkynyl are optionally interrupted by one or more groups selected from the group consisting of -T-, —C(O)O—, —O—, —C(O)—, —C(O)N(R$^{z4}$)—, —S(O)$_2$N(R$^{z4}$)—, —S(O)N(R$^{z4}$)—, —S(O)$_2$—, —S(O)—, —N(R$^{z4}$)S(O)$_2$N(R$^{z4a}$)—, —S—, —N(R$^{z4}$)—, —OC(OR$^{z4}$)(R$^{z4a}$)—, —N(R$^{z4}$)C(O)N(R$^{z4a}$)—, and —OC(O)N(R$^{z4}$)—;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more R$^{z2}$, which are the same or different;

each R$^{z2}$ is independently selected from the group consisting of halogen, —CN, oxo (=O), —COOR$^{z5}$, —OR$^{z5}$, —C(O)R$^{z5}$, —C(O)N(R$^{z5}$R$^{z5a}$), —S(O)$_2$N(R$^{z5}$R$^{z5a}$), —S(O)N(R$^{z5}$R$^{z5a}$), —S(O)$_2$R$^{z5}$, —S(O)R$^{z5}$, —N(R$^{z5}$)S(O)$_2$N(R$^{z5a}$R$^{z5b}$), —SR$^{z5}$, —N(R$^{z5}$R$^{z5a}$), —NO$_2$, —OC(O)R$^{z5}$, —N(R$^{z5}$)C(O)R$^{z5a}$, —N(R$^{z5}$)S(O)$_2$R$^{z5a}$, —N(R$^{z5}$)S(O)R$^{z5a}$, —N(R$^{z5}$)C(O)OR$^{z5a}$, —N(R$^{z5}$)C(O)N(R$^{z5a}$R$^{z5b}$), —OC(O)N(R$^{z5}$R$^{z5a}$), and C$_{1-6}$ alkyl; wherein C$_{1-6}$ alkyl is optionally substituted with one or more halogen, which are the same or different; and each R$^{z3}$, R$^{z3a}$, R$^{z4}$, R$^{z4a}$, R$^{z5}$, R$^{z5a}$ and R$^{z5b}$ is independently selected from the group consisting of —H, and C$_{1-6}$ alkyl, wherein C$_{1-6}$ alkyl is optionally substituted with one or more halogen, which are the same or different.

Even more preferably, the term "spacer" refers to a moiety selected from the group consisting of -T-, —C(O)O—, —O—, —C(O)—, —C(O)N(R$^{z1}$)—, —S(O)$_2$N(R$^{z1}$)—, —S(O)N(R$^{z1}$)—, —S(O)$_2$—, —S(O)—, —N(R$^{z1}$)S(O)$_2$N(R$^{z1a}$)—, —S—, —N(R$^{z1}$)—, —OC(OR$^{z1}$)(R$^{z1a}$)—, —N(R$^{z1}$)C(O)N(R$^{z1a}$)—, —OC(O)N(R$^{z1}$)—, C$_{1-50}$ alkyl, C$_{2-50}$ alkenyl, and C$_{2-50}$ alkynyl; wherein -T-, C$_{1-20}$ alkyl, C$_{2-20}$ alkenyl, and C$_{2-20}$ alkynyl are optionally substituted with one or more R$^{z2}$, which are the same or different and wherein C$_{1-20}$ alkyl, C$_{2-20}$ alkenyl, and C$_{2-20}$ alkynyl are optionally interrupted by one or more groups selected from the group consisting of -T-, —C(O)O—, —O—, —C(O)—, —C(O)N(R$^{z3}$)—, —S(O)$_2$N(R$^{z3}$)—, —S(O)N(R$^{z3}$)—, —S(O)$_2$—, —S(O)—, —N(R$^{z3}$)S(O)$_2$N(R$^{z3a}$)—, —S—, —N(R$^{z3}$)—, —OC(OR$^{z3}$)(R$^{z3a}$)—, —N(R$^{z3}$)C(O)N (R$^{z3a}$)—, and —OC(O)N(R$^{z3}$)—;

R$^{z1}$ and R$^{z1a}$ are independently selected from the group consisting of —H, -T, C$_{1-10}$ alkyl, C$_{2-10}$ alkenyl, and C$_{2-10}$ alkynyl;

each T is independently selected from the group consisting of phenyl, naphthyl, indenyl, indanyl, tetralinyl, C$_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each R$^{z2}$ is independently selected from the group consisting of halogen, and C$_{1-6}$ alkyl; and each R$^{z3}$, R$^{z3a}$, R$^{z4}$, R$^{z4a}$, R$^{z5}$, R$^{z5a}$ and R$^{z5b}$ is independently of each other selected from the group consisting of —H, and C$_{1-6}$ alkyl; wherein C$_{1-6}$ alkyl is optionally substituted with one or more halogen, which are the same or different.

The term "interrupted" means that a group of atoms is inserted into a moiety between two carbon atoms or—if the insertion is at one of the moiety's ends—between a carbon and a hydrogen atom. It is understood that if a moiety is interrupted by a group of atoms at one of its ends and if the moiety that is interrupted is connected to a second moiety, the interrupting group of atoms may also be so positioned that it is located between the last atom of said moiety and the first atom of the second moiety.

As used herein, the term "C$_{1-4}$ alkyl" alone or in combination means a straight-chain or branched alkyl moiety having 1 to 4 carbon atoms. If present at the end of a molecule, examples of straight-chain or branched C$_{1-4}$ alkyl are methyl, ethyl, n-propyl, isopropyl, n-butyl, isobutyl, sec-butyl and tert-butyl. When two moieties of a molecule are linked by the C$_{1-4}$ alkyl, then examples for such C$_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a C$_{1-4}$ alkyl carbon may optionally be replaced by a substituent as defined above. Optionally, a C$_{1-4}$ alkyl may be interrupted by one or more moieties as defined below.

As used herein, the term "C$_{1-6}$ alkyl" alone or in combination means a straight-chain or branched alkyl moiety having 1 to 6 carbon atoms. If present at the end of a molecule, examples of straight-chain and branched C$_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the C$_{1-6}$ alkyl group, then examples for such C$_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a C$_{1-6}$ carbon may optionally be replaced by a substituent as defined above. Optionally, a C$_{1-6}$ alkyl may be interrupted by one or more moieties as defined below.

Accordingly, "C$_{1-10}$ alkyl", "C$_{1-20}$ alkyl" or "C$_{1-50}$ alkyl" means an alkyl chain having 1 to 10, 1 to 20 or 1 to 50 carbon atoms, respectively, wherein each hydrogen atom of the C$_{1-10}$, C$_{1-20}$ or C$_{1-50}$ carbon may optionally be replaced by a substituent as defined above. Optionally, a C$_{1-10}$ or C$_{1-50}$ alkyl may be interrupted by one or more moieties as defined below.

As used herein, the term "C$_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the C$_{2-6}$ alkenyl group, then an example for such C$_{2-6}$ alkenyl is —CH=CH—. Each hydrogen atom of a C$_{2-6}$ alkenyl moiety may optionally be replaced by a substituent as defined above. Optionally, a C$_{2-6}$ alkenyl may be interrupted by one or more moieties as defined below.

Accordingly, the term "C$_{2-10}$ alkenyl", "C$_{2-20}$ alkenyl" or "C$_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a C$_{2-10}$ alkenyl, C$_{2-20}$ alkenyl or C$_{2-50}$ alkenyl group may optionally be replaced by a substituent as defined above. Optionally, a C$_{2-10}$ alkenyl, C$_{2-20}$ alkenyl or C$_{2-50}$ alkenyl may be interrupted by one or more moieties as defined below.

As used herein, the term "C$_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a C$_{2-6}$ alkynyl group may optionally be replaced by a substituent as defined above. Optionally, one or more double bond(s) may occur. Optionally, a C$_{2-6}$ alkynyl may be interrupted by one or more moieties as defined below.

Accordingly, as used herein, the term "C$_{2-10}$ alkynyl", "C$_{2-20}$ alkynyl" and "C$_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a C$_{2-10}$ alkynyl, C$_{2-20}$ alkynyl or C$_{2-50}$ alkynyl group may optionally be replaced by a substituent as defined above. Optionally, one or more double bond(s) may occur. Optionally, a C$_{2-10}$ alkynyl, C$_{2-20}$ alkynyl or C$_{2-50}$ alkynyl may be interrupted by one or more moieties as defined below.

As mentioned above, a C$_{1-4}$ alkyl, C$_{1-6}$ alkyl, C$_{1-10}$ alkyl, C$_{1-20}$ alkyl, C$_{1-50}$ alkyl, C$_{2-6}$ alkenyl, C$_{2-10}$ alkenyl, C$_{2-20}$ alkenyl, C$_{2-50}$ alkenyl, C$_{2-6}$ alkynyl, C$_{2-10}$ alkynyl, C$_{2-20}$ alkenyl or C$_{2-50}$ alkynyl may optionally be interrupted by one or more of the following moieties:

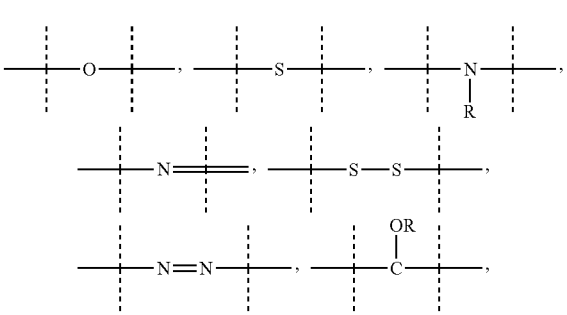

-continued

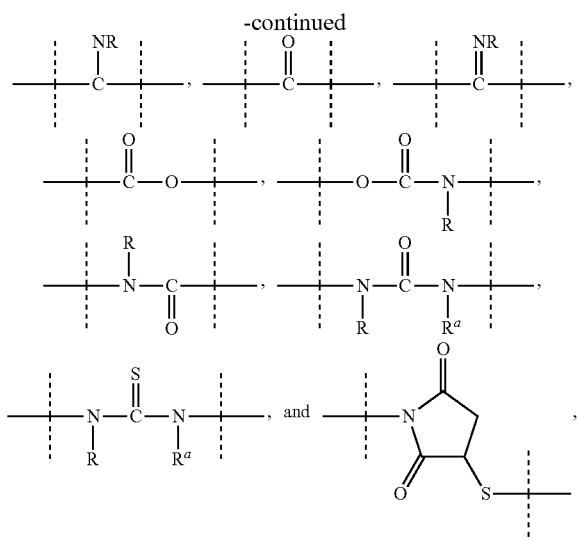

wherein
dashed lines indicate attachment to the remainder of the moiety or reagent; and
R and $R^a$ are independently of each other selected from the group consisting of H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may comprise up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may comprise up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may comprise up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term "8- to 30-membered heteropolycyclyl" or "8- to 30-membered heteropolycycle" means a heterocyclic moiety of more than two rings with 8 to 30 ring atoms, preferably of three, four or five rings, where two neighboring rings share at least one ring atom and that may comprise up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —S(O)$_2$—), oxygen and nitrogen (including =N(O)—) and wherein the ring is linked to the rest of a molecule via a carbon or nitrogen atom.

As used herein, "halogen" means fluoro, chloro, bromo or iodo. It is generally preferred that halogen is fluoro or chloro.

In general, the term "comprise" or "comprising" also encompasses "consist of" or "consisting of".

According to the present invention the long-acting growth hormone formulation is provided in a multitude of unit dosage forms with increasing amounts of growth hormone equivalents wherein the amount of growth hormone equivalents increases by at least 10% between one unit dosage form and the next higher dosage form, i.e. there is a sequential difference in drug content in said unit dosage forms of at least 10%. Preferably the increase in the amount of growth hormone equivalents ranges from 10 to 75% between one dosage form and the next higher dosage form, even more preferably from 12 to 50%, even more preferable from 15 to 40%, even more preferably from 18 to 30% and most preferably by about 20% as measured by hGH equivalents comprised in the long-acting growth hormone formulation. Accordingly, the dose of long-acting growth hormone formulation in two neighboring brackets differs by at least 10%, such as from 10 to 75%, even more preferably from 12 to 50%, even more preferably from 15 to 40%, even more preferably from 18 to 30% and most preferably by about 20% as measured by hGH equivalents comprised in the long-acting growth hormone formulation.

In a preferred embodiment all increases between one unit dosage form and the next higher dosage form comprised in the multitude of unit dosage forms is by a constant percentage value. Preferably, such constant percent value is a percent value selected from about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29% and about 30%. More preferably, such constant percent value is a percent value selected from 10%, 11%, 12%, 13%, 14%, 15%, 16%, 17%, 18%, 19%, 20%, 21%, 22%, 23%, 24%, 25%, 26%, 27%, 28%, 29% and 30%. Even more preferably, such constant percent value is a percent value selected from about 16%, about 17%, about 18%, about 19%, about 20%, about 21%, about 22%, about 23% and about 24%. Even more preferably, such constant percent value is a percent value selected from 16%, 17%, 18%, 19%, 20%, 21%, 22%, 23% and 24%. It is understood that values calculated from such constant value increase might be rounded to 3, 2, 1 or 0 position(s) after the decimal point. Accordingly, all increases in the dose of long-acting growth hormone formulation in two neighboring brackets is by a constant percentage value as measured by hGH equivalents comprised in the long-acting growth hormone formulation. Preferably, such constant percentage is selected from about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29% and about 30%. Even more preferably, such constant percent value is a percent value selected from about 16%, about 17%, about 18%, about 19%, about 20%, about 21%, about 22%, about 23% and about 24%. Even more preferably, such constant percent value is a percent value selected from 16%, 17%, 18%, 19%, 20%, 21%, 22%, 23% and 24%. It is understood that values calculated from such constant increase might be rounded to 3, 2, 1 or 0 position(s) after the decimal point.

In a preferred embodiment the increase between one dosage form and the next higher dosage form comprised in the multitude of dosage forms is by a constant percentage value which constant percentage value is about 20%. In another preferred embodiment the constant percentage value is about 18%. In another preferred embodiment the constant percentage value is about 22%. In another preferred embodiment the constant percentage value is about 25%. In another preferred embodiment the constant percentage value is about 30%. In another preferred embodiment the constant percentage value is about 35%. Accordingly, in a preferred embodiment all increases between one bracket and the next higher bracket is by a constant percentage value which constant percentage value is about 20%. In another preferred embodiment the constant percentage value is about 18%. In another preferred embodiment the constant percentage value is about 22%. In another preferred embodiment the constant percentage value is about 25%. In another preferred embodiment the constant percentage value is about 30%. In another preferred embodiment the constant percentage value is about 35%.

Preferably, the multitude of unit dosage forms comprises at least 2 unit dosage forms, such as at least 3 unit dosage forms, at least 4 unit dosage forms, at least 5 unit dosage forms. Preferably, the multitude of unit dosage forms consists of between 3 and 20 unit dosage forms, more preferably consists of between 5 and 18 unit dosage forms and even more preferably of between 6 and 14 unit dosage forms. In another embodiment the number of dosage forms ranges from 3 to 15. Preferably, the multitude of unit dosage forms consists of 3, 4, 5, 6, 7, 8, 9, 10, 11, 12, 13, 14, 15 or 16 unit dosage forms. In one embodiment the multitude of unit dosage forms consist of 8 unit dosage forms. In another embodiment the multitude of unit dosage forms consists of 9 unit dosage forms. In another embodiment the multitude of unit dosage forms consists of 10 unit dosage forms. In another embodiment the multitude of unit dosage forms consists of 11 unit dosage forms. Accordingly, all patients to be treated with the bracketed dosage regimen of the present invention are allocated to a total of at least 2 brackets, such as at least 3 brackets, at least 4 brackets, at least 5 brackets. Preferably, there are between 3 and 20 brackets in a bracketed dosage regimen, more preferably there are between 5 and 18 brackets in a bracketed dosage regimen and even more preferably there are between 6 and 14 brackets in a bracketed dosage regimen. In another embodiment the number of brackets ranges from 3 to 15 in a bracketed dosage regimen. Preferably, all patients to be treated with the bracketed dosage regimen of the present invention are allocated to 3, 4, 5, 6, 7, 8, 9, 10, 11, 12, 13, 14, 15 or 16 brackets. In another embodiment the total number of brackets is 9. In another embodiment the total number of brackets is 10. In another embodiment the total number of brackets is 11.

In one embodiment the unit dosage form is in the form of a syringe with needle. Accordingly, the long-acting growth hormone formulation administered in the bracketed dosage regimen of the present invention is comprised in a syringe with needle.

In another embodiment the unit dosage form is in the form of a prefilled syringe. Accordingly, the long-acting growth hormone formulation administered in the bracketed dosage regimen of the present invention is comprised in a prefilled syringe.

In another embodiment the unit dosage form is in the form of an injection pen which is also referred to as a pen injector. Accordingly, the long-acting growth hormone formulation administered in the bracketed dosage regimen of the present invention is comprised in an injection pen.

In another embodiment the unit dosage form is in the form of an autoinjector pen. Accordingly, the long-acting growth hormone formulation administered in the bracketed dosage regimen of the present invention is comprised in an autoinjector pen.

In another embodiment the unit dosage form is in the form of a needle-free injector. Accordingly, the long-acting growth hormone formulation administered in the bracketed dosage regimen of the present invention is comprised in a needle-free injector.

In another embodiment the unit dosage form is in the form of an electronic injector. Accordingly, the long-acting growth hormone formulation administered in the bracketed dosage regimen of the present invention is comprised in an electronic injector.

In another embodiment the unit dosage form is in the form of a dual chamber cartridge. Accordingly, the long-acting growth hormone formulation administered in the bracketed dosage regimen of the present invention is comprised in a dual chamber cartridge.

In one embodiment the dual chamber cartridge is suitable for use with a syringe. Accordingly, the dual chamber cartridge in which the long-acting growth hormone formulation administered in the bracketed dosage regimen of the present invention is comprised is suitable for use with a syringe.

In another embodiment the dual chamber cartridge is comprised in a syringe. Accordingly, the dual chamber cartridge in which the long-acting growth hormone formulation administered in the bracketed dosage regimen of the present invention is comprised is comprised in a syringe.

In another embodiment the dual chamber cartridge is suitable for use with a pen device or electronic injector. Accordingly, the dual chamber cartridge in which the long-acting growth hormone formulation administered in the bracketed dosage regimen of the present invention is comprised is suitable for use with a pen device or electronic injector.

In another embodiment the dual chamber cartridge is comprised in a pen device or electronic injector. Accordingly, the dual chamber cartridge in which the long-acting growth hormone formulation administered in the bracketed dosage regimen of the present invention is comprised is comprised in a pen device or electronic injector.

In another embodiment the unit dosage forms of the present invention are used in the treatment of growth hormone deficiency in a bracketed dosage regimen.

It is preferred that after administration of a pharmaceutically acceptable dose of the long-acting growth hormone formulation to a patient in need thereof less than 10% of the long-acting growth hormone formulation remains as waste in the unit dosage form of the present invention. More preferably, less than 9% remains in the unit dosage form, even more preferably less than 8% remains in the unit dosage form, even more preferably less than 7% remains in the unit dosage form, even more preferably less than 6% remains in the unit dosage form, even more preferably less than 5% remains in the unit dosage form, even more preferably less than 4% remains in the unit dosage form, even more preferably less than 3% remains in the unit dosage form, even more preferably less than 2% remain in the unit dosage form and most preferably less than 1% remains in the unit dosage form. Even more preferably, there is essentially no waste after administration of a pharmaceutically acceptable dose of the long-acting growth hormone formulation to a patient in need thereof. It is understood that no injection device is free of dead space and that long-acting growth hormone formulation stuck therein does not count as waste.

In one embodiment the long-acting growth hormone formulation comprises growth hormone embedded or encapsulated in a polymer or lipid-comprising matrix or vehicle. A preferred polymer matrix comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

A preferred polymer is selected from the group consisting of PEG, polylactid-co-glycolid (PLGA) and hyaluronic acid. Most preferably, the polymer is PEG.

In one embodiment the polymer matrix is a hydrogel comprising a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

A preferred hydrogel comprises a polymer selected from the group consisting of PEG, polylactid-co-glycolid (PLGA) and hyaluronic acid. Most preferably, the hydrogel is a PEG-based hydrogel.

In another embodiment the long-acting growth hormone formulation comprises crystalline growth hormone.

In another embodiment the long-acting growth hormone formulation comprises a growth hormone moiety fused to a natural or unnatural amino acid sequence. Preferred amino acid sequences are selected from the group consisting of carboxyl-terminal peptide of the chorionic gonadotropin as described in US 2012/0035101 which are herewith incorporated by reference; albumin; XTEN sequences as described in WO2011123813A2 which are herewith incorporated by reference; proline/alanine random coil sequences as described in WO2011/144756A1 which are herewith incorporated by reference; proline/alanine/serine random coil sequences as described in WO2008/155134 which are herewith incorporated by reference; and Fc fusion proteins.

Accordingly, one preferred long-acting growth hormone formulation comprises a hGH-CTP fusion protein. Another preferred long-acting growth hormone formulation comprises a hGH-XTEN fusion protein. Another preferred long-acting growth hormone formulation comprises a hGH-HSA fusion protein. Another preferred long-acting growth hormone formulation comprises a hGH-Fc fusion protein.

In another embodiment the long-acting growth hormone formulation comprises a chemically modified growth hormone or an analogue thereof, including PEGylated hGH and hGH modified with fatty acid derivatives. Preferred fatty acid derivatives are those disclosed in WO2005/027978A2 and WO2014/060512A1 which are herewith incorporated by reference.

Accordingly, a preferred long-acting growth hormone formulation comprises a hGH-fatty acid derivative conjugate.

In another embodiment the long-acting growth hormone formulation comprises a hGH prodrug, in which a hGH moiety is reversibly conjugated to a polymeric or fatty acid-derived moiety.

Preferably, the long-acting growth hormone formulation comprises a polymeric hGH prodrug as disclosed in WO05099768 A2 and WO 2009/133137 A2 which are herewith incorporated by reference. Accordingly, the long-acting growth hormone formulation preferably comprises a polymeric hGH prodrug of formula (Ia) or (Ib)

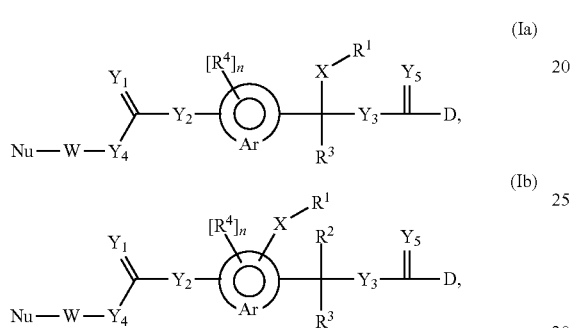

wherein
- -D is a hGH moiety connected to the rest of the molecule through an amine functional group;
- n is 0, 1, 2, 3, or 4;
- —X— is a chemical bond or a spacer;
- $=Y_1$ is selected from the group consisting of =O and =S;
- —$Y_2$— is selected from the group consisting of —O— and —S—;
- —$Y_3$—, —$Y_5$— are independently of each other selected from the group consisting of —O— and —S—;
- —$Y_4$— is selected from the group consisting of —O—, —$NR^5$— and —$C(R^6R^{6a})$—;
- —$R^1$ is a carrier, preferably a water-soluble PEG-based moiety comprising at least 40% PEG;
- —$R^2$, —$R^3$, —$R^5$, —$R^6$, —$R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
- —$R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;
- —W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, —C(O)N($R^7$)—, —O—, —S— and —N($R^7$)—;
- -Nu is a nucleophile selected from the group consisting of —N($R^7R^{7a}$), —N($R^7$OH), —N($R^7$)—N($R^{7a}R^{7b}$), —S($R^7$), —COOH,

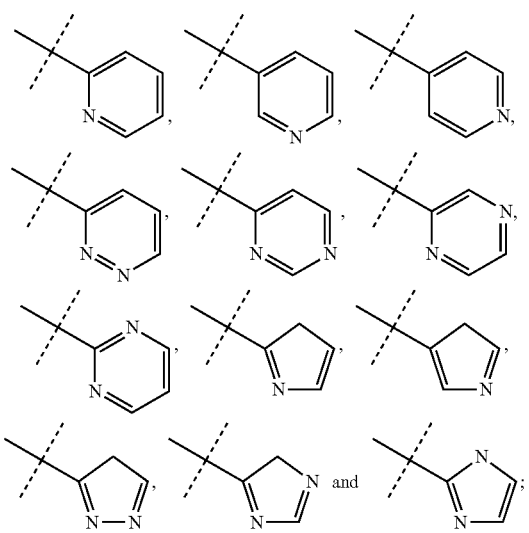

—Ar— is selected from the group consisting of

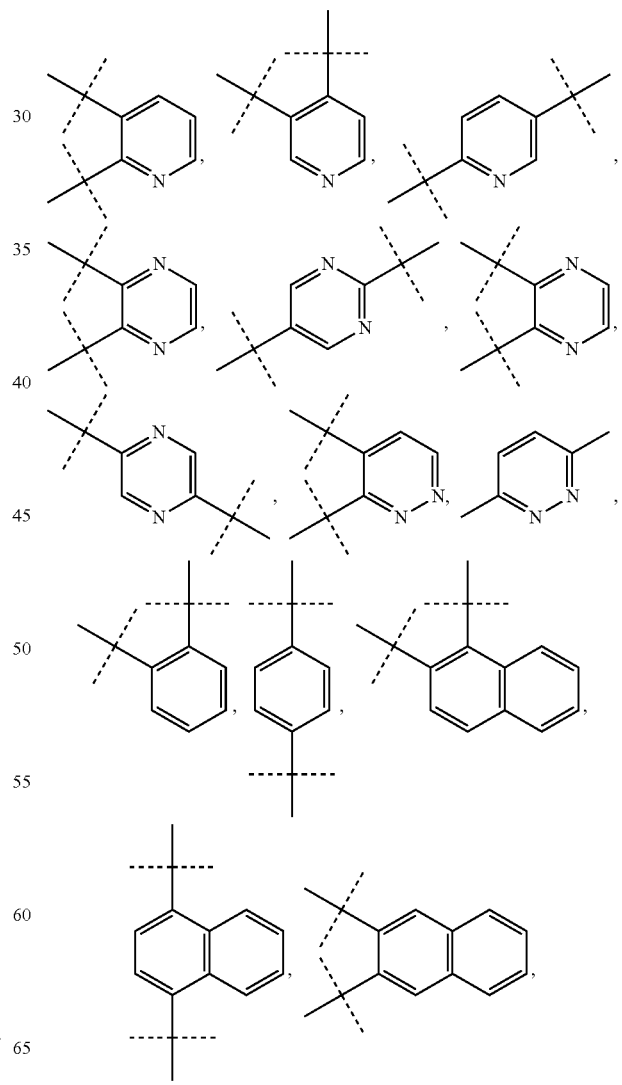

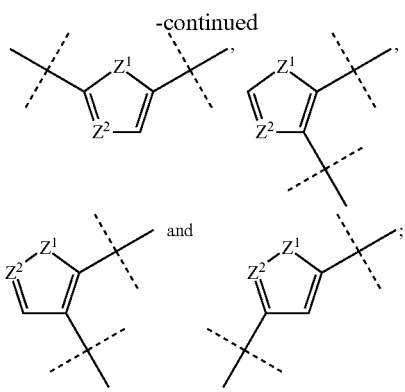

wherein
dashed lines indicate attachment to the rest of the prodrug,
—$Z^1$— is selected from the group consisting of —O—, —S— and —N($R^7$)—, and
—$Z^2$— is —N($R^7$)—; and
—$R^7$, —$R^{7a}$, —$R^{7b}$ are independently of each other selected from the group consisting of —H, $C_{1-6}$ alkyl, $C_{2-6}$ alkenyl and $C_{2-6}$ alkynyl;
wherein the prodrug of formula (Ia) and (Ib) is optionally further substituted.

In a preferred embodiment =$Y^1$ of formula (Ia) and (Ib) is =O.

In a preferred embodiment —$Y^2$— of formula (Ia) and (Ib) is —O—.

In a preferred embodiment —$Y^3$— of formula (Ia) and (Ib) is —O—.

In a preferred embodiment —$Y^4$— of formula (Ia) and (Ib) is —$NR^5$—.

In a preferred embodiment =$Y^5$ of formula (Ia) and (Ib) is =O.

In a preferred embodiment n of formula (Ia) and (Ib) is 0 or 1. Most preferably, n of formula (Ia) and (Ib) is 0.

Preferably, $R^1$ of formula (Ia) and (Ib) has a molecular weight ranging from 10 to 250 kDa, even more preferably from 15 to 150 kDa.

In one particularly preferred embodiment $R^1$ of formula (Ia) and (Ib) has a molecular weight ranging from 30 to 50 kDa, even more preferably from 35 to 45 kDa, even more preferably from 38 to 42 kDa and most preferably has a molecular weight of about 40 kDa.

In another equally preferred embodiment $R^1$ of formula (Ia) and (Ib) has a molecular weight ranging from 60 to 100 kDa, even more preferably from 70 to 90 kDa, even more preferably from 75 to 85 kDa and most preferably has a molecular weight of about 80 kDa.

Preferably, $R^1$ of formula (Ia) and (Ib) is branched and comprises at least three polymeric moieties which may also be referred to as polymeric arms or polymeric chains.

More preferably, $R^1$ of formula (Ia) and (Ib) comprises at least one branching point, preferably at least two branching points, and at least three polymeric chains which polymeric chains are preferably PEG-based, wherein each branching point is preferably selected from the group consisting of —N<, —$CR^8$< and >C<, wherein $R^8$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{10}$)—, —S(O)$_2$N($R^{10}$)—, —S(O)N($R^{10}$)—, —S(O)$_2$—, —S(O)—, —N($R^{10}$)S(O)$_2$N($R^{10a}$)—, —S—, —N($R^{10}$)—, —OC($OR^{10}$)($R^{10a}$)—, —N($R^{10}$)C(O)N($R^{10a}$)—, and —OC(O)N($R^{10}$)—; wherein $R^9$, $R^{10}$ and $R^{10a}$ are selected from —H, $C_{1-6}$ alkyl, $C_{2-6}$ alkenyl and $C_{2-6}$ alkynyl.

In one preferred embodiment $R^1$ of formula (Ia) and (Ib) comprises a first branching point $BP^1$ from which at least two moieties $C^1$ and $C^2$ extend of which at least one comprises an at least second branching point $BP^2$ from which at least two moieties $P^1$ and $P^2$ extend. More preferably, $R^1$ comprises a first branching point $BP^1$ from which two moieties $C^1$ and $C^2$ extend, which moiety $C^1$ comprises a branching point $BP^2$ from which at least two moieties $P^1$ and $P^2$ extend, and which moiety $C^2$ comprises a third branching point $BP^3$ from which at least two moieties $P^3$ and $P^4$ extend.

In another preferred embodiment $R^1$ comprises a moiety $C^1$ which comprises a first branching point $BP^1$, a second branching point $BP^2$ and a third branching point $BP^3$, wherein at least one moiety $P^1$ extends from $BP^1$, at least one moiety $P^2$ extends from $BP^2$ and at least one moiety $P^3$ extends from $BP^3$. More preferably, $R^1$ comprises a moiety $C^1$ which comprises a first branching point $BP^1$, a second branching point $BP^2$, a third branching point $BP^3$ and a forth branching point $BP^4$, wherein at least a moiety $P^1$ extends from $BP^1$, at least a moiety $P^2$ extends from $BP^2$, at least a moiety $P^3$ extends from $BP^3$ and at least a moiety $P^4$ extends from $BP^4$.

Preferably, $BP^1$, $BP^2$, $BP^3$ and $BP^4$ are independently of each other selected from —$CR^8$<, >C< and —N<, wherein $R^8$ is selected from —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{10}$)—, —S(O)$_2$N($R^{10}$)—, —S(O)N($R^{10}$)—, —S(O)$_2$—, —S(O)—, —N($R^{10}$)S(O)$_2$N($R^{10a}$)—, —S—, —N($R^{10}$)—, —OC($OR^{10}$)($R^{10a}$)—, —N($R^{10}$)C(O)N($R^{10a}$)—, and —OC(O)N($R^{10}$)—; wherein $R^9$, $R^{10}$ and $R^{10a}$ are selected from —H, $C_{1-6}$ alkyl, $C_{2-6}$ alkenyl and $C_{2-6}$ alkynyl.

Preferably, $C^1$ and $C^2$ are independently of other selected from $C_{1-50}$ alkyl, $C_{2-50}$ alkenyl and $C_{2-50}$ alkynyl; wherein $C_{1-50}$ alkyl, $C_{2-50}$ alkenyl and $C_{2-50}$ alkynyl are optionally substituted with one or more $R^{11}$, which are the same or different, and wherein $C_{1-50}$ alkyl, $C_{2-50}$ alkenyl and $C_{2-50}$ alkynyl are optionally interrupted with one or more groups selected from the group consisting of -T-, —C(O)O—, —O—, —C(O)—, —C(O)N($R^{12}$)—, —S(O)$_2$N($R^{12}$)—, —S(O)N($R^{12}$)—, —S(O)$_2$—, —S(O)—, —N($R^{12}$)S(O)$_2$N($R^{12a}$)—, —S—, —N($R^{12}$)—, —OC($OR^{12}$)($R^{12a}$)—, —N($R^{12}$)C(O)N($R^{12a}$)—, and —OC(O)N($R^{12}$)—;

wherein -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, and wherein each -T- is independently optionally substituted with one or more $R^{11}$, which are the same or different;

wherein each $R^{11}$ is independently selected from the group consisting of halogen, —CN, oxo (=O), —$COOR^{12}$, —$OR^{12}$, —C(O)$R^{12}$, —C(O)N($R^{12}R^{12a}$), —S(O)$_2$N($R^{12}R^{12a}$), —S(O)N($R^{12}R^{12a}$), —S(O)$_2R^{12}$, —S(O)$R^{12}$, —N($R^{12}$)S(O)$_2$N($R^{12a}R^{12b}$), —$SR^{12}$, —N($R^{12}R^{12a}$), —NO$_2$, —OC(O)$R^{12}$, —N($R^{12}$)C(O)$R^{12a}$, —N($R^{12}$)S(O)$_2R^{12a}$, —N($R^{12}$)S(O)$R^{12a}$, —N($R^{12}$)C(O)O$R^{12a}$, —N($R^{12}$)C(O)N($R^{12a}R^{12b}$), —OC(O)N($R^{12}R^{12a}$), and $C_{1-6}$ alkyl; wherein $C_{1-6}$ alkyl is optionally substituted with one or more halogen, which are the same or different;

and wherein each $R^{12}$, $R^{12a}$ and $R^{12b}$ are independently of each other selected from the group consisting of —H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl is optionally substituted with one or more halogen, which are the same or different.

Preferably, $P^1$, $P^2$, $P^3$, $P^4$ are independently of each other a polymeric moiety, more preferably a PEG-based chain comprising at least 40% PEG, even more preferably at least 50% PEG, even more preferably at least 60% PEG, even more preferably at least 70% PEG, even more preferably at least 80% PEG, even more preferably at least 90% PEG and most preferably at least 95% PEG.

In one preferred embodiment $P^1$, $P^2$, $P^3$ and $P^4$ have independently of each other a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment $P^1$, $P^2$, $P^3$ and $P^4$ have independently of each other a molecular weight ranging from 10 to 30 kDa, more preferably ranging from 15 to 25 kDa, even more preferably ranging from 17 to 23 kDa and most preferably have a molecular weight of about 20 kDa.

In a preferred embodiment —$R^1$ of formula (Ia) and (Ib) comprises a moiety of formula (II)

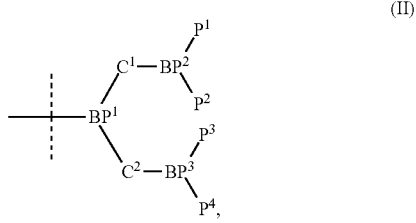

(II)

wherein
—$BP^1$<, —$BP^2$<, —$BP^3$< are independently of each other selected from the group consisting of —N< and —C($R^8$)<;
$R^8$ is selected from the group consisting of H, $C_{1-6}$ alkyl, $C_{2-6}$ alkenyl and $C_{2-6}$ alkynyl;
—$P^1$, —$P^2$, —$P^3$, —$P^4$ are independently of each other a PEG-based chain comprising at least 40% PEG and having a molecular weight ranging from 5 to 30 kDa;
—$C^1$—, —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{10}$)—, —S(O)$_2$N($R^{10}$)—, —S(O)N($R^{10}$)—, —S(O)$_2$—, —S(O)—, —N($R^{10}$)S(O)$_2$N($R^{10a}$)—, —S—, —N($R^{10}$)—, —OC(O$R^{10}$)($R^{10a}$)—, —N($R^{10}$)C(O)N($R^{10a}$)—, and —OC(O)N($R^{10}$)—;
each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;
each $R^9$ is independently selected from the group consisting of halogen, —CN, oxo (=O), —COO$R^{11}$, —O$R^{11}$, —C(O)$R^{11}$, —C(O)N($R^{11}R^{11a}$), —S(O)$_2$N($R^{11}R^{11a}$), —S(O)N($R^{11}R^{11a}$), —S(O)$_2R^{11}$, —S(O)$R^{11}$, —N($R^{11}$)S(O)$_2$N($R^{11a}R^{11b}$), —S$R^{11}$, —N($R^{11}R^{11a}$), —NO$_2$, —OC(O)$R^{11}$, —N($R^{11}$)C(O)$R^{11a}$, —N($R^{11}$)S(O)$_2R^{11a}$, —N($R^{11}$)S(O)$R^{11a}$, —N($R^{11}$)C(O)O$R^{11a}$, —N($R^{11}$)C(O)N($R^{11a}R^{11b}$), —OC(O)N($R^{11}R^{11a}$), and $C_{1-6}$ alkyl; wherein $C_{1-6}$ alkyl is optionally substituted with one or more halogen, which are the same or different; and
each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

In a preferred embodiment $BP^1$ of formula (II) is —N<.
In a preferred embodiment $BP^2$ and $BP^2$ of formula (II) are both —CH<.

It is advantageous if the first branching point $BP^1$ and the attachment site of X are separated by no more than a certain number of atoms.

Preferably, the critical distance in the prodrugs of formula (Ia) and (Ib) is less than 60 atoms, more preferably less than 50 atoms, even more preferably less than 40 atoms, even more preferably less than 30 atoms, even more preferably less than 20 atoms and most preferably less than 10 atoms.

The term "critical distance" refers to the shortest distance measured as the number of atoms between the first branching point $BP^1$ comprised in $R^1$ and the atom marked with the asterisk in formula (a), if the prodrug is of formula (Ia), or refers to the number of atoms between the first branching point $BP^1$ comprised in $R^1$ and the atom marked with the asterisk in formula (b), if the prodrug is of formula (Ib):

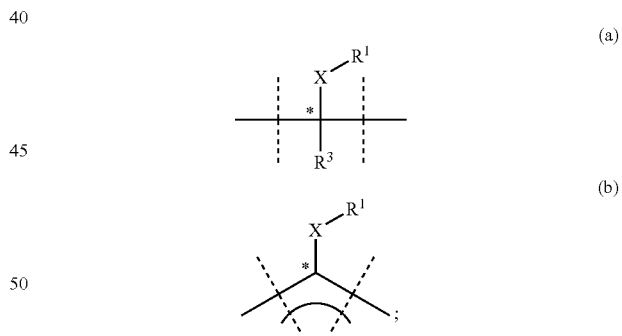

wherein the dashed lines indicate attachment to the remainder of the prodrug of formula (Ia) in the case of (a) and to the remainder of the prodrug of formula (Ib) in the case of (b).

In a preferred embodiment —$P^1$, —$P^2$, —$P^3$, —$P^4$ of formula (II) independently of each other have a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment —$P^1$, —$P^2$, —$P^3$, —$P^4$ of formula (II) independently of each other have a molecular weight ranging from 10 to 30 kDa, more preferably ranging from 15 to 25 kDa, even more preferably ranging from 17 to 23 kDa and most preferably have a molecular weight of about 20 kDa.

In a preferred embodiment $C^1$ and $C^2$ of formula (II) are $C_{1\text{-}50}$ alkyl interrupted by one or more of the groups selected from the group consisting of —O—, —C(O)N($R^{10}$)— and 3- to 10 membered heterocyclyl; wherein the 3- to 10 membered heterocyclyl is substituted with at least one oxo (=O).

Most preferably, $C^1$ and $C^2$ of formula (II) are of formula (IIa)

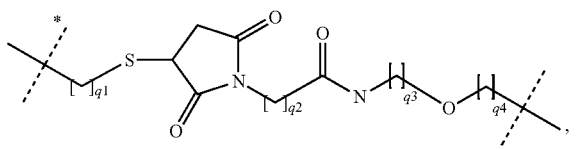

wherein the dashed line marked with the asterisk indicates attachment to $BP^1$;

the unmarked dashed line indicates attachment to $BP^2$ or $BP^3$, respectively;

q1 is 1, 2, 3, 4, 5, 6, 7 or 8; preferably q1 is 4, 5, 6, 7, or 8; more preferably q1 is 5, 6 or 7; most preferably q1 is 6;

q2 is 1, 2, 3, 4, or 5; preferably q2 is 1, 2 or 3; most preferably q2 is 2;

q3 is 1, 2, 3, 4, 5, 6, 7 or 8; preferably q3 is 2, 3, 4, or 5; more preferably q3 is 2, 3 or 4; most preferably q3 is 3;

q4 is 1, 2 or 3; most preferably, q4 is 1.

In a preferred embodiment $P^1$, $P^2$, $P^3$ and $P^4$ of formula (II) are independently of each other of formula (IIb)

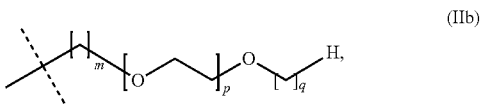

wherein the dashed line indicates attachment the remainder of $R^1$, i.e. to $BP^2$ or $BP^3$, respectively, m is 0 or 1, p is an integer ranging from 57 to 1420, more preferably 85 to 850; and q is selected from the group consisting of 1, 2, 3, 4, 5, and 6.

In a preferred embodiment p of formula (IIb) ranges from 170 to 284, even more preferably from 198 to 255 and most preferably from 215 to 238.

In an equally preferred embodiment p of formula (IIb) ranges from 340 to 568, even more preferably from 398 to 510 and most preferably from 426 to 482.

More preferably, —$R^1$ comprises a moiety of formula (IIc):

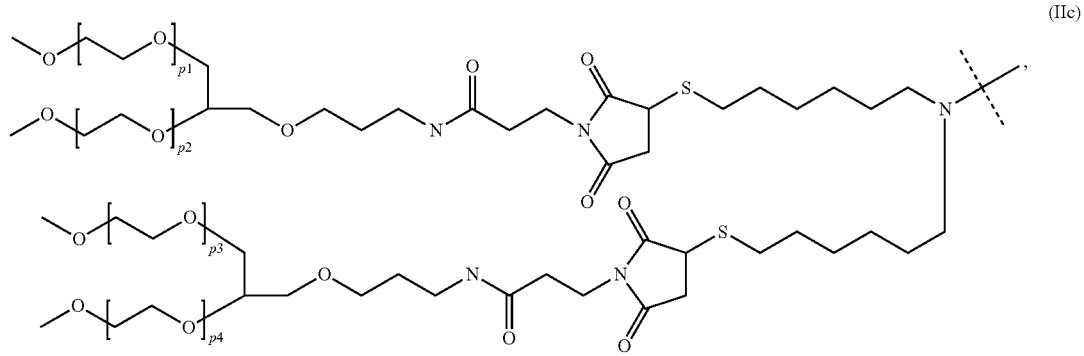

wherein
p1, p2, p3, p4 are independently an integer ranging from 57 to 1420, even more preferably from 85 to 850.

In a preferred embodiment p1, p2, p3 and p4 of formula (IIc) are an integer independently selected from 170 to 284, even more preferably from 198 to 255 and most preferably from 215 to 238.

In an equally preferred embodiment p1, p2, p3 and p4 of formula (IIc) are an integer independently selected from 340 to 568, even more preferably from 398 to 510 and most preferably from 426 to 482.

In a preferred embodiment $-R^2$ of formula (Ib) is selected from the group consisting of —H, methyl, ethyl, n-propyl, isopropyl, n-butyl, isobutyl, sec-butyl and tert-butyl. More preferably, $-R^2$ of formula (Ib) is selected from the group consisting of —H, methyl, ethyl, n-propyl and isopropyl. Even more preferably $-R^2$ of formula (Ib) is selected from —H, methyl and ethyl. Most preferably, $-R^2$ of formula (Ib) is —H.

In a preferred embodiment $-R^3$ of formula (Ia) and (Ib) is selected from the group consisting of —H, methyl, ethyl, n-propyl, isopropyl, n-butyl, isobutyl, sec-butyl and tert-butyl. More preferably, $-R^3$ of formula (Ia) and (Ib) is selected from the group consisting of —H, methyl, ethyl, n-propyl and isopropyl. Even more preferably $-R^3$ of formula (Ia) and (Ib) is selected from —H, methyl and ethyl. Most preferably, $-R^3$ of formula (Ia) and (Ib) is —H.

In a preferred embodiment, each $-R^4$ of formula (Ia) and (Ib) is independently selected from methyl, ethyl, n-propyl, isopropyl, n-butyl, isobutyl, sec-butyl and tert-butyl. More preferably, $-R^4$ of formula (Ia) and (Ib) is selected from the group consisting of methyl, ethyl, n-propyl and isopropyl. Even more preferably $-R^4$ of formula (Ia) and (Ib) is selected from methyl and ethyl.

In a preferred embodiment $-R^5$ of formula (Ia) and (Ib) is selected from the group consisting of —H, methyl, ethyl, n-propyl, isopropyl, n-butyl, isobutyl, sec-butyl and tert-butyl. More preferably, $-R^5$ of formula (Ia) and (Ib) is selected from the group consisting of —H, methyl, ethyl, n-propyl and isopropyl. Even more preferably $-R^5$ of formula (Ia) and (Ib) is selected from methyl and ethyl. Most preferably, $-R^5$ of formula (Ia) and (Ib) is methyl.

In a preferred embodiment $-R^6$ and $-R^{6a}$ of formula (Ia) and (Ib) are independently selected from the group consisting of —H, methyl, ethyl, n-propyl, isopropyl, n-butyl, isobutyl, sec-butyl and tert-butyl. More preferably, $-R^6$ and $-R^{6a}$ of formula (Ia) and (Ib) are independently selected from the group consisting of —H, methyl, ethyl, n-propyl and isopropyl. Even more preferably $-R^6$ and $-R^{6a}$ of formula (Ia) and (Ib) are independently selected from —H, methyl and ethyl. Most preferably, $-R^6$ and $-R^{6a}$ of formula (Ia) and (Ib) are both —H.

In a preferred embodiment X of formula (Ia) and (Ib) is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2$$R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2$$R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, X of formula (Ia) and (Ib) is selected from the group consisting of $C_{1-10}$ alkyl, $C_{2-10}$ alkenyl, and $C_{2-10}$ alkynyl; wherein $C_{1-10}$ alkyl, $C_{2-10}$ alkenyl, and $C_{2-10}$ alkynyl are optionally substituted with one or more $R^{z2}$, which are the same or different and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from $C_{1-6}$ alkyl, wherein $C_{1-6}$ alkyl is optionally substituted with one or more halogen, which are the same or different;

each $R^{z3}$, $R^{z3a}$ is independently selected from the group consisting of —H, and $C_{1-6}$ alkyl, wherein $C_{1-6}$ alkyl is optionally substituted with one or more halogen, which are the same or different.

Even more preferably, X of formula (Ia) and (Ib) is $C_{1-10}$ alkyl which is optionally interrupted by one or more groups selected from the group consisting of —C(O)O—, —O—, —C(O)—, —C(O)N($R^{z3}$)—, —S—, —N($R^{z3}$)—, —OC(O$R^{z3}$)($R^{z3a}$)— and —OC(O)N($R^{z3}$)—;

each $R^{z3}$, $R^{z3a}$ is independently selected from —H and $C_{1-6}$ alkyl.

Most preferably, X of formula (Ia) and (Ib) is of formula (III)

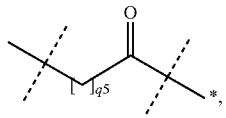

(III)

wherein
the dashed line marked with the asterisk indicates attachment to the $R^1$;
the unmarked dashed line indicates attachment to remainder of the prodrug;
q5 is 1, 2, 3, 4, 5, 6, 7 or 8; preferably q5 is 1, 2, 3, 4, or 5; more preferably q5 is 2, 3 or 4; most preferably q5 is 3;

Preferably, Ar of formula (Ia) and (Ib) is phenyl. Most preferably Ar of formula (Ia) and (Ib) is

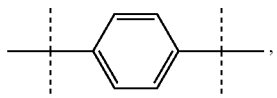

wherein the dashed lines indicate attachment to the remainder of the prodrug of formula (Ia) or (Ib).

Preferably W of formula (Ia) and (Ib) is $C_{1-20}$ alkyl, optionally interrupted with $C_{3-10}$ cycloalkyl, —C(O)—, —C(O)N($R^7$)—, —O—, —S— and —N($R^7$)—. Even more preferably, W of formula (Ia) and (Ib) is $C_{1-10}$ alkyl, optionally interrupted with $C_{3-10}$ cycloalkyl, —C(O)—, —C(O)N($R^7$)—, —O—, —S— and —N($R^7$)—. Even more preferably, W of formula (Ia) and (Ib) is $C_{1-6}$ alkyl, optionally interrupted with $C_{3-10}$ cycloalkyl, —C(O)—, —C(O)N($R^7$)—, —O—, —S— and —N($R^7$)—. Most preferably, W of formula (Ia) and (Ib) is

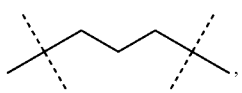

wherein
the dashed lines indicate attachment to the rest of the molecule.

Preferably, —Nu of formula (Ia) and (Ib) is —N($R^7 R^{7a}$).
Preferably, —$R^7$ and —$R^{7a}$ of formula (Ia) and (Ib) are independently of each other selected from the group consisting of —H, methyl, ethyl, n-propyl, isopropyl, n-butyl, isobutyl, sec-butyl and tert-butyl. More preferably, —$R^7$ and —$R^{7a}$ of formula (Ia) and (Ib) are independently of each other selected from —H, methyl, ethyl, n-propyl and isopropyl. Even more preferably, —$R^7$ and —$R^{7a}$ of formula (Ia) and (Ib) are independently of each other selected from methyl or ethyl. Most preferably, —$R^7$ and —$R^{7a}$ of formula (Ia) and (Ib) are both methyl.

Most preferably, the long-acting growth hormone formulation comprises a polymeric hGH prodrug of formula (IV)

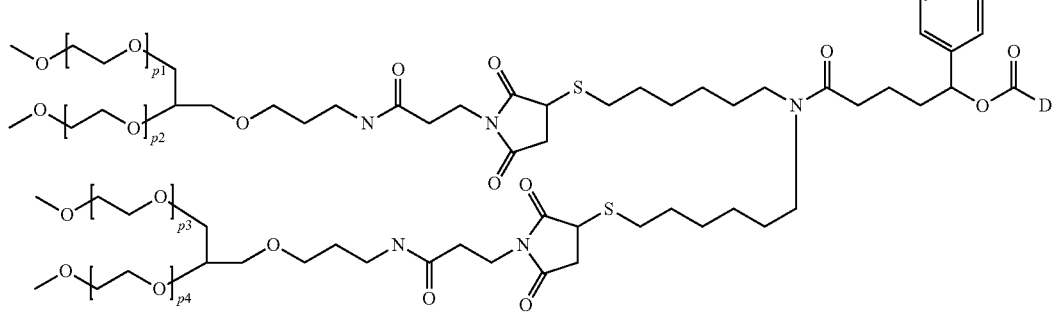

(IV)

wherein
D is a hGH moiety connected to the rest of the molecule through an amine functional group; and
p1, p2, p3, p4 are independently an integer ranging from 57 to 1420, even more preferably from 85 to 850.

In a preferred embodiment p1, p2, p3 and p4 of formula (IV) are an integer independently selected from 170 to 284, even more preferably from 198 to 255 and most preferably from 215 to 238.

In an equally preferred embodiment p1, p2, p3 and p4 of formula (IV) are an integer independently selected from 340 to 568, even more preferably from 398 to 510 and most preferably from 426 to 482.

If p1, p2, p3 and p4 range from 400 to 500 the compound of formula (IV) corresponds to ACP-001. If p1, p2, p3 and p4 range from 200 to 250 the compound of formula (IV) corresponds to ACP-011.

Preferably, the long-acting growth hormone formulation comprises at least one long-acting growth hormone selected from the group consisting of ACP-001, ACP-011, VRS-317, MOD-4023, Lagoya™ (MOD-4023 hGH-CTP), hGH-CTP, albutropin (TV-1106), ARX201, ALTU-238, PHA-794428, hGH-OctoDex™, NNC126-0083, Nutropin Depot®, Somatropin Biopartners (LB03002), LAPS-hGH, and NNC0195-0092.

Accordingly, in one embodiment the long-acting growth hormone formulation comprises ACP-001.

In another embodiment the long-acting growth hormone formulation comprises ACP-011.

In another embodiment the long-acting growth hormone formulation comprises VRS-317.

In another embodiment the long-acting growth hormone formulation comprises somavaratan.

In another embodiment the long-acting growth hormone formulation comprises MOD-4023.

In another embodiment the long-acting growth hormone formulation comprises Lagova™ (MOD-4023, hGH-CTP).

In another embodiment the long-acting growth hormone formulation comprises hGH-CTP.

In another embodiment the long-acting growth hormone formulation comprises albutropin (TV-1106).

In another embodiment the long-acting growth hormone formulation comprises ARX201.

In another embodiment the long-acting growth hormone formulation comprises ALTU-238.

In another embodiment the long-acting growth hormone formulation comprises PHA-794428.

In another embodiment the long-acting growth hormone formulation comprises hGH-OctoDex™.

In another embodiment the long-acting growth hormone formulation comprises NNC126-0083.

In another embodiment the long-acting growth hormone formulation comprises Nutropin Depot®.

In another embodiment the long-acting growth hormone formulation comprises LB03002.

In another embodiment the long-acting growth hormone formulation comprises Somatropin Biopartners (LB3002.

In another embodiment the long-acting growth hormone formulation comprises LAPS-hGH.

In another embodiment the long-acting growth hormone formulation comprises NNC0195-0092.

In another embodiment the long-acting growth hormone formulation comprises TV-1106.

In another embodiment the long-acting growth hormone formulation comprises GX-H9.

In another embodiment the long-acting growth hormone formulation comprises Jintrolong.

In one embodiment the long-lasting growth hormone formulation is a liquid formulation.

In another embodiment the long-lasting growth hormone formulation is a dry formulation. Preferably, the dry formulation was obtained through lyophilization, i.e. preferably, the dry formulation is a lyophilized formulation.

In a preferred embodiment the long-acting growth hormone formulation is stable for at least 3 month at refrigerated temperature, i.e. at 2 to 8° C.

In another preferred embodiment the long-acting growth hormone is stable for at least 3 month at room temperature, i.e. at 18 to 30° C.

As used herein, the term "growth hormone deficiency" relates to any disease which benefits from the administration of growth hormone. Preferably, growth hormone deficiency is selected from the group consisting of growth hormone deficiency (GHD) in children, idiopathic short stature (ISS), short stature homeobox (SHOX) gene mutations, Turner syndrome (TS), Noonan syndrome (NS), Prader-Willi syndrome (PWS), children born small for gestational age (SGA), chronic renal insufficiency (CRI), growth hormone deficiency (GHD) in adults, wasting due to HIV or AIDS or other malignancies, short bowel syndrome (SBS), sarcopenia, and frailty.

In another embodiment the growth hormone deficiency is GHD in adults.

In another embodiment the growth hormone deficiency is ISS.

In another embodiment the growth hormone deficiency are SHOX gene mutations.

In another embodiment the growth hormone deficiency is TS.

In another embodiment the growth hormone deficiency is NS.

In another embodiment the growth hormone deficiency is PWS.

In another embodiment the growth hormone deficiency is SGA.

In another embodiment the growth hormone deficiency is CRI.

In another embodiment the growth hormone deficiency is wasting due to HIV or AIDS or other malignancies.

In another embodiment the growth hormone deficiency is SBS.

In another embodiment the growth hormone deficiency is sarcopenia.

In another embodiment the growth hormone deficiency is frailty.

In a preferred embodiment the growth hormone deficiency is GHD in children.

Such liquid or dry long-acting growth hormone formulation optionally comprises one or more excipients. Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. The liquid or dry long-acting growth hormone formulation preferably comprises one or more excipients selected from the group consisting of:
(i) Buffering agents: physiologically tolerated buffers to maintain pH in a desired range, such as sodium phosphate, bicarbonate, succinate, histidine, citrate and acetate, sulphate, nitrate, chloride, pyruvate. Antacids such as $Mg(OH)_2$ or $ZnCO_3$ may be also used.
(ii) Isotonicity modifiers: to minimize pain that can result from cell damage due to osmotic pressure differences at the injection depot. Glycerin and sodium chloride are examples. Effective concentrations can be determined by osmometry using an assumed osmolality of 285-315 mOsmol/kg for serum.
(iii) Preservatives and/or antimicrobials: multidose parenteral formulations require the addition of preservatives at a sufficient concentration to minimize risk of patients becoming infected upon injection and corresponding regulatory requirements have been established. Typical preservatives include m-cresol, phenol, methylparaben, ethylparaben, propylparaben, butylparaben, chlorobutanol, benzyl alcohol, phenylmercuric nitrate, thimerosol, sorbic acid, potassium sorbate, benzoic acid, chlorocresol, and benzalkonium chloride.
(iv) Stabilizers: Stabilisation is achieved by strengthening of the protein-stabilising forces, by destabilisation of the denatured state, or by direct binding of excipients to the protein. Stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives. In addition, oligomers or polymers such as cyclodextrins, dextran, dendrimers, PEG or PVP or protamine or HSA may be used.
(v) Anti-adsorption agents: Mainly ionic or non-ionic surfactants or other proteins or soluble polymers are used to coat or adsorb competitively to the inner surface of the formulation's container. E.g., poloxamer (Pluronic F-68), PEG dodecyl ether (Brij 35), polysorbate 20 and 80, dextran, polyethylene glycol, PEG-polyhistidine, BSA and HSA and gelatines. Chosen concentration and type of excipient depends on the effect to be avoided but typically a monolayer of surfactant is formed at the interface just above the CMC value.
(vi) Oxidation protection agents: antioxidants such as ascorbic acid, ectoine, methionine, glutathione, monothioglycerol, morin, polyethylenimine (PEI), propyl gallate, and vitamin E. Chelating agents such as citric acid, EDTA, hexaphosphate, and thioglycolic acid may also be used.
(vii) Viscosifiers or viscosity enhancers: retard settling of the particles in the vial and syringe and are used in order to facilitate mixing and resuspension of the particles and to make the suspension easier to inject (i.e., low force on the syringe plunger). Suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly(glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly(acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone. Such block copolymers as well as the abovementioned poloxamers may exhibit reverse thermal gelation behavior (fluid state at room temperature to facilitate administration and gel state above sol-gel transition temperature at body temperature after injection).
(viii) Spreading or diffusing agent: modifies the permeability of connective tissue through the hydrolysis of components of the extracellular matrix in the intrastitial space such as but not limited to hyaluronic acid, a polysaccharide found in the intercellular space of connective tissue. A spreading agent such as but not limited to hyaluronidase temporarily decreases the viscosity of the extracellular matrix and promotes diffusion of injected drugs.
(ix) Other auxiliary agents: such as wetting agents, viscosity modifiers, antibiotics, hyaluronidase. Acids and bases such as hydrochloric acid and sodium hydroxide are auxiliary agents necessary for pH adjustment during manufacture.

In a preferred embodiment the bracketed dosing regimen consists of a multitude of weight brackets with increasing doses of long-acting growth hormone and wherein the dose of long-acting growth hormone formulation in two neighboring brackets differs by at least 10%. Even more preferably, the dose of long-acting growth hormone formulation in two neighboring brackets differs by at least 12%. Even more preferably, the dose of long-acting growth hormone formulation in two neighboring brackets differs by at least 14%. Even more preferably, the dose of long-acting growth hormone formulation in two neighboring brackets differs by at least 16%. Even more preferably, the dose of long-acting growth hormone formulation in two neighboring brackets differs by at least 18%. Most preferably, the dose of long-acting growth hormone formulation in two neighboring brackets differs by about 20%.

Preferably, the long-acting growth hormone formulation is administered to a patient in the form of the unit dosage forms of the present invention.

Preferably, the long-acting growth hormone formulation is administered to a patient with a time period of at least two days between two administrations. More preferably, the time period between two administrations is at least 3 days, even more preferably at least 4 days, even more preferably at least 5 days, even more preferably at least 6 days and most preferably the time period between two administrations is 7 days. In another embodiment the time period between two administrations is 14 days or one month.

Preferably, the growth hormone deficiency is treated for a time period of at least 6 months, such as of at least 8 months, such as of at least 10 months, such as of at least 12 months, such as of at least 14 months, such as of at least 16 months, such as of at least 20 months, such as of at least 24 months, such as of at least 30 months or such as of at least 36 months.

Preferably, the method of treatment has the same efficacy as a fixed dosage regimen.

In one embodiment the amount of hGH equivalents (in mg/week) given to patients having a weight corresponding to the lower end of any one particular bracket of a bracketed dosage regimen of the present invention corresponds to the dose given in a respective conventional fixed dosage regimen (in mg/kg/week). Accordingly, all other patients having a weight up to the maximum weight of a particular bracket receive a lower dose than they would receive in a standard fixed dosage regimen.

In another embodiment the amount of hGH equivalents (in mg/week) given to patients having a weight corresponding to the high end of any one particular bracket of a bracketed dosage regimen of the present invention corresponds to the dose given in a respective conventional fixed dosage regimen (in mg/kg/week). Accordingly, all other patients having a lower than the maximum weight of the particular bracket receive a higher dose than they would receive in a standard fixed dosage regimen.

In a preferred embodiment the amount of hGH equivalents (in mg/week) given to patients having a weight falling somewhere into the weight range, preferably into the middle, of a particular bracket of a bracketed dosage regimen of the present invention corresponds to the dose given in a respective conventional fixed dosage regimen (in mg/kg/week). Accordingly, all other patients having a weight towards the low or high end of a bracket receive a dose higher or lower, respectively, than they would receive in a standard fixed dosage regimen.

Bracket sizes and hGH equivalents for the bracketed dosage regimen of the present invention can be calculated in a number of ways, as is exemplarily described below. In general, all embodiments regarding the calculation of the amount of hGH equivalents administered in a particular bracket as well as its upper and lower weight limits are based on the following formula:

Weight $W$ in kg×dose $D$ in mg/kg/week=amount of hGH equivalents $E$ in mg/week In other words, based on a dose D, such as a conventionally used dose D from a corresponding fixed dosage regimen (measured in mg/kg/week), and either a suitably chosen weight W (in kg) or a suitably chosen amount of hGH equivalents E (in mg/week), E or W can be calculated, accordingly, for a first bracket. Taking into account an increase of at least 10% between one bracket and the next higher bracket, all brackets can be calculated based on the formula above.

In general, D may be the same or different for each bracket of a bracketed dosage regimen, but is preferably the same for all brackets and the amount of hGH equivalents $E_{1, 2, 3, 4, 5}$, . . . to be administered in the first, second, third, fourth, fifth, . . . bracket remains constant for the whole weight range covered by the first, second, third, fourth, fifth, . . . bracket, but varies between brackets, i.e. increases from one bracket to the next higher bracket by at least 10%.

In a first embodiment the bracketed dosage regimen can be calculated by a method comprising the steps of:
(i) determining the lowest weight of a patient to be treated with the bracketed dosage regimen of the present invention which forms the lower weight limit $W_{1Low}$ of the first bracket $B_1$;
(ii) multiplying $W_{1Low}$ from step (i) with a dose D measured in hGH equivalents used in a fixed dosage regimen to obtain the amount of hGH equivalents $E_1$ administered in the first bracket $B_1$; optionally, rounding $E_1$ to 3, 2, 1 or 0 position(s) after the decimal point;
(iii) determining the upper weight limit $W_{1High}$ of the first bracket $B_1$ by dividing the optionally rounded $E_1$ from step (ii) by (D−(D×factor F)), wherein F may be the same or different for each bracket; optionally, rounding $W_{1High}$ to 3, 2, 1 or 0 position(s) after the decimal point;
(iv) as $W_{2Low} \approx W_{1High}$ with $W_{2Low}$ being the lowest weight of a patient to be allocated to the second bracket $B_2$, multiplying the optionally rounded $W_{1High}$ from step (iii) with D to obtain the amount of hGH equivalents $E_2$ administered in the second bracket $B_2$; optionally, rounding $E_2$ to 3, 2, 1 or 0 position(s) after the decimal point; and
(v) repeating steps (iii) and (iv) accordingly to determine the amounts of hGH equivalents and the lower and upper weight limits for all brackets needed to treat patients having a weight ranging from $W_{1Low}$ to $W_{XHigh}$, wherein $W_{XHigh}$ is the highest weight allocated to the highest bracket $B_X$.

If the brackets are calculated according to the first embodiment, patients having a weight corresponding to the lower weight limit of a bracket receive a dose D, which preferably is the equivalent dose used in a standard fixed dose regimen, and all other patients receive a lower dose.

$W_{1High}$ corresponds to the highest weight allocated to the first bracket and a patient's weight that is only marginally higher already falls into the second bracket where for which the lowest weight is $W_{2Low}$. Consequently, $W_{2Low}$ is almost equal to $W_{1High}$ or $W_{2Low} \approx W_{1High}$.

A suitable lower weight limit $W_{1Low}$ in the calculation of the first embodiment is determined by the lowest weight of a patient to be treated with the bracketed dosage regimen. It is understood that a suitable lower weight limit $W_{1Low}$ is determined by the type of growth hormone deficiency and the corresponding patient population to be treated with the bracketed dosage regimen of the present invention and that $W_{1Low}$ is lower if the patient population comprises children compared to a patient population consisting of adults only. In one embodiment, only pediatric patients are subject to the bracketed dosage of the present invention, such as in the treatment of growth hormone deficiency in children, and consequently the patient population only consists of children. In another embodiment only adults are subject to the bracketed dosage regimen of the present invention, such as in the treatment growth hormone deficiency in adults, and consequently the patient population only consists of adults. In a third embodiment the patient population comprises both children and adults.

Preferably, if the bracketed dosage regimen of the present invention is used in a patient population comprising children, such as in the treatment of growth hormone deficiency in children, $W_{1Low}$ in the calculation of the first embodiment is a weight selected from the range starting from and including 5 to 20 kg, more preferably from 8 to 15 kg, even more preferably from 9 to 14 kg. Preferably, $W_{1Low}$ is a weight selected from 8 kg, 8.5 kg, 9 kg, 9.5 kg, 10 kg, 10.5 kg, 11 kg, 11.5 kg, 12 kg, 12.5 kg, 13 kg, 13.5 kg, 14 kg, 14.5 kg and 15 kg. One preferred weight $W_{1Low}$ is 9 kg. Another preferred weight $W_{1Low}$ is 9.5 kg. Another preferred weight $W_{1Low}$ is 10 kg. Another preferred weight $W_{1Low}$ is 10.5 kg. Another preferred weight $W_{1Low}$ is 11 kg. Another preferred weight $W_{1Low}$ is 11.5 kg. Another preferred weight $W_{1Low}$ is 12 kg. Another preferred weight $W_{1Low}$ is 12.5 kg. Another preferred weight $W_{1Low}$ is 13 kg. Another preferred weight $W_{1Low}$ is 13.5 kg. Another preferred weight $W_{1Low}$ is 14 kg. Another preferred weight $W_{1Low}$ is 14.5 kg. Another preferred weight $W_{1Low}$ is 15 kg.

Preferably, if the bracketed dosage regimen of the present invention is used in a patient population consisting of adults, $W_{1Low}$ in the calculation of the first embodiment is preferably a weight selected from the range starting from 30 to 150 kg, more preferably from 35 to 120 kg, more preferably from 40 to 100 kg.

In a second embodiment the bracketed dosage regimen is calculated by a method comprising the steps of:
(i) determining a suitable amount of hGH equivalent $E_1$ to be administered in a first bracket $B_1$;
(ii) dividing $E_1$ by a dose D measured in hGH equivalents to obtain the lower weight limit $W_{1Low}$ of the first bracket $B_1$; optionally, rounding $W_{1Low}$ to 3, 2, 1 or 0 position(s) after the decimal point;
(iii) determining the upper weight limit $W_{1High}$ of the first bracket $B_1$ by dividing the optionally rounded $E_1$ from step (ii) by (D−(D×factor F)), wherein F may be the same or different for each bracket; optionally, rounding $W_{1High}$ to 3, 2, 1 or 0 position(s) after the decimal point;
(iv) as $W_{2Low} \approx W_{1High}$ with $W_{2Low}$ being the lowest weight of a patient to be allocated to the second bracket $B_2$, multiplying the optionally rounded $W_{1High}$ from step (iii) with D to obtain the amount of hGH equivalents $E_2$ administered in the second bracket $B_2$; optionally, rounding $E_2$ to 3, 2, 1 or 0 position(s) after the decimal point; and
(v) repeating steps (iii) and (iv) accordingly to determine the amounts of hGH equivalents and the lower and upper weight limits for all brackets needed to treat patients having a weight ranging from $W_{1Low}$ to $W_{XHigh}$, wherein $W_{XHigh}$ is the highest weight allocated to the highest bracket $B_X$.

If the brackets are calculated according to the second embodiment, patients having a weight corresponding to the lower weight limit of a bracket receive a dose D, which preferably is the equivalent dose used in a standard fixed dose regimen, and all other patients receive a lower dose.

The amount of hGH equivalent $E_1$ in the calculation of the second embodiment depends on the lowest weight a patient to be treated with the bracketed dosage regimen of the present invention might have and the dose D chosen. Consequently, $E_1$ may be selected from the range covering and including 0.5 to 90 mg/week.

Preferably, in the treatment of growth hormone deficiency in children $E_1$ in the calculation of the first embodiment is selected from the range covering and including 0.5 to 14 mg/week, more preferably 1.2 to 6 mg/week, even more preferably 1.35 to 5.6 mg/week and most preferably 2 to 4 mg/week. Preferably, $E_1$ is selected from the group consisting of 2.0 mg/week, 2.1 mg/week, 2.2 mg/week, 2.3 mg/week, 2.4 mg/week, 2.5 mg/week, 2.6 mg/week, 2.7 mg/week, 2.8 mg/week, 2.9 mg/week, 3.0 mg/week, 3.1 mg/week, 3.2 mg/week, 3.3 mg/week, 3.4 mg/week, 3.5 mg/week, 3.6 mg/week, 3.7 mg/week, 3.8 mg/week, 3.9 mg/week and 4.0 mg/week. In one embodiment $E_1$ is 2.0 mg/week. In another embodiment $E_1$ is 2.1 mg/week. In another embodiment $E_1$ is 2.2 mg/week. In another embodiment $E_1$ is 2.3 mg/week. In another embodiment $E_1$ is 2.4 mg/week. In another embodiment $E_1$ is 2.5 mg/week. In another embodiment $E_1$ is 2.6 mg/week. In another embodiment $E_1$ is 2.7 mg/week. In another embodiment $E_1$ is 2.8 mg/week. In another embodiment $E_1$ is 2.9 mg/week. In another embodiment $E_1$ is 3.0 mg/week. In another embodiment $E_1$ is 3.1 mg/week. In another embodiment $E_1$ is 3.2 mg/week. In another embodiment $E_1$ is 3.3 mg/week. In another embodiment $E_1$ is 3.4 mg/week. In another embodiment $E_1$ is 3.5 mg/week. In another embodiment $E_1$ is 3.6 mg/week. In another embodiment $E_1$ is 3.7 mg/week. In another embodiment $E_1$ is 3.8 mg/week. In another embodiment $E_1$ is 3.9 mg/week. In another embodiment $E_1$ is 4.0 mg/week.

In one embodiment the factor F used in the calculation of the first and second embodiment is different for each bracket. In another embodiment the factor F used in the first and second embodiment is the same for all brackets. Preferably, the factor F used in the first and second embodiment is the same for all brackets.

The factor F used in the calculation of the first and second embodiment is at least 0.1. Preferably, F is a value selected from the range covering and including 0.1 to 0.75, more preferably 0.12 to 0.50, even more preferably 0.15 to 0.40, even more preferably 0.18 to 0.30 and most preferably is about 0.2. Preferably, F is selected from the group consisting of 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29 and 0.3. Even more preferably, F is selected from the group consisting of 0.16, 0.17, 0.18, 0.19, 0.2, 0.21, 0.22, 0.23 and 0.24. In a preferred embodiment F is 0.16. In another preferred embodiment F is 0.17. In another preferred embodiment F is 0.18. In another preferred embodiment F is 0.19. In another preferred embodiment F is 0.2. In another preferred embodiment F is 0.21. In another preferred embodiment F is 0.22. In another preferred embodiment F is 0.23. In another preferred embodiment F is 0.24. More preferably, F is about 0.2. Most preferably, F is 0.2.

In a particularly preferred third embodiment the bracketed dosage regimen is calculated by a method comprising the steps of:
(i) determining a suitable dose D to be administered to patients having a weight in the middle of a weight bracket;
(ii) calculating a suitable dose $D_{Low}$ to be administered to patients having the lowest weight in a weight bracket by increasing D by dose $X_1$ and determining a suitable dose $D_{High}$ to be administered to patients having the highest weight in a weight bracket by decreasing D by dose $X_2$, whereas $D_{Low}$ is at least 10% higher than $D_{High}$;
(iii) determining the lowest weight of a patient $W_{1Low}$ to be allocated to the first bracket $B_1$;
(iv) multiplying $W_{1Low}$ of step (iii) with $D_{Low}$ of step (ii) to obtain the amount of hGH equivalents $E_1$ administered in the first bracket $B_1$; optionally, rounding $E_1$ to 3, 2, 1 or 0 position(s) after the decimal point;
(v) dividing the optionally rounded $E_1$ of step (iv) by $D_{High}$ from (ii) to obtain the highest weight of a patient $W_{1High}$ allocated to the first bracket $B_1$; optionally, rounding $W_{1High}$ to 3, 2, 1 or 0 position(s) after the decimal point;
(vi) as $W_{2Low} \approx W_{1High}$ with $W_{2Low}$ being the lowest weight of a patient to be allocated to the second bracket $B_2$, calculating the amount of hGH equivalents $E_2$ to be administered in the second bracket $B_2$ by multiplying the optionally rounded $W_{1High}$ from step (v) with $D_{Low}$; optionally, rounding $E_2$ to 3, 2, 1 or 0 position(s) after the decimal point;
(vii) repeating steps (iv) to (vi) accordingly to determine the amounts of hGH equivalents and the lowest weight limits for all brackets needed to treat patients having a weight ranging from $W_{1Low}$ to $W_{XHigh}$, wherein $W_{XHigh}$ is the highest weight in the highest bracket $B_X$.

If the brackets are calculated according to the third embodiment patients having a weight falling somewhere into a bracket receive a dose D, which preferably is the equivalent dose used in a standard fixed dose regimen, and those patients with a lower or higher weight receive a dose that is higher or lower, respectively.

A suitable lower weight limit $W_{1Low}$ in the calculation of the third embodiment is determined by the lowest weight of a patient to be treated with the bracketed dosage regimen. It is understood that a suitable lower weight limit $W_{1Low}$ is determined by the type of growth hormone deficiency and the corresponding patient population to be treated with the bracketed dosage regimen of the present invention and that $W_{1Low}$ is lower if the patient population comprises children compared to a patient population consisting of adults only. In one embodiment, only pediatric patients are subject to the bracketed dosage of the present invention, such as in the treatment of growth hormone deficiency in children, and consequently the patient population only consists of children. In another embodiment only adults are subject to the bracketed dosage of the present invention, such as in the treatment growth hormone deficiency in adults, and consequently the patient population only consists of adults. In a third embodiment the patient population comprises both children and adults.

Preferably, if the bracketed dosage regimen of the present invention is used in a patient population comprising children, such as in the treatment of growth hormone deficiency in children, $W_{1Low}$ in the calculation of the third embodiment is a weight selected from the range starting from and including 5 to 20 kg, more preferably from 8 to 15 kg, even more preferably from 9 to 14 kg. Preferably, $W_{1Low}$ is a weight selected from 8 kg, 8.5 kg, 9 kg, 9.5 kg, 10 kg, 10.5 kg, 11 kg, 11.5 kg, 12 kg, 12.5 kg, 13 kg, 13.5 kg, 14 kg, 14.5 kg and 15 kg. One preferred weight $W_{1Low}$ is 9 kg. Another preferred weight $W_{1Low}$ is 9.5 kg. Another preferred weight $W_{1Low}$ is 10 kg. Another preferred weight $W_{1Low}$ is 10.5 kg. Another preferred weight $W_{1Low}$ is 11 kg. Another preferred weight $W_{1Low}$ is 11.5 kg. Another preferred weight $W_{1Low}$ is 12 kg. Another preferred weight $W_{1Low}$ is 12.5 kg. Another preferred weight $W_{1Low}$ is 13 kg. Another preferred weight $W_{1Low}$ is 13.5 kg. Another preferred weight $W_{1Low}$ is 14 kg. Another preferred weight $W_{1Low}$ is 14.5 kg. Another preferred weight $W_{1Low}$ is 15 kg.

Preferably, if the bracketed dosage regimen of the present invention is used in a patient population consisting of adults, $W_{1Low}$ in the calculation of the third embodiment is preferably a weight selected from the range starting from 30 to 150 kg, more preferably from 35 to 120 kg, more preferably from 40 to 100 kg.

In a particularly preferred fourth embodiment the bracketed dosage regimen is calculated by a method comprising the steps of:
(i) determining a suitable dose D to be administered to patients having a weight within a weight bracket, preferably in the middle of a weight bracket;
(ii) calculating a suitable dose $D_{Low}$ to be administered to patients having the lowest weight in a weight bracket by increasing D by dose $X_1$ and determining a suitable dose $D_{High}$ to be administered to patients having the highest weight in a weight bracket by decreasing D by dose $X_2$, whereas $D_{Low}$ is at least 10% higher than $D_{High}$;
(iii) determining a suitable amount of hGH equivalents $E_1$ administered in the first bracket $B_1$;
(iv) dividing $E_1$ from step (iii) by $D_{Low}$ from step (ii) to obtain the lowest weight of a patient $W_{1Low}$ allocated to the first bracket $B_1$; optionally, rounding $W_{1Low}$ to 3, 2, 1 or 0 position(s) after the decimal point;
(v) dividing $E_1$ from step (iii) by $D_{High}$ from step (ii) to obtain the highest weight of a patient $W_{1High}$ allocated to the first bracket $B_1$; optionally, rounding $W_{1High}$ to 3, 2, 1 or 0 position(s) after the decimal point;
(vi) as $W_{2Low} \approx W_{1High}$ with $W_{2Low}$ being the lowest weight of a patient to be allocated to the second bracket $B_2$, calculating the amount of hGH equivalents $E_2$ to be administered in the second bracket $B_2$ by multiplying the optionally rounded $W_{1High}$ from step (v) with $D_{Low}$; optionally, rounding $E_2$ to 3, 2, 1 or 0 position(s) after the decimal point;
(vii) repeating steps (iv) to (vi) accordingly to determine the amounts of hGH equivalents and the lowest weight limits for all brackets needed to treat patients having a weight ranging from $W_{1Low}$ to $W_{XHigh}$, wherein $W_{XHigh}$ is the highest weight in the highest bracket $B_X$.

If the brackets are calculated according to the fourth embodiment patients having a weight falling somewhere into a bracket receive a dose D, which preferably is the equivalent dose used in a standard fixed dose regimen, and those patients with a lower or higher weight receive a dose that is higher or lower, respectively.

The amount of hGH equivalent $E_1$ in the calculation of the fourth embodiment depends on the lowest weight a patient to be treated with the bracketed dosage regimen of the present invention might have and the dose D chosen. Consequently, $E_1$ may be selected from the range covering and including 0.5 to 90 mg/week.

Preferably, in the treatment of growth hormone deficiency in children in the calculation of the fourth embodiment $E_1$ is selected from the range covering and including 0.5 to 14 mg/week, more preferably 1.2 to 6 mg/week, even more preferably 1.35 to 5.6 mg/week and most preferably 2 to 4 mg/week. Preferably, $E_1$ is selected from the group consisting of 2.0 mg/week, 2.1 mg/week, 2.2 mg/week, 2.3 mg/week, 2.4 mg/week, 2.5 mg/week, 2.6 mg/week, 2.7 mg/week, 2.8 mg/week, 2.9 mg/week, 3.0 mg/week, 3.1 mg/week, 3.2 mg/week, 3.3 mg/week, 3.4 mg/week, 3.5 mg/week, 3.6 mg/week, 3.7 mg/week, 3.8 mg/week, 3.9 mg/week and 4.0 mg/week.

Preferably, $D_{Low}$ of the calculation of the third and fourth embodiment is at least 10% and at most 75% higher than $D_{High}$, even more preferably $D_{Low}$ is at least 12% and at most 50% higher than $D_{High}$, even more preferably $D_{Low}$ is at least 15% and at most 40% higher than $D_{High}$, even more preferably $D_{Low}$ is at least 18% and at most 30% higher than $D_{High}$. In one embodiment $D_{Low}$ is about 25% higher than $D_{High}$. In another embodiment $D_{Low}$ is about 24% higher than $D_{High}$. In another embodiment $D_{Low}$ is about 23% higher than $D_{High}$. In another embodiment $D_{Low}$ is about 22% higher than $D_{High}$. In another embodiment $D_{Low}$ is about 21% higher than $D_{High}$. In another embodiment $D_{Low}$ is about 20% higher than $D_{High}$.

Preferably, $X_1$ and $X_2$ in the calculation of the third and fourth embodiment are independently selected from the range starting and including from 0.001 to 0.05 mg/kg/week, more preferably from 0.01 to 0.04 mg/kg/week, even more preferably from 0.012 to 0.03 mg/kg/week, even more preferably from 0.015 to 0.025 mg/kg/week and most preferably from 0.018 to 0.022 mg/kg/week. Preferably, $X_1$ and $X_2$ are independently selected from the group consisting of 0.01 mg/kg/week, 0.011 mg/kg/week, 0.012 mg/kg/week, 0.013 mg/kg/week, 0.014 mg/kg/week, 0.015 mg/kg/week, 0.016 mg/kg/week, 0.017 mg/kg/week, 0.018 mg/kg/week, 0.019 mg/kg/week, 0.02 mg/kg/week, 0.021 mg/kg/week, 0.022 mg/kg/week, 0.023 mg/kg/week, 0.024 mg/kg/week, 0.025 mg/kg/week, 0.026 mg/kg/week, 0.027 mg/kg/week, 0.028 mg/kg/week, 0.029 mg/kg/week and 0.03 mg/kg/week.

In one preferred embodiment $X_1$ in the calculation of the third and fourth embodiment is 0.01 mg/kg/week. In another preferred embodiment $X_1$ is 0.011 mg/kg/week. In another preferred embodiment $X_1$ is 0.012 mg/kg/week. In another preferred embodiment $X_1$ is 0.013 mg/kg/week. In another preferred embodiment $X_1$ is 0.014 mg/kg/week. In another preferred embodiment $X_1$ is 0.015 mg/kg/week. In another preferred embodiment $X_1$ is 0.016 mg/kg/week. In another preferred embodiment $X_1$ is 0.017 mg/kg/week. In another preferred embodiment $X_1$ is 0.018 mg/kg/week. In another preferred embodiment $X_1$ is 0.019 mg/kg/week. In another preferred embodiment $X_1$ is 0.02 mg/kg/week. In another preferred embodiment $X_1$ is 0.021 mg/kg/week. In another preferred embodiment $X_1$ is 0.022 mg/kg/week. In another preferred embodiment $X_1$ is 0.023 mg/kg/week. In another preferred embodiment $X_1$ is 0.024 mg/kg/week. In another preferred embodiment $X_1$ is 0.025 mg/kg/week. In another preferred embodiment $X_1$ is 0.026 mg/kg/week. In another preferred embodiment $X_1$ is 0.027 mg/kg/week. In another preferred embodiment $X_1$ is 0.028 mg/kg/week. In another preferred embodiment $X_1$ is 0.029 mg/kg/week. In another preferred embodiment $X_1$ is 0.030 mg/kg/week.

In one preferred embodiment $X_2$ in the calculation of the third and fourth embodiment is 0.01 mg/kg/week. In another preferred embodiment $X_2$ is 0.011 mg/kg/week. In another preferred embodiment $X_2$ is 0.012 mg/kg/week. In another preferred embodiment $X_2$ is 0.013 mg/kg/week. In another preferred embodiment $X_2$ is 0.014 mg/kg/week. In another preferred embodiment $X_2$ is 0.015 mg/kg/week. In another preferred embodiment $X_2$ is 0.016 mg/kg/week. In another preferred embodiment $X_2$ is 0.017 mg/kg/week. In another preferred embodiment $X_2$ is 0.018 mg/kg/week. In another preferred embodiment $X_2$ is 0.019 mg/kg/week. In another preferred embodiment $X_2$ is 0.02 mg/kg/week. In another preferred embodiment $X_2$ is 0.021 mg/kg/week. In another preferred embodiment $X_2$ is 0.022 mg/kg/week. In another preferred embodiment $X_2$ is 0.023 mg/kg/week. In another preferred embodiment $X_2$ is 0.024 mg/kg/week. In another preferred embodiment $X_2$ is 0.025 mg/kg/week. In another preferred embodiment $X_2$ is 0.026 mg/kg/week. In another preferred embodiment $X_2$ is 0.027 mg/kg/week. In another preferred embodiment $X_2$ is 0.028 mg/kg/week. In another preferred embodiment $X_2$ is 0.029 mg/kg/week. In another preferred embodiment $X_2$ is 0.030 mg/kg/week.

Preferably, $X_1$ and $X_2$ in the calculation of the third and fourth embodiment are the same dose. Accordingly, in such embodiment patients having a weight corresponding to the middle of a weight bracket receive the dose D.

More preferably, $X_1$ and $X_2$ in the calculation of the third and fourth embodiment are the same dose which is selected from the group consisting of 0.015 mg/kg/week, 0.016 mg/kg/week, 0.017 mg/kg/week, 0.018 mg/kg/week, 0.019 mg/kg/week, 0.02 mg/kg/week, 0.021 mg/kg/week, 0.022 mg/kg/week, 0.023 mg/kg/week, 0.024 mg/kg/week and 0.025 mg/kg/week. Even more preferably $X_1$ and $X_2$ are the same dose which is selected from the group consisting of 0.018 mg/kg/week, 0.019 mg/kg/week, 0.02 mg/kg/week, 0.021 mg/kg/week and 0.022 mg/kg/week. Most preferably $X_1$ and $X_2$ are both 0.02 mg/kg/week.

In a preferred embodiment D used in the calculation of a bracketed dosage regimen according to the first, second, third and fourth embodiment is the same in all brackets.

The dose D used in the calculations according to the first, second, third and fourth embodiment corresponds preferably to the respective dose administered in the corresponding fixed dose regimen and thus depends on the disease to be treated with the bracketed dosage regimen of the present invention.

A preferred value for D in the calculation of the first, second, third and fourth embodiment for the treatment of growth hormone deficiency in children is selected from the range covering and including 0.14 mg/kg/week to 0.40 mg/kg/week, even more preferably 0.16 mg/kg/week/to 0.3 mg/kg/week. Preferably D is selected from the group consisting of 0.14 mg/kg/week, 0.15 mg/kg/week, 0.16 mg/kg/week, 0.17 mg/kg/week, 0.18 mg/kg/week, 0.19 mg/kg/week, 0.20 mg/kg/week, 0.21 mg/kg/week, 0.22 mg/kg/week, 0.23 mg/kg/week, 0.24 mg/kg/week, 0.25 mg/kg/week, 0.26 mg/kg/week, 0.27 mg/kg/week, 0.28 mg/kg/week, 0.29 mg/kg/week, 0.30 mg/kg/week, 0.31 mg/kg/week, 0.32 mg/kg/week, 0.33 mg/kg/week, 0.34 mg/kg/week, 0.35 mg/kg/week, 0.36 mg/kg/week, 0.37 mg/kg/week, 0.38 mg/kg/week, 0.39 mg/kg/week and 0.40 mg/kg/week. In a preferred embodiment D is 0.16 mg/kg/week. In another preferred embodiment D is 0.17 mg/kg/week. In another preferred embodiment D is 0.18 mg/kg/week. In another preferred embodiment D is 0.19 mg/kg/week. In another preferred embodiment D is 0.20 mg/kg/week. In another preferred embodiment D is 0.21 mg/kg/week. In another preferred embodiment D is 0.22 mg/kg/week. In another preferred embodiment D is 0.23 mg/kg/week. In another preferred embodiment D in the calculation of the first, second, third or fourth embodiment is 0.24 mg/kg/week. In another preferred embodiment D is 0.25 mg/kg/week. In another preferred embodiment D is 0.26 mg/kg/week. In another preferred embodiment D is 0.27 mg/kg/week. In another preferred embodiment D is 0.28 mg/kg/week. In another preferred embodiment D is 0.29 mg/kg/week. In another preferred embodiment D is 0.30 mg/kg/week. In general, it is preferred that D is 0.24 mg/kg/week for European patients and that D is 0.3 mg/kg/week for U.S. patients. More preferably, D is 0.24 mg/kg/week for European and U.S. patients.

The highest weight $W_{XHigh}$ a patient may have to be treated with the bracketed dosage regimen calculated according to the first, second, third or fourth embodiment is determined by the type of growth hormone deficiency and the corresponding patient population to be treated with the bracketed dosage regimen of the present invention. Preferably, $W_{XHigh}$ is at most 180 kg, such as no higher than 160 kg or no higher than 140 kg.

In a fifth embodiment the bracketed dosage regimen is calculated by a method comprising the steps of:
 (i) determining the amounts of hGH equivalents $E_1$ to $E_X$ to be administered in each of the brackets ranging from the first bracket $B_1$ to the highest bracket $B_X$, wherein the amount of hGH equivalents to be administered increases between one bracket and the next higher bracket and wherein each such increase is independently at least 10%;
 (ii) determining a suitable dose $D_1$ to $D_X$ for each bracket $B_1$ to $B_X$ which may be the same or different for each bracket; and
 (iii) calculating the lower weight limits $W_{1Low}$ to $W_{XLow}$ for each bracket $B_1$ to $B_X$ by dividing each one of $E_1$ to $E_X$ from step (i) by the corresponding dose $D_1$ to $D_X$ from step (ii) to obtain the corresponding lower weight limit of said bracket; optionally rounding each one of $W_{1Low}$ to $W_{XLow}$ to 3, 2, 1 or 0 position(s) after the decimal point.

If the brackets are calculated according to the fifth embodiment patients having a weight corresponding to the lower weight limit of a bracket receive the highest dose, which preferably corresponds to the equivalent dose used in a standard fixed dosage regimen, and all other patients receive a lower dose.

Preferably, $D_1$ to $D_X$ in the calculation of the fifths embodiment are independently selected from the range covering and including 0.02 to 1.5 mg/kg/week.

Preferably, $D_1$ to $D_X$ in the calculation of the fifth embodiment are the same, more preferably $D_1$ to $D_X$ of the fifth embodiment correspond to a dose used in the corresponding fixed dose regimen. Even more preferably, $D_1$ to $D_x$ correspond to D of the first, second, third and fourth embodiment with the preferred embodiments for D as described above.

In a sixth embodiment the bracketed dosage regimen is calculated by a method comprising the steps of:
(i) determining the amounts of hGH equivalents $E_1$ to $E_X$ to be administered in each of the brackets ranging from the first bracket $B_1$ to the highest bracket $B_X$, wherein the amount of hGH equivalents to be administered increases between one bracket and the next higher bracket and wherein each such increase is independently at least 10%;
(ii) determining a suitable dose $D_1$ to $D_X$ to be administered to patients having a weight in the middle of each weight bracket $B_1$ to $B_X$, wherein $D_1$ to $D_X$ may be the same or different for each bracket;
(iii) calculating a suitable dose $D_{1Low}$ to $D_{XLow}$ to be administered to patients having a weight corresponding to the lowest weigh in a weight bracket by increasing D by dose $X_1$ and determining a suitable dose $D_{1High}$ to $D_{XHigh}$ be administered to patients having the highest weight corresponding to the highest weight in a weight bracket by decreasing D by dose $X_2$, whereas $D_{Low}$ is at least 10% higher than $D_{High}$; and
(iv) calculating the lower weight limits $W_{1Low}$ to $W_{XLow}$ for each bracket $B_1$ to $B_X$ by dividing each of $E_1$ to $E_X$ from step (i) by the corresponding dose $D_{1Low}$ to $D_{XLow}$ from step (iii) to obtain the corresponding lower weight limit of said bracket; optionally rounding each one of $W_{1Low}$ to $W_{XLow}$ to 3, 2, 1 or 0 position(s) after the decimal point.

If the brackets are calculated according to the sixth embodiment patients having a weight falling somewhere into a bracket receive a dose D, which preferably is the equivalent dose used in a standard fixed dose regimen, and those patients with a lower or higher weight receive a dose that is higher or lower, respectively.

Preferably, $D_1$ to $D_X$ in the calculation of the sixth embodiment are independently selected from the range covering and including 0.02 to 1.5 mg/kg/week.

Preferably, $D_1$ to $D_X$ in the calculation of the sixth embodiment are the same, more preferably $D_1$ to $D_X$ of the fifth embodiment correspond to a dose used in the corresponding fixed dose regimen. Even more preferably, $D_1$ to $D_x$ correspond to D of the first, second, third and fourth embodiment with the preferred embodiments for D as described above.

Preferably, $D_{Low}$ in the calculation of the sixth embodiment is at least 10% and at most 75% higher than $D_{High}$, even more preferably $D_{Low}$ is at least 12% and at most 50% higher than $D_{High}$, even more preferably $D_{Low}$ is at least 15% and at most 40% higher than $D_{High}$, even more preferably $D_{Low}$ is at least 18% and at most 30% higher than $D_{High}$. In one embodiment $D_{Low}$ is about 25% higher than $D_{High}$. In another embodiment $D_{Low}$ is about 24% higher than $D_{High}$. In another embodiment $D_{Low}$ is about 23% higher than $D_{High}$. In another embodiment $D_{Low}$ is about 22% higher than $D_{High}$. In another embodiment $D_{Low}$ is about 21% higher than $D_{High}$. In another embodiment $D_{Low}$ is about 20% higher than $D_{High}$.

Preferred embodiments for $X_1$ and $X_2$ in the calculation of the sixth embodiment are as described for $X_1$ and $X_2$ of the third and fourth embodiment.

The amount of hGH equivalent $E_1$ to $E_X$ in the calculation of the fifth and sixth embodiment increases from one bracket to the next higher bracket by at least 10%. $E_1$ depends on the lowest weight a patient to be treated with the bracketed dosage regimen of the present invention might have and the dose D chosen. Consequently, $E_1$ may be selected from the range covering and including 0.5 to 90 mg/week.

In the calculation of the sixth embodiment the amount of hGH equivalent increases from one bracket $E_z$ to the next higher bracket $E_{z+1}$ by at least 10%. Preferably, this increase is at least 10% and at most 75%, even more preferably the increase is at least 12% and at most 50%, even more preferably this increase is at least 15% and at most 40%, even more preferably this increase is at least 18% and at most 30%. In one embodiment this increase is about 25%. In another embodiment this increase is about 24%. In another embodiment this increase is about 23%. In another embodiment this increase is about 22%. In another embodiment this increase is about 21%. In another embodiment increase is about 20%.

In general, several growth hormone deficiency diseases may benefit from treatment with the bracketed dosage regimen. It is understood that not all growth hormone deficiency diseases are approved in each territory of the World. As such the corresponding fixed doses represent approved doses in certain geographic areas, and actual prescribed or administered doses may vary among different territories. In general, each growth hormone deficiency disease to be treated with the bracketed dosage regimen is preferably treated such that either the patients having weight at the low end, in the middle or at the high end of a weight bracket receive an amount of hGH that is equivalent to what is used in a corresponding fixed dosage regimen, which are as follows:

In a fixed dosage regimen GHD in children is treated with a dose of hGH equivalents ranging from and including 0.14 to 0.40 mg/kg/week, preferably 0.21 to 0.30 mg/kg/week. Accordingly, D as used in the calculation of the first, second, third and fourth embodiment and $D_1$ to $D_X$ as used in the calculation of the fifth and sixth embodiment preferably range from and include 0.14 to 0.40 mg/kg/week, more preferably 0.21 to 0.30 mg/kg/week, if the growth hormone deficiency is growth hormone deficiency in children.

In a fixed dosage regimen GHD in adults is treated with a dose of hGH equivalents ranging from and including 0.02 to 0.10 mg/kg/week, preferably 0.04 to 0.08 mg/kg/week. Accordingly, D as used in the calculation of the first, second, third and fourth embodiment and $D_1$ to $D_X$ as used in the calculation of the fifth and sixth embodiment preferably range from and include 0.02 to 0.10 mg/kg/week, more preferably 0.04 to 0.08 mg/kg/week, if the growth hormone deficiency is growth hormone deficiency in adults.

In a fixed dosage regimen ISS is treated with a dose of hGH equivalents ranging from and including 0.21 to 0.70 mg/kg/week, preferably 0.30 to 0.47 mg/kg/week. Accordingly, D as used in the calculation of the first, second, third and fourth embodiment and $D_1$ to $D_X$ as used in the calculation of the fifth and sixth embodiment preferably range from and include 0.21 to 0.70 mg/kg/week, more preferably 0.30 to 0.47 mg/kg/week, if the growth hormone deficiency is ISS.

In a fixed dosage regimen SHOX gene mutations is treated with a dose of hGH equivalents ranging from and including 0.21 to 0.50 mg/kg/week, preferably 0.30 to 0.40 mg/kg/week. Accordingly, D as used in the calculation of the first, second, third and fourth embodiment and $D_1$ to $D_X$ as used in the calculation of the fifth and sixth embodiment preferably range from and include 0.21 to 0.50 mg/kg/week, more preferably 0.30 to 0.40 mg/kg/week, if the growth hormone deficiency is SHOX gene mutations.

In a fixed dosage regimen TS is treated with a dose of hGH equivalents ranging from and including 0.21 to 0.50 mg/kg/week, preferably 0.30 to 0.40 mg/kg/week. Accordingly, D as used in the calculation of the first, second, third and fourth embodiment and $D_1$ to $D_X$ as used in the calculation of the fifth and sixth embodiment preferably range from and include 0.21 to 0.50 mg/kg/week, more preferably 0.30 to 0.40 mg/kg/week, if the growth hormone deficiency is TS.

In a fixed dosage regimen NS is treated with a dose of hGH equivalents ranging from and including 0.24 to 0.60 mg/kg/week, preferably 0.40 to 0.50 mg/kg/week. Accordingly, D as used in the calculation of the first, second, third and fourth embodiment and $D_1$ to $D_X$ as used in the calculation of the fifth and sixth embodiment preferably range from and include 0.24 to 0.60 mg/kg/week, more preferably 0.40 to 0.50 mg/kg/week, if the growth hormone deficiency is NS.

In a fixed dosage regimen PWS is treated with a dose of hGH equivalents ranging from and including 0.16 to 0.35 mg/kg/week, preferably 0.20 to 0.30 mg/kg/week. Accordingly, D as used in the calculation of the first, second, third and fourth embodiment and $D_1$ to $D_X$ as used in the calculation of the fifth and sixth embodiment preferably range from and include 0.16 to 0.35 mg/kg/week, more preferably 0.20 to 0.30 mg/kg/week, if the growth hormone deficiency is PWS.

In a fixed dosage regimen SGA is treated with a dose of hGH equivalents ranging from and including 0.24 to 0.60 mg/kg/week, preferably 0.40 to 0.50 mg/kg/week. Accordingly, D as used in the calculation of the first, second, third and fourth embodiment and $D_1$ to $D_X$ as used in the calculation of the fifth and sixth embodiment preferably range from and include 0.24 to 0.60 mg/kg/week, more preferably 0.40 to 0.50 mg/kg/week, if the growth hormone deficiency is SGA.

In a fixed dosage regimen CRI is treated with a dose of hGH equivalents ranging from and including 0.21 to 0.50 mg/kg/week, preferably 0.30 to 0.40 mg/kg/week. Accordingly, D as used in the calculation of the first, second, third and fourth embodiment and $D_1$ to $D_X$ as used in the calculation of the fifth and sixth embodiment preferably range from and include 0.21 to 0.50 mg/kg/week, more preferably 0.30 to 0.40 mg/kg/week, if the growth hormone deficiency is CRI.

In a fixed dosage regimen HIV or AIDS or other malignancies is treated with a dose of hGH equivalents ranging from and including 0.3 to 1.4 mg/kg/week, preferably 0.45 to 0.90 mg/kg/week. Accordingly, D as used in the calculation of the first, second, third and fourth embodiment and $D_1$ to $D_X$ as used in the calculation of the fifth and sixth embodiment preferably range from and include 0.3 to 1.4 mg/kg/week, more preferably 0.45 to 0.90 mg/kg/week, if the growth hormone deficiency is HIV or AIDS or other malignancies.

In a fixed dosage regimen SBS is treated with a dose of hGH equivalents ranging from and including 0.35 to 1.5 mg/kg/week, preferably 0.6 to 1.20 mg/kg/week. Accordingly, D as used in the calculation of the first, second, third and fourth embodiment and $D_1$ to $D_X$ as used in the calculation of the fifth and sixth embodiment preferably range from and include 0.35 to 1.5 mg/kg/week, more preferably 0.60 to 1.20 mg/kg/week, if the growth hormone deficiency is SBS.

In a fixed dosage regimen sarcopenia is treated with a dose of hGH equivalents ranging from and including 0.02 to 0.10 mg/kg/week, preferably 0.04 to 0.08 mg/kg/week. Accordingly, D as used in the calculation of the first, second, third and fourth embodiment and $D_1$ to $D_X$ as used in the calculation of the fifth and sixth embodiment preferably range from and include 0.02 to 0.10 mg/kg/week, more preferably 0.04 to 0.08 mg/kg/week, if the growth hormone deficiency is sarcopenia.

In a fixed dosage regimen frailty is treated with a dose of hGH equivalents ranging from and including 0.02 to 0.10 mg/kg/week, preferably 0.04 to 0.08 mg/kg/week. Accordingly, D as used in the calculation of the first, second, third and fourth embodiment and $D_1$ to $D_X$ as used in the calculation of the fifth and sixth embodiment preferably range from and include 0.02 to 0.10 mg/kg/week, more preferably 0.04 to 0.08 mg/kg/week, if the growth hormone deficiency is frailty.

If the growth hormone deficiency is growth hormone deficiency in children, the brackets are most preferably calculated according to a seventh embodiment which is a method comprising the steps of (i) determining a suitable amount of hGH equivalent $E_1$ to be administered in a first bracket $B_1$;

(ii) dividing $E_1$ of step (i) by 0.26 mg/week to obtain the lower weight limit $W_{1Low}$ for the first bracket $B_1$; optionally rounding $W_{1Low}$ to 3, 2, 1 or 0 position(s) after the decimal point;

(iii) dividing $E_1$ of step (i) by 0.22 mg/week to obtain the upper limit $W_{1High}$ for the first bracket $B_1$; optionally rounding $W_{1High}$ to 3, 2, 1 or 0 position(s) after the decimal point;

(iv) as $W_{2Low} \approx W_{1High}$ with $W_{2Low}$ being the lowest weight of a patient to be allocated to the second bracket $B_2$, calculating the amount of hGH equivalents $E_2$ to be administered in the second bracket $B_2$ by multiplying the optionally rounded $W_{1High}$ from step (iii) with 0.26 mg/week; optionally, rounding $E_2$ to 3, 2, 1 or 0 position(s) after the decimal point; and (v) repeating steps (ii) to (iv) accordingly to determine the amounts of hGH equivalents and the lowest weight limits for all brackets needed to treat patients having a weight ranging from $W_{1Low}$ to $W_{XHigh}$, wherein $W_{XHigh}$ is the highest weight in the highest bracket $B_X$;

wherein patients having a weight corresponding to the lower weight limit of a bracket receive 0.26 mg/kg/week and those at the high end receive 0.22 mg/kg/week, which corresponds to 0.24 mg/kg/week+/−0.02 mg/kg/week.

Preferred embodiment for $E_1$ in the calculation of the seventh embodiment are as described in the first embodiment.

In one preferred embodiment the bracketed dosage regimen comprises the following bracket sizes:

| hGH equivalents (mg) | Weight Bracket: (from kg) |
| --- | --- |
| 3.1 | 13- |
| 3.8 | 16- |
| 4.5 | 19- |
| 5.4 | 23- |
| 6.5 | 27- |
| 7.8 | 33- |
| 9.4 | 39- |
| 11.3 | 47- |

| hGH equivalents (mg) | Weight Bracket: (from kg) |
|---|---|
| 13.5 | 56- |
| 16.2 | 68-82 |

Such bracketed dosage regimen is particularly preferred for patients which traditionally receive 0.24 mg of hGH/kg/week, such as for example EU patients.

Such bracketed dosage regimen may be achieved with a combination of two formulations having different strengths of hGH equivalents, namely 14 mg hGH equivalents/ml and 28 mg hGH equivalents/ml which results in the following bracketed dosage regimen:

| Strength | Volume (ml) | hGH equivalents (mg) | Weight Bracket: (from kg) |
|---|---|---|---|
| 14 mg hGH equivalents/ml | 0.22 | 3.1 | 13- |
| | 0.27 | 3.8 | 16- |
| | 0.32 | 4.5 | 19- |
| | 0.39 | 5.4 | 23- |
| | 0.46 | 6.5 | 27- |
| 28 mg hGH equivalents/ml | 0.28 | 7.8 | 33- |
| | 0.34 | 9.4 | 39- |
| | 0.40 | 11.3 | 47- |
| | 0.48 | 13.5 | 56- |
| | 0.58 | 16.2 | 68-82 |

In a preferred embodiment the bracketed dosage regimen comprises the following bracket sizes:

| hGH equivalents (mg) | Weight Bracket: (from kg) |
|---|---|
| 3.1 | 12- |
| 3.8 | 15- |
| 4.5 | 17- |
| 5.4 | 21- |
| 6.5 | 25- |
| 7.8 | 30- |
| 9.4 | 36- |
| 11.3 | 43- |
| 13.5 | 52- |
| 16.2 | 62-74 |

Such bracketed dosage regimen is particularly preferred for patients which traditionally receive 0.24 mg of hGH/kg/week, such as for example EU patients.

Most preferably, such bracketed dosage regimen may be achieved with a combination of two formulations having different strengths of hGH equivalents, namely 14 mg hGH equivalents/ml and 28 mg hGH equivalents/ml which results in the following bracketed dosage regimen:

| Strength | Volume (ml) | hGH equivalents (mg) | Weight Bracket: (from kg) |
|---|---|---|---|
| 14 mg hGH equivalents/ml | 0.22 | 3.1 | 12- |
| | 0.27 | 3.8 | 15- |
| | 0.32 | 4.5 | 17- |
| | 0.39 | 5.4 | 21- |
| | 0.46 | 6.5 | 25- |
| 28 mg hGH equivalents/ml | 0.28 | 7.8 | 30- |
| | 0.34 | 9.4 | 36- |
| | 0.40 | 11.3 | 43- |
| | 0.48 | 13.5 | 52- |
| | 0.58 | 16.2 | 62-74 |

In another preferred embodiment the bracketed dosage regimen comprises the following bracket sizes:

| hGH equivalents (mg) | Weight Bracket: (from kg) |
|---|---|
| 3.8 | 12- |
| 4.5 | 14- |
| 5.4 | 17- |
| 6.5 | 20- |
| 7.8 | 24- |
| 9.4 | 29- |
| 11.3 | 35- |
| 13.5 | 42- |
| 16.2 | 51- |
| 19.5 | 61-70 |

Such bracketed dosage regimen is particularly preferred for patients which traditionally receive 0.30 mg of hGH/kg/week, such as for example US patients.

When converting a bracketed dosage regimen into unit dosage forms comprising the long-acting growth hormone formulation, the long-acting growth hormone formulation must have a suitable strength.

The term "strength" as used herein means the concentration of growth hormone equivalents (in mg/ml) in the formulation.

A suitable strength ensures that the volume to be filled into the smallest unit dose is not smaller than the minimal filling volume that can reliably be handled during the manufacturing process. Preferably, the minimal volume is at least larger than 0.25 ml, such as 0.26 ml, 0.27 ml or 0.28 ml. Likewise, a suitable strength ensures an injection volume lower than or equal to 1.00 ml to minimize the inconvenience of the patient, such as preferably lower than or equal to 0.90 ml, lower than or equal to 0.8 ml, lower than or equal to 0.7 ml or lower than or equal to 0.6 ml.

In order to provide a suitable volume for the manufacturing process and for the injection into a patient, the unit dosage forms for the bracketed dosage of the present invention may be based on one pharmaceutical formulation comprising long-acting growth hormone or on more than one pharmaceutical formulation comprising long-acting growth hormone in which case the pharmaceutical formulations comprising long-acting growth hormone preferably have different strengths.

Most preferably, such bracketed dosage regimen may be achieved with a combination of two formulations having different strengths of hGH equivalents, namely 14 mg hGH equivalents/ml and 28 mg hGH equivalents/ml which results in the following bracketed dosage regimen:

| Strength | Volume (ml) | hGH equivalents (mg) | Weight Bracket: (from kg) |
|---|---|---|---|
| 14 mg hGH equivalents/ml | 0.27 | 3.8 | 12- |
| | 0.32 | 4.5 | 14- |
| | 0.39 | 5.4 | 17- |
| | 0.46 | 6.5 | 20- |
| 28 mg hGH equivalents/ml | 0.28 | 7.8 | 24- |
| | 0.34 | 9.4 | 29- |
| | 0.40 | 11.3 | 35- |

| Strength | Volume (ml) | hGH equivalents (mg) | Weight Bracket: (from kg) |
|---|---|---|---|
| | 0.48 | 13.5 | 42- |
| | 0.58 | 16.2 | 51- |
| | 0.70 | 19.5 | 61-70 |

In another preferred embodiment the bracketed dosage regimen comprises the following bracket sizes:

| hGH equivalents (mg) | Weight Bracket: (from kg) |
|---|---|
| 3.0 | 11.5- |
| 3.6 | 14- |
| 4.3 | 16.5- |
| 5.2 | 20- |
| 6.3 | 24- |
| 7.6 | 29- |
| 9.2 | 35- |
| 11.0 | 42- |
| 13.3 | 51-60 |

Such bracketed dosage regimen is particularly preferred for patients which traditionally receive 0.24 mg of hGH/kg/week, such as for example EU patients.

Such bracketed dosage regimen may be achieved with a combination of two formulations having different strengths of hGH equivalents, namely 14 mg hGH equivalents/ml and 28 mg hGH equivalents/ml which results in the following bracketed dosage regimen:

| Strength | Volume (ml) | hGH equivalents (mg) | Weight Bracket: (from kg) |
|---|---|---|---|
| 14 mg hGH equivalents/ml | 0.21 | 3.0 | 11.5- |
| | 0.26 | 3.6 | 14- |
| | 0.31 | 4.3 | 16.5- |
| | 0.37 | 5.2 | 20- |
| 28 mg hGH equivalents/ml | 0.23 | 6.3 | 24- |
| | 0.27 | 7.6 | 29- |
| | 0.33 | 9.2 | 35- |
| | 0.39 | 11.0 | 42- |
| | 0.48 | 13.3 | 51-60 |

However, to avoid such small filling volumes in the unit dose to be used with the smallest bracket which might make the manufacturing process challenging, such bracketed dosage regimen more preferably may be achieved with a combination of two formulations having a lower strengths of hGH equivalents, namely 11 mg hGH equivalents/ml and 22 mg hGH equivalents/ml which results in the following bracketed dosage regimen:

| Strength | Volume (ml) | hGH equivalents (mg) | Weight Bracket: (from kg) |
|---|---|---|---|
| 11 mg hGH equivalents/ml | 0.27 | 3.0 | 11.5- |
| | 0.33 | 3.6 | 14- |
| | 0.39 | 4.3 | 16.5- |
| | 0.47 | 5.2 | 20- |
| 22 mg hGH equivalents/ml | 0.29 | 6.3 | 24- |
| | 0.35 | 7.6 | 29- |
| | 0.42 | 9.2 | 35- |
| | 0.50 | 11.0 | 42- |
| | 0.60 | 13.3 | 51-60 |

This preferred embodiment was developed combining the manufacturing capability of filling volumes (preferably larger than 0.25 ml) and the need for keeping the injection volume lower than or equal to 1.00 ml, preferably lower than or equal to 0.80 mL, most preferably lower than or equal to 0.60 ml. This combined with spacing the hGH equivalents in mg from 3 mg to 13.3 mg with approx. 20% increments led to the strength of the two formulations, namely 11 mg hGH equivalents/ml and 22 mg hGH equivalents/ml. By incorporating these two formulations all selected hGH equivalent doses in mg are with an injection volume lower or equal to the most preferred value of 0.60 ml.

The weight brackets associated with these selected hGH equivalent doses in mg were calculated using a mean dose of 0.24 mg/kg/week with an allowed variation of the weekly dose of 0.02 mg/kg. Hence, the lower limit of a weight bracket is calculated as 3.0 mg/0.26 mg/kg/week=11.5 kg. The associated higher weight bracket is then calculated as 3.0 mg/0.22 mg/kg=14 kg which was appropriately rounded.

Another aspect of the present invention is a method of treating growth hormone deficiency, wherein the method comprises the step of administering a long-acting growth hormone formulation in a bracketed dosing regimen. Preferably, the bracketed dosing regimen consists of a multitude of brackets with increasing doses of long-acting growth hormone and wherein the dose of long-acting growth hormone formulation in two neighboring brackets differs by at least 10%.

Another aspect of the present invention is the use of the multitude of unit dosage forms of the present invention in a method of treating growth hormone deficiency.

Another aspect of the present invention is a use of the multitude of unit dosage forms of the present invention as a medicament.

Another aspect of the present invention is a method of treating growth hormone deficiency, wherein the method comprises the step of administering a long-acting growth hormone formulation in a bracketed dosing regimen.

Another aspect of the present invention is a long-acting growth hormone formulation for use in treating growth hormone deficiency, wherein the long-acting growth hormone formulation is administered in a bracketed dosage regimen.

Another aspect of the present invention is the use of a long-acting growth hormone formulation for the manufacture of a sustained release medicament for use in the treatment of growth-hormone deficiency, wherein the medicament is prepared to be administered in a bracketed dosage regimen.

Another aspect of the present invention is a method of administering the long-acting growth hormone formulation comprised in the multitude of unit dosage forms of the present invention to a patient in need of growth hormone treatment, wherein the method comprises the step of injecting the long-acting growth hormone formulation subcutaneously.

EXAMPLES

Methods
Cation Exchange Chromatography

The purification of conjugates by cation exchange chromatography was performed using an ÄKTA Pure system (GE Healthcare) equipped with a Macrocap SP column with a column volume of 279 mL. The respective reaction mixture was applied to the column which was pre-equilibrated in 20 mM sodium acetate, 10 mM L-methionine buffer, pH 4.0 (buffer A). After loading, the column was washed with three column volumes of buffer A to remove any unreacted PEG reagent. Mono-Conjugates were eluted using a gradient of 0-30% buffer B (20 mM sodium acetate, 1 M sodium chloride, pH 4.5) over 15 column volumes. A gradient of 30-80% B over three column volumes was used to elute unreacted growth hormone. The column was cleaned with 3 column volumes of 100% buffer B. The flow rate was 20 mL/min for loading and 25 mL/min during the elution. The elution was monitored by detection at 280 nm.

Height and Height Velocity Measurements

Height measurements were performed using a calibrated wall-mounted (e.g. Harpenden or similar) stadiometer. The results were derived as an arithmetic mean from three separate measurements at each visit. The time of measurement and the auxologist's name, as well as the result were recorded. The calculation of height velocity was performed centrally.

Example 1: Synthesis of Transient 4×20 kDa mPEG-Linker-hGH Monoconjugate 1

4×20 kDa mPEG-linker-hGH monoconjugate 1 was synthesized according to a similar procedure as described in WO2009/133137 A2. The formulations of 4×20 kDa mPEG-linker-hGH monoconjugate 1 as shown in Table 1 were prepared.

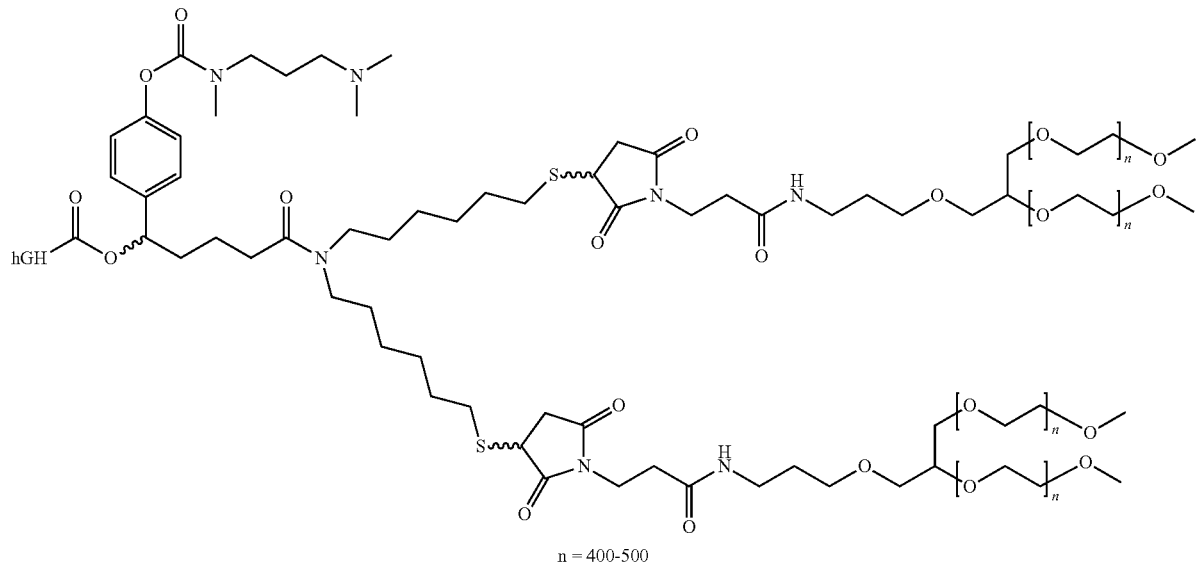

n = 400-500

TABLE 1

Formulations of 4 × 20 kDa mPEG-linker-hGH monoconjugate 1

| Formulation name: | Concentration of 4 × 20 kDa mPEG-linker-hGH monoconjugate 1 formulation [mg conjugate/mL] | Concentration of hGH eq. [mg hGH eq./mL] |
|---|---|---|
| 1A | 30 | 6 |
| 1B | 45 | 9 |
| 1C | 75 | 15 |

Example 2: Synthesis of Transient 4×10 kDa mPEG-Linker-hGH Monoconjugate 2

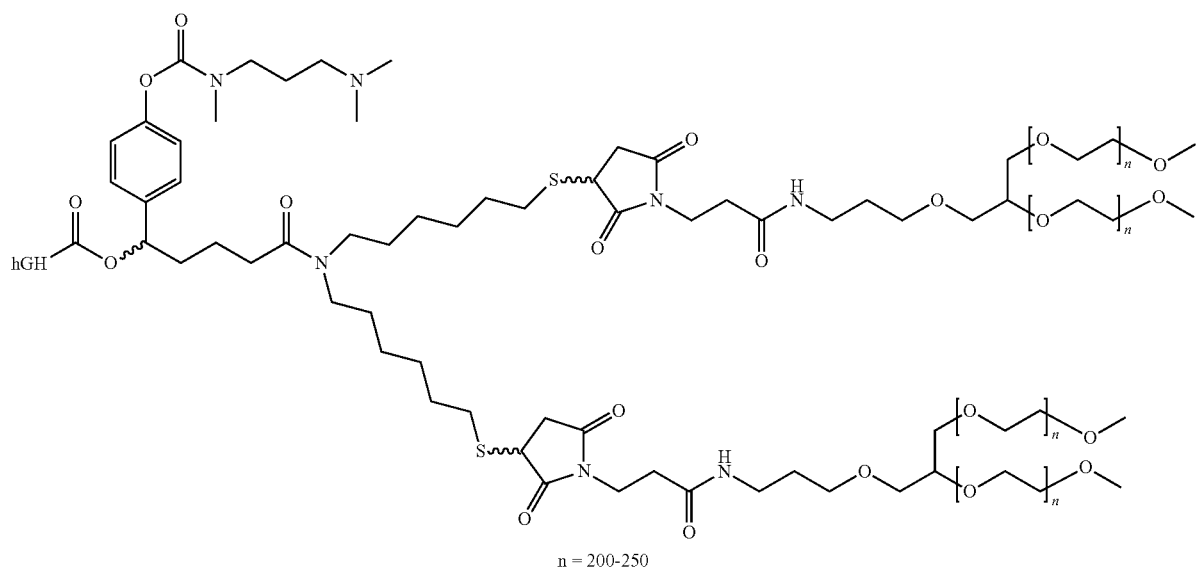

n = 200-250

4×10 kDa mPEG-linker-hGH monoconjugate 2 was synthesized according to a similar procedure as described in WO2009/133137 A2; in detail the manufacturing process was conducted as follows:

hGH was buffer exchanged to 100 mM sodium borate pH 9 and the concentration of hGH was adjusted to 10 mg/mL. A molar excess of 4-arm branched 40 kDa mPEG-pentafluorophenylcarbonate derivative relative to the amount of hGH was dissolved in water to form a 6% (w/w) reagent solution. The reagent solution was added to the hGH solution in a 1-to-1 ratio (based on weight) and mixed. The reaction mixture was incubated under stirring for 105 min at 12-16° C. and subsequently quenched by adding 4 volumes of a solution comprising 27 mM acetic acid and 12.5 mM L-methionine to 1 volume of the reaction mixture to lower the pH of the solution to 4-4.5. After sterile filtration, the reaction mixture was incubated at room temperature for 16±4 h. 4×10 kDa mPEG-linker-hGH monoconjugate 2 was purified by cation exchange chromatography.

Buffer exchange and adjustment to the desired concentration of 4×10 kDa mPEG-linker-hGH monoconjugate 2 was achieved using a tangential-flow filtration system. Herewith the eluate from the cation exchange chromatography was ultra-filtrated and dia-filtrated to formulation buffer (10 mM succinic acid, 85 g/L trehalose dihydrate, pH 5.0 with 1M Tris-solution). Using the same system the trehalose concentration was lowered to 65 g/L and the concentration of this stock solution adjusted to 105±3 mg/mL of 4×10 kDa mPEG-linker-hGH monoconjugate 2 (corresponding to 35±1 mg hGH eq./mL). The formulations as shown in Table 2 were prepared based on this stock-solution of compound 2 by diluting the stock solution with high strength formulation buffer (10 mM succinic acid, 89 g/L trehalose dihydrate, adjusted to pH 5.0 with 1M Tris-base).

TABLE 2

Formulations of 4 × 10 kDa mPEG-linker-hGH monoconjugate 2

| Formulation name: | Concentration of 4 × 10 kDa mPEG-linker-hGH monoconjugate 2 formulation [mg/mL] | Concentration of hGH eq. [mg hGH eq./mL] |
|---|---|---|
| 2A | 103.8 | 34.6 |
| 2B | 95.1 | 31.7 |
| 2C | 81.9 | 27.3 |
| 2D | 65.1 | 21.7 |
| 2E | 47.4 | 15.8 |

Example 3: Preparation of a Formulation Comprising 4×20 kDa mPEG-Linker-hGH Monoconjugate 1 for Clinical Studies For the usage as an investigational drug in clinical studies 4×20 kDa mPEG-linker-hGH monoconjugate 1 was transformed into a lyophilized drug product in Din2R glass vials. Each vial was filled with 1.110±0.056 mL Drug Substance of 4×20 kDa mPEG-linker-hGH monoconjugate 1 formulated to contain a nominal PEGylated protein content of 45 mg TransCon PEG hGH/mL (equivalent to 9 mg hGH/mL) which, following lyophilization, contains 50.0 mg TransCon PEG hGH (nominal) together with the excipients succinic acid, trehalose dihydrate and Tris as depicted in Table 3. Closing and capping of the vials was performed with the low pressure present during the secondary drying phase of lyophilization maintained in the vial.

TABLE 3

Formulation of 4 × 20 kDa mPEG-linker-hGH monoconjugate 1 (lyophilizate, 50 mg (10 mg hGH))

| Name of ingredient | Quality | Function | Nominal quantity (per vial) |
| --- | --- | --- | --- |
| 4 × 20 kDa mPEG-linker-hGH monoconjugate 1 | cGMP (Manufacturer specification) | Prodrug form of the active pharmaceutical ingredient (API), hGH | 50.0 mg (equivalent to 10.0 mg hGH) |
| Succinic acid | USP NF | Buffering agent | 1.31 mg |
| Trehalose Dihydrate | Ph. Eur./USP | Tonicifier/ lyoprotectant | 88.8 mg |
| Tris | Ph. Eur./USP | pH adjustment | q.s. to pH 5.0 |

Following reconstitution with water for injection (WFI), 4×20 kDa mPEG-linker-hGH monoconjugate 1 was presented as a single-use, sterile solution for subcutaneous (s.c.) injection. Each glass vial (Type I) contains 50.0 mg lyophilized 4×20 kDa mPEG-linker-hGH monoconjugate 1 (nominal) which is stoppered with a FluroTec® coated, bromobutyl rubber stopper, secured with a plastic/aluminum cap. Upon reconstitution with 1.00 mL WFI, the formulation of the resulting 1.11 mL of drug product is as presented in Table 4.

TABLE 4

Formulation of reconstituted 4 × 20 kDa mPEG-linker-hGH monoconjugate 1

| Name of ingredient | Quality | Function | Strength (nominal) |
| --- | --- | --- | --- |
| 4 × 20 kDa mPEG-linker-hGH monoconjugate 1 | cGMP (Manufacturer specification) | Prodrug form of the active pharmaceutical ingredient (API), hGH | 45 mg 4 × 20 kDa mPEG-linker-hGH mono-conjugate 1 |
| Succinic acid | USP NF | Buffering agent | 10 mM |
| Trehalose Dihydrate | Ph. Eur./USP | Tonicifier | 80 mg/mL |
| Tris | Ph. Eur./USP | pH adjustment | q.s. to pH 5.0 |
| Water for injection | Ph. Eur./USP | Solvent | 1.00 mL |

Example 4: Phase 2 Pediatric Study

The formulation of example 3 comprising TransCon hGH compound 1 was studied in a Phase 2 pediatric in around 48 treatment-naïve pre-pubertal patients with GHD. Pediatric patients were enrolled across Europe and North Africa who meet internationally recognized criteria for GHD, including short stature as measured by height and height velocity, two hGH stimulation tests, a bone age evaluation and IGF-I levels below −1 standard deviation score, or SDS. The Phase 2 pediatric study was a six-month multi-center, randomized study comparing three fixed doses of the formulation of example 3 comprising TransCon hGH compound 1 administered once per week at doses of 0.14 mg/kg/week, 0.21 mg/kg/week and 0.30 mg hGH/kg/week. The main efficacy endpoint was annualized height velocity at six months.

An interim analysis consisting of 25 patients, representing approximately 50% of the anticipated total enrollment in the study, completing three months of the total six months of treatment, demonstrated that mean annualized height velocities were comparable, ranging from 13.0 cm to 14.1 cm for the three weekly dose levels of TransCon hGH compound 1

In conclusion, chronic administration of TransCon hGH compound 1 for 13 weeks is safe and well tolerated and is associated with acceleration of growth at a rate comparable to daily hGH administered at a comparable weekly dose. The annualized height velocities were very similar across the dose range from 0.14 mg/kg/week to 0.30 mg hGH/kg/week, with a flat dose response curve which led to the surprising observation that fixed dose adjustment according to weight of a long acting growth hormone is not required across the dose range commonly used for treatment of growth hormone deficiency with daily hGH in Europe and US.

Abbreviations

AIDS acquired immune deficiency syndrome
API active pharmaceutical ingredient
cGMP current good manufacturing practice
CRI chronic renal insufficiency
GHD growth hormone deficiency
hGH human growth hormone
HIV human immunodeficiency virus
ISS idiopathic short stature
mPEG methoxypoly(ethylene glycol)
NS Noonan syndrome
PEG poly(ethylene glycol)
Ph. Eur. European Pharmacopeia
PWS Prader-Willi syndrome
SBS short bowel syndrome
SGA children born small for gestational age
SHOX short stature homeobox
USP United States Pharmacopeia
Tris Tris(hydroxymethyl)-aminomethan
TS Turner syndrome

The invention claimed is:

1. A method of treating growth hormone deficiency in human children, the method comprising:
a step of administering to human children patients in need thereof a long-acting growth hormone formulation in a bracketed dosing regimen in which a range of patients' weights is allocated a particular dose of drug, which weight range is referred to as a "weight bracket";
wherein dosage increases occur in a step-wise manner and wherein a bracketed dosage regimen has between 3 and 20 weight brackets;
wherein the dose a patient receives measured in mg hGH equivalents per week is the same for all patients within that weight bracket;
wherein the dose of one weight falling into each particular weight bracket corresponds to 0.24 mg/kg/week;
wherein patients of the same bracket having a lower weight receive a dose that is higher than said dose of the fixed dosage regimen and patient of the same bracket having a higher weight receive a dose that is lower than said dose of the fixed dosage regimen, wherein the dose received by a patient with the lowest weight within a bracket is 15-22% higher than the dose received by a patient with the highest weight within a bracket; and wherein if a patient's weight exceeds the weight of a particular weight bracket the dose is increased to the dose of the next weight bracket, which dose of growth hormone equivalents in two neighboring brackets increases by at least 10%;

wherein the long-acting growth hormone formulation comprises a compound of formula IV:

(IV)

-continued

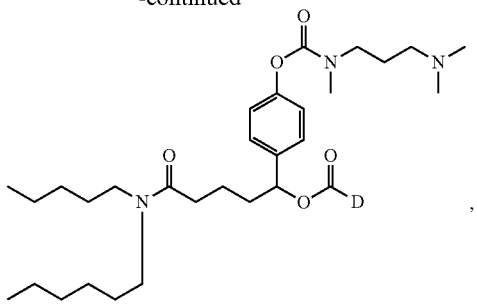

wherein D is an hGH moiety having the amino acid sequence of SEQ ID NO: 1 connected to the rest of the molecule through an amine functional group; and p1, p2, p3 and p4 are independently selected from 200-250.

2. The method of claim 1;
wherein the long-acting growth hormone formulation is a lyophilized formulation that is reconstituted prior to administration.

3. The method of claim 1;
wherein the long-acting growth hormone formulation is a liquid formulation.

4. The method of claim 1;
wherein the long-acting growth hormone formulation is administered via a prefilled syringe.

5. The method of claim 1;
wherein the long-acting growth hormone formulation is administered via a pen injector.

6. The method of claim 1;
wherein the long-acting growth hormone formulation is contained in a dual chamber cartridge.

7. The method of claim 6;
wherein the dual chamber cartridge is utilized with a syringe to administer the long-acting growth hormone formulation.

8. The method of claim 6;
wherein the dual chamber cartridge is utilized with a pen device or electronic injector to administer the long-acting growth hormone formulation.

9. The method of claim 1;
wherein all increases between neighboring brackets are by a constant percentage value.

10. The method of claim 1;
wherein the bracketed dosage regimen comprises 3 to 15 brackets.

11. The method of claim 1;
wherein doses of the long-acting growth hormone formulation are administered to a patient with a time period of at least two days between two consecutive doses.

12. The method of claim 1;
wherein the bracketed dosing regimen of the long-acting growth hormone formulation is continued for a time period of at least 6 months.

13. The method of claim 1;
wherein doses of the long-acting growth hormone formulation are administered to a patient with a time period of seven days between two consecutive doses.

14. The method of claim 1;
wherein the dose of growth hormone equivalents in two neighboring brackets increases from 15 to 40%.

15. The method of claim 1;
wherein the dose of growth hormone equivalents in two neighboring brackets increases from 18 to 30%.

16. The method of claim 1;
wherein the bracketed dosage regimen has between 6 and 14 weight brackets.

17. The method of claim 1;
wherein the growth hormone deficiency is treated for a time period of at least 24 months.

18. The method of claim 1, wherein the bracketed dosage regime has 12 brackets.

19. The method of claim 1, wherein the bracketed dosage regime is supplied from nine unit dosages.

20. The method of claim 1, wherein the weight brackets and their respective dosages comprise:

| Weight bracket (kg) | Dose Mg/week |
|---|---|
| 11.5-13.9 | 3 |
| 14-16.4 | 3.6 |
| 16.5-19.9 | 4.3 |
| 20-23.9 | 5.2 |
| 24-28.9 | 6.3 |
| 29-34.9 | 7.6 |
| 35-41.9 | 9.1 |
| 42-50.9 | 11 |

* * * * *

UNITED STATES PATENT AND TRADEMARK OFFICE
CERTIFICATE OF CORRECTION

PATENT NO. : 12,016,903 B2
APPLICATION NO. : 15/528350
DATED : June 25, 2024
INVENTOR(S) : Kennett Sprogøe et al.

Page 1 of 3

It is certified that error appears in the above-identified patent and that said Letters Patent is hereby corrected as shown below:

In the Specification

In Columns 31-32, Lines 35-67, delete

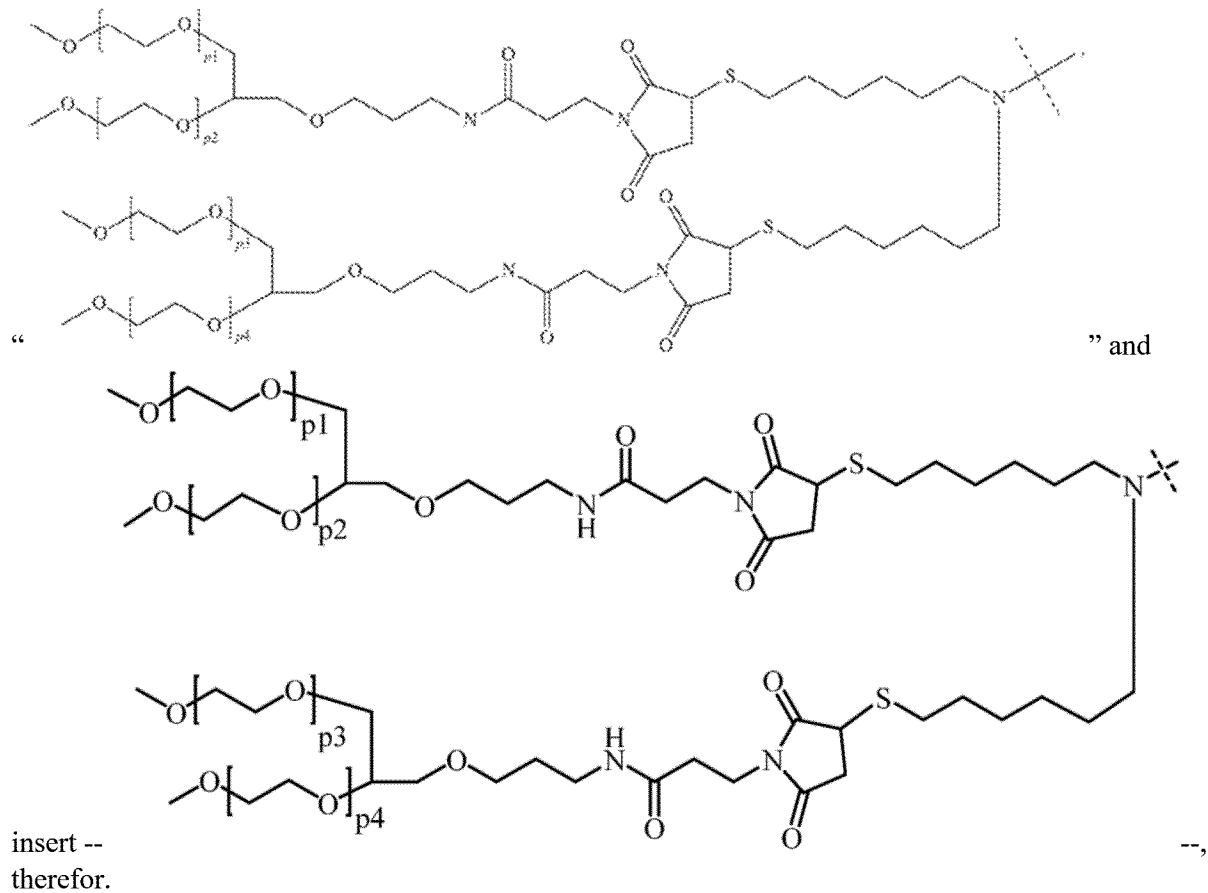

" and " insert -- -- , therefor.

Signed and Sealed this
Seventeenth Day of September, 2024

Katherine Kelly Vidal
*Director of the United States Patent and Trademark Office*

CERTIFICATE OF CORRECTION (continued)
U.S. Pat. No. 12,016,903 B2

Page 2 of 3

In Columns 35-36, Lines 32-67, delete

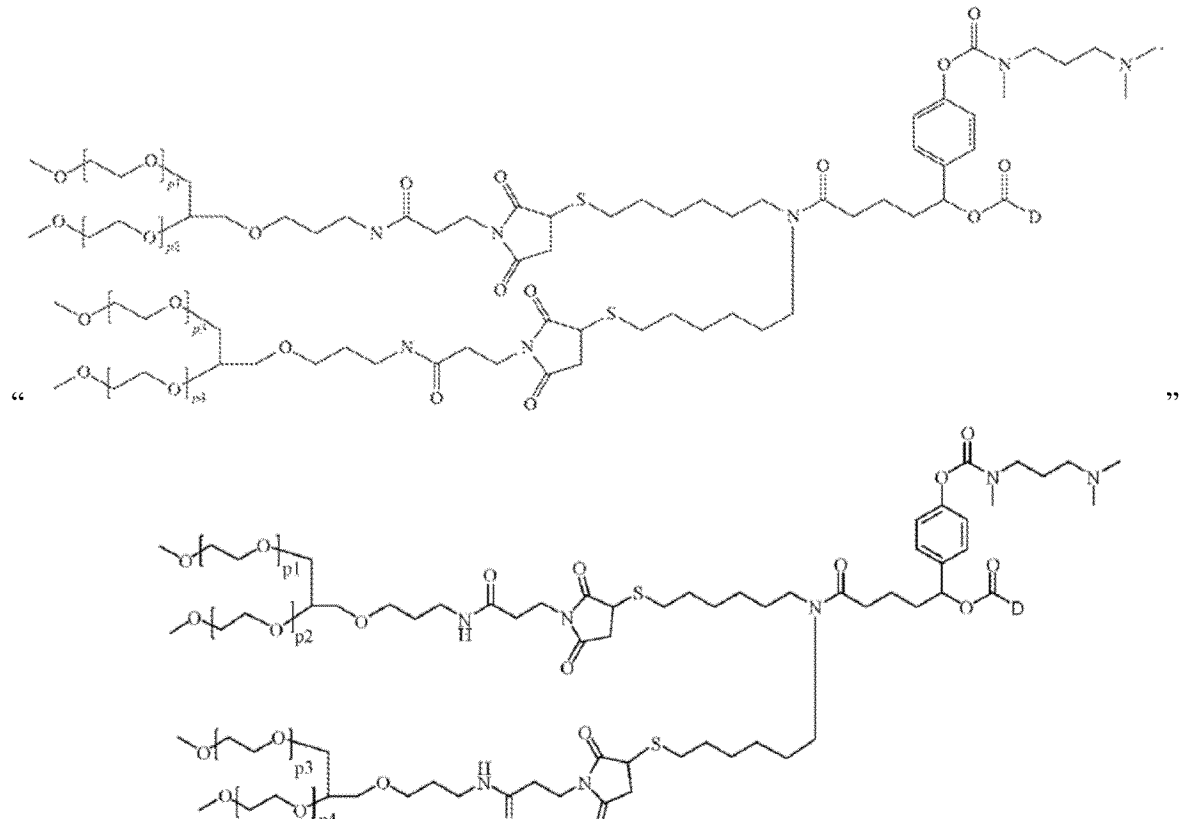

and insert --
therefor.

In the Claims

In Columns 64-65, Lines 57-67 & 1-14, Claim 1, delete

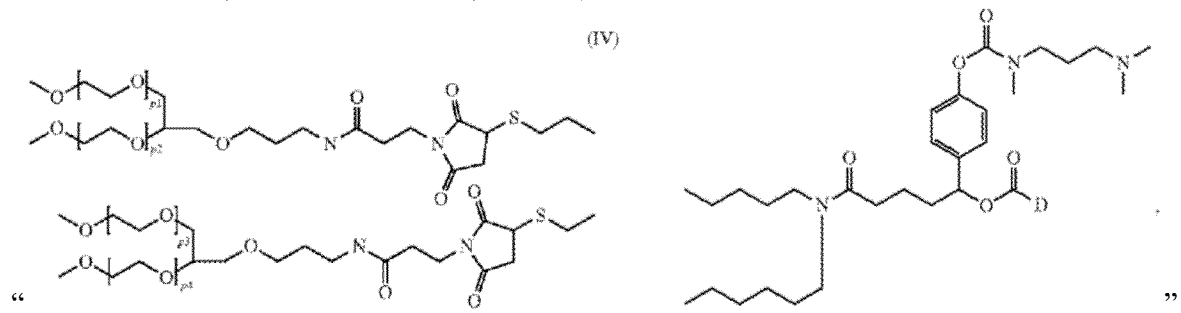

CERTIFICATE OF CORRECTION (continued)
U.S. Pat. No. 12,016,903 B2

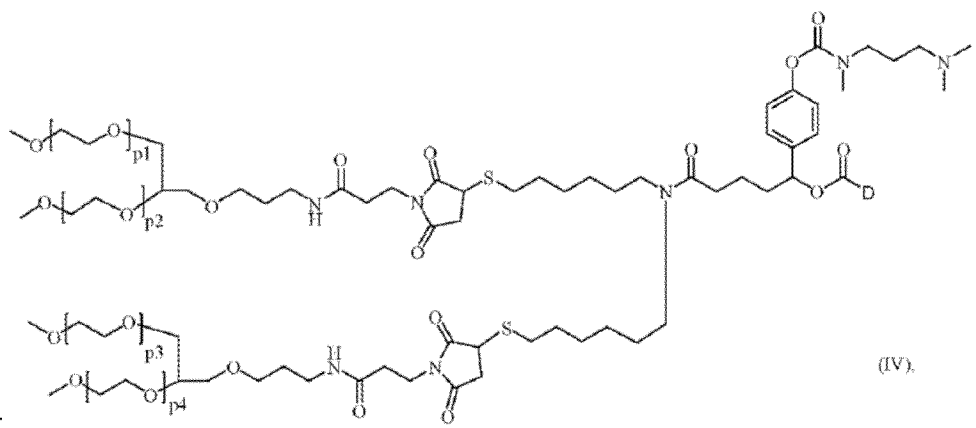

and insert -- --,
therefor.

At Claim 20, Column 66, Lines 30-48, delete " _____ " and insert

| Weight bracket (kg) | Dose mg/week |
|---|---|
| 11.5 – 13.9 | 3 |
| 14 – 16.4 | 3.6 |
| 16.5 – 19.9 | 4.3 |
| 20 – 23.9 | 5.2 |
| 24 – 28.9 | 6.3 |
| 29 – 34.9 | 7.6 |
| 35 – 41.9 | 9.1 |
| 42 – 50.9 | 11 |

--, therefor.